(12) United States Patent
Sharp et al.

(10) Patent No.: US 9,803,243 B2
(45) Date of Patent: Oct. 31, 2017

(54) BIOMARKERS FOR DIAGNOSIS OF STROKE AND ITS CAUSES

(71) Applicant: The Regents of the University of California, Oakland, CA (US)

(72) Inventors: Frank Sharp, Davis, CA (US); Boryana Stamova, Davis, CA (US); Glen C. Jickling, Sacramento, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 15/068,600

(22) Filed: Mar. 13, 2016

(65) Prior Publication Data

US 2016/0265059 A1 Sep. 15, 2016

Related U.S. Application Data

(62) Division of application No. 13/182,779, filed on Jul. 14, 2011, now abandoned.

(60) Provisional application No. 61/364,449, filed on Jul. 15, 2010.

(51) Int. Cl.
*C12Q 1/68* (2006.01)
*G01N 33/68* (2006.01)

(52) U.S. Cl.
CPC ....... *C12Q 1/6883* (2013.01); *G01N 33/6896* (2013.01); *C12Q 2600/158* (2013.01); *C12Q 2600/16* (2013.01); *G01N 2800/2871* (2013.01); *G01N 2800/50* (2013.01)

(58) Field of Classification Search
None
See application file for complete search history.

(56) References Cited

U.S. PATENT DOCUMENTS

| | | | |
|---|---|---|---|
| 9,057,109 B2 | 6/2015 | Chang | |
| 9,200,322 B2 | 12/2015 | Barr et al. | |
| 9,410,204 B2 | 8/2016 | Sharp et al. | |
| 2001/0053519 A1 | 12/2001 | Fodor et al. | |
| 2002/0115120 A1 | 8/2002 | Kapeller-Libermann et al. | |
| 2003/0119064 A1 | 6/2003 | Valkirs et al. | |
| 2003/0199000 A1 | 10/2003 | Valkirs et al. | |
| 2004/0191783 A1 | 9/2004 | Leclercq et al. | |
| 2004/0203083 A1 | 10/2004 | Buechler et al. | |
| 2006/0046259 A1 | 3/2006 | Baird et al. | |
| 2006/0078882 A1 | 4/2006 | Zetter et al. | |
| 2007/0042425 A1 | 2/2007 | Hochstrasser et al. | |
| 2007/0050146 A1 | 3/2007 | Bentwich et al. | |
| 2007/0280917 A1 | 12/2007 | Helgadottir | |
| 2009/0197774 A1 | 8/2009 | Kozian et al. | |
| 2010/0105046 A1 | 4/2010 | Epstein et al. | |
| 2010/0197518 A1 | 8/2010 | Xu et al. | |
| 2010/0216115 A1 | 8/2010 | Yan et al. | |
| 2012/0015904 A1 | 1/2012 | Sharp et al. | |
| 2012/0065087 A1 | 3/2012 | Sharp et al. | |
| 2012/0316076 A1 | 12/2012 | Sharp et al. | |
| 2015/0018234 A1 | 1/2015 | Sharp et al. | |
| 2016/0222455 A1 | 8/2016 | Xu et al. | |
| 2016/0237501 A1 | 8/2016 | Sharp et al. | |
| 2016/0289765 A1 | 10/2016 | Sharp et al. | |
| 2017/0029891 A1 | 2/2017 | Sharp et al. | |

FOREIGN PATENT DOCUMENTS

| | | |
|---|---|---|
| WO | WO 02/12892 | 2/2002 |
| WO | WO 03/016910 | 2/2003 |
| WO | WO 2005/116268 | 12/2005 |
| WO | WO 2006/036220 | 4/2006 |
| WO | WO 2008/137465 | 11/2008 |
| WO | WO 2010/012834 | 2/2010 |
| WO | WO 2012/009547 | 1/2012 |
| WO | WO 2012/009567 | 1/2012 |
| WO | WO 2012/121978 | 9/2012 |
| WO | WO 2013/103781 | 7/2013 |

OTHER PUBLICATIONS

U.S. Appl. No. 15/043,577, filed Feb. 14, 2016, Sharp et al.
U.S. Appl. No. 15/091,181, filed Apr. 5, 2016, Sharp et al.
U.S. Appl. No. 15/092,599, Apr. 6, 2016, Xu et al.
PCT International Search Report and Written Opinion dated Jul. 25, 2008 issued in PCT/US2008/062064.
PCT International Preliminary Report on Patentability dated Nov. 3, 2009 issued in PCT/US2008/062064.
PCT International Search Report and Written Opinion dated Mar. 28, 2012 issued in PCT/US2011/044062.
PCT International Preliminary Report on Patentability dated Jan. 15, 2013 issued in PCT/US2011/044062.
PCT International Search Report and Written Opinion dated Mar. 28, 2012 issued in PCT/US2011/044023.
PCT International Preliminary Report on Patentability dated Jan. 15, 2013 issued in PCT/US2011/044023.
PCT International Search Report and Written Opinion dated Oct. 24, 2012 issued in PCT/US2012/027316.
PCT International Preliminary Report on Patentability dated Sep. 10, 2013 issued in PCT/US2012/027316.
PCT International Search Report and Written Opinion dated Apr. 12, 2013 issued in PCT/US2013/020240.
PCT International Preliminary Report on Patentability dated Jul. 8, 2014 issued in PCT/US2013/020240.
European Extended Search Report dated Mar. 16, 2011 issued in EP10014221.5.
European Extended Search Report dated Nov. 12, 2013 issued in EP11807532.4.
European Extended Search Report dated Apr. 11, 2014 issued in EP11807519.1.
"Affymetrix GeneChip Human Genome U133 Array Set HG-U133B," *GEO Accession viewer* (Mar. 11, 2002), XP002427171 pp. 1-4.
"Affymetrix GeneChip Human Genome U133 plus 2.0 Array," *GEO Accession viewer* 7 (Nov. 7, 2003), XP002343693 pp. 1-3.
Barr et al. (2010) "Genomic biomarkers and cellular pathways of ischemic stroke by RNA gene expression profiling" *Neurology* 75:1009-1014.
Benner et al. (2001) "Evolution, language and analogy in functional genomics," *Trends in Genetics* 17(7):414-418.
Cheung et al. (2003) "Natural variation in human gene expression assessed in lymphoblastoid cells," *Nature Genetics* 33:422-425.

(Continued)

*Primary Examiner* — Addison D Ault
(74) *Attorney, Agent, or Firm* — Weaver Austin Villeneuve & Sampson LLP

(57) ABSTRACT

The present invention provides compositions and methods for the diagnosis of the occurrence and cause of stroke.

8 Claims, 18 Drawing Sheets

(56) References Cited

OTHER PUBLICATIONS

Cobb et al. (2002) "Sepsis gene expression profiling: Murine splenic compared with hepatic responses determined by using complementary DNA microarrays," *Crit Care Med* 30(12):2711-2721.

Crawford et al., (2007) "The biological importance of measuring individual variation," *J. Exp. Biol.* 210:1613-1621.

Davi et al. (2009) "CD40 ligand and MCP-1 as predictors of cardiovascular events in diabetic patients with stroke," *J. Atheroscler. Thromb.* 16:707-713.

Ferronato et al. (2010) "Upregulated Expression of Toll-like Receptor 4 in Peripheral Blood of Ischaemic Stroke Patients Correlates with Cyclooxygenase 2 Expression," *European Journal of Vascular and Endovascular Surgery* 41(3): 358363.

Fling et al. (2008) "A biomarker panel for peripheral arterial disease," *Vasc. Med.* 13:217-224.

Greenbaum et al. (2003) "Comparing protein abundance and mRNA expression levels on a genomic scale," *Genome Biology* 4:117(1-8).

Haller et al. (2004) "Equivalence test in quantitative reverse transcription polymerase chain reaction: confirmation of reference genes suitable for normalization," *Anal. Biochem.* 335:1-9.

Hassan et al. (2003) "Marker of endothelial dysfunction in lacunar infarction and ischaemic leukoaraiosis," *Brain* 126:424-432.

Hou et al. (2003) "High-density DNA Microarray Analysis of Gene Expression Following Transient Focal Cerebral Ischemia in Mouse," *International Congress Series* 1252:45-56.

Jensen et al. (2008) "The promise and potential pitfalls of serum biomarkers for • ischemic stroke and transient ischemic attack," *Neurologist* 14(4):243-246.

Jensen et al. (2009) "Potential biomarkers for the diagnosis of stroke," *Expert Review of Cardiovascular Therapy*, 7(4):389-93.

Jickling et al. (2010) "Biomarkers of ischemic stroke," *US Neurology*, 5(2):52-54.

Jickling et al. (Nov. 2010) "Signatures of cardioembolic and large vessel • ischemic stroke," *Ann Neurol.*, 68(5):681-692.

Jickling et al. (2011) "Profiles of lacunar and non-lacunar stroke," *Ann Neurol.*, 70(3):477-485.

Jickling et al. (2012) "Prediction of cardioembolic, arterial and lacunar causes of cryptogenic stroke by gene expression and infarct location," *Stroke*, 43(8): 2036-2041 [doi:10.1161/Strokeaha.111. 648725 pp. 1-12].

Karl-Olof Lövblad et al. (2006) "Actual diagnostic approach to the acute stroke patient,"*Neuro Eur Radiol*, 16:1253-1269.

Laskowitz et al. (2005) "Panel of Biomarkers Predicts Stroke," *Ann. N. Y. Acad. Sci.*, 1053:30.

Leypoldt et al. (2009) "Dimethylarginine Dimethylaminohydrolase-1 Transgenic Mice are not Protected from Ischemic Stroke," *PlosOne*, 4(10):e7337(1-4).

Li et al. (Oct. 2013) "Transcriptome Analysis Reveals Distinct Patterns of Long Noncoding RNAs in Heart and Plasma of Mice with Heart Failure," *PLOS One*, 8(10):e77938, 10 pp.

Lim et al. (2010) "MicroRNA in Cerebral Ischemia," *Translational Stroke Research*, 1:287-303.

Lynch et al. (2004) "Novel diagnostic test for acute stroke," *Stroke*, 35(1):57-63.

May et al. (1988) "How many species are there on Earth," *Science*, 241:1441-1449.

Montaner et al. (2008) "Etiologic diagnosis of ischemic stroke subtypes with plasma biomarkers," *Stroke*, 39(8):2280-2287.

Moore et al. (2005) "Using peripheral blood mononuclear cells to determine a gene expression profile of acute ischemic stroke: a pilot investigation," *Circulation*, 111(2):212-21.

Patel et al. (Dec. 12, 2001) "Lack of Clinical Significance of Early Ischemic Changes on Computed Tomography in Acute Stroke," *Jama*, 286(22):2830-2838.

Pradervand et al. (2008) "Affymetrix Whole-Transcript Human Gene 1.0 ST array is highly concordant with standard 3'expression arrays," *BioTechniques*, 44(6):759-762.

Read et al. (2001) "Stroke Genomics: Approaches to Identify, Validate, and Understand Ischemic Stroke Gene Expression," *J. Cereb. Blood Flow Metab.*, 21:755778.

Reynolds et al. (2003) "Early Biomarkers of Stroke," *Clin. Chem.*, 49:1733-1739.

Rothwell et al. (2007) "Effect of urgent treatment of transient ischaemic attack and minor stroke on early recurrent stroke (Express study): A prospective population-based sequential comparison," *Lancet*, 370:1432-42.

Sendera et al. (2002) "Expression Profiling with Oligonucleotide Arrays: Technologies and Applications for Neurobiology," *Neurochemical Research*, 27:10051026.

Sharp et al. (2007) "Genomic Profiles of Stroke in Blood," *Stroke*, 28:691-693.

Slogoff et al. (1985) "Does Perioperative Myocardial Ischemia Lead to Postoperative Myocardial Infarction?" *Anesthesiology*, 62:107-114.

Stamova et al. (2009) "Identification and validation of suitable endogenous reference genes for gene expression studies in human peripheral blood," *BMC Medical Genomics* 2:49 pp. 1-13.

Stamova et al. (2010) "Gene Expression Profiling of Blood for the Prediction of Ischemic Stroke," Supplementary Material, *Stroke*, 41(10):2171-2177, 26 pages.

Stapleton et al. (Mar. 1999) "Prospective Comparison of Whole-Blood- and Plasma-Based Hepatitis C Virus RNA Detection Systems: Improved Detection Using Whole Blood as the Source of Viral RNA," *Journal of Clinical Microbiology*, 37(3):484-489.

Swarup et al. (2007) "Circulating (cell-free) nucleic acids—A promising, non-invasive tool for early detection of several human diseases," *FEBS Letters*, 581:795799.

Tang et al. (2005) "Blood Gene Expression Profiling of Neurologic Diseases: A Pilot Microarray Study," *Arch Neurol.*, 62:210-215.

Tang et al. (2006) "Gene expression in blood changes rapidly in neutrophils and monocytes after ischemic stroke in humans: a microarray study," *Journal of Cerebral Blood Flow and Metabolism*, 26(8): 1089-1102.

Thellin et al. (1999) "Housekeeping genes as internal standards: use and limits," *J. Biotechnol.*, 75:291-295.

Tombul et al. (2005) "Hemostatic markers and platelet aggregation factors as predictive markers for type of stroke and neurological disability following cerebral infarction," *Journal of Clinical Neuroscience*, 12(4): 429-434.

Veltkamp et al. (2002) "Transient focal ischemia increases endothelial nitric oxide synthase in cerebral blood vessels," *Stroke*, 33(11):2704-2710.

Viswanathan et al. (2006) "Cerebral Microhemorrhage," *Stroke, Journal of the American Heart Association*, 37:550-555.

Whiteley et al. (2008) "Blood Biomarkers in the Diagnosis of Ischemic Stroke: A Systematic Review," *Stroke*, 39(10):2902-2909.

Whiteley et al. (2009) "Blood Markers for the Prognosis of Ischemic Stroke: A Systematic Review," *Stroke*, 40:e380-e389, 27pp.

Xu et al. (2008) "Gene expression in peripheral blood differs after cardioembolic compared with large-vessel atherosclerotic stroke: biomarkers for the etiology of ischemic stroke," *J Cereb Blood Flow Metab.*, 28(7):1320-1328 [Epub Apr. 2, 2008].

Zhan et al. (2011) "Transient ischemic attacks characterized by RNA profiles in blood," *Neurology*, 77(19): 1718-1724.

Zhan et al. (2010) "Brief focal cerebral ischemia that simulates transient ischemic attacks in humans regulates gene expression in rat peripheral blood" *J Cereb Blood Flow Metab.*, 30(1):110-118 Doi: 10.1038/jcbfin.2009.189.

Ziegler et al. (2007) "TLR2 has a Detrimental role in Mouse Transient Focal Cerebral Ischemia," *Biochemical and Biophysical Research Communication*, 359:574579.

Indian First ExaminationReport dated Dec. 13, 2016 issued in IN3762/KOLNP/2009 [UCDVP028IN].

"*Homo sapiens* disabled homolog 2, mitogen-responsive phosphoprotein (Drosophila), mRNA (cDNA clone MGC:1764 IMAGE:3504380)," Accession:BC003064.2, GI: 33870637, complete cds [Downloaded on Feb. 21, 2017 at https://www.ncbi.nim. nih.gov/nuccore/BC003064.2?report-girevhist]. 1 page.

Jakobsen et al., (1990) "Purification of mRNA directly from crude plant tissues in 15 minutes using magnetic oligo dT microspheres," *Nucleic Acids Research*, 18(12):3669.

Figure 2A-C

Test set Prediction Confusion Matrix (Threshold=0)

| True\Predicted | Healthy | IS_3h | Correct Classification, % |
|---|---|---|---|
| Healthy | 18 | 1 | 94.73 |
| IS_3h | 4 | 29 | 87.9 |

A
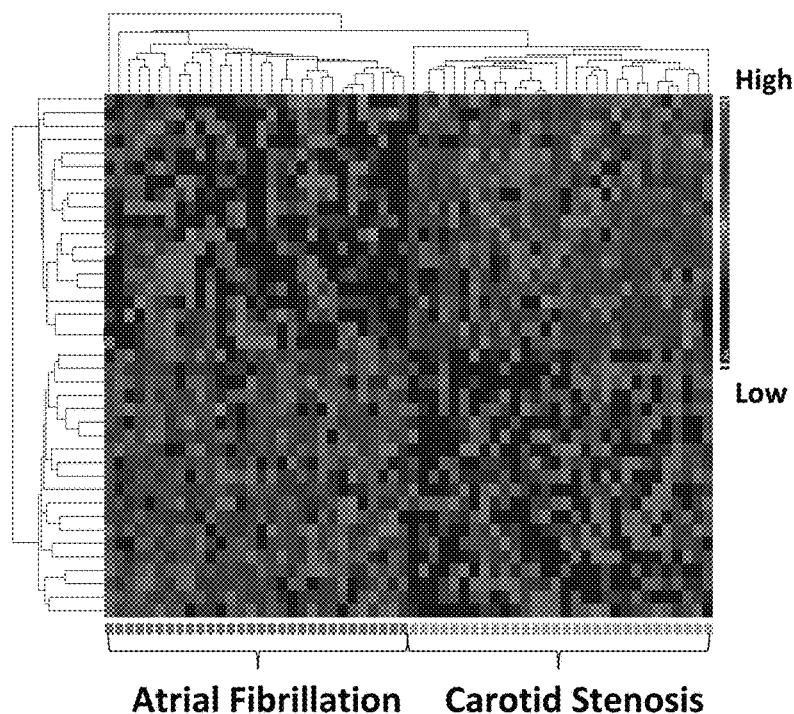
Atrial Fibrillation    Carotid Stenosis
B
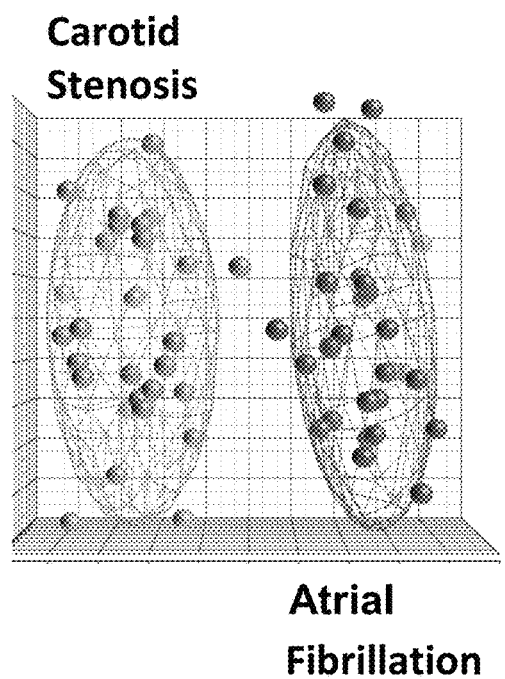
*Figure 15A-B*

BIOMARKERS FOR DIAGNOSIS OF STROKE AND ITS CAUSES

CROSS-REFERENCE TO RELATED APPLICATIONS

This application is a divisional of U.S. application Ser. No. 13/182,779, filed on Jul. 14, 2011, which claims the benefit of U.S. Provisional Application No. 61/364,449, filed on Jul. 15, 2010, which are hereby incorporated herein by reference in their entireties for all purposes.

STATEMENT AS TO RIGHTS TO INVENTIONS MADE UNDER FEDERALLY SPONSORED RESEARCH AND DEVELOPMENT

This invention was made with Government support under Grant No. NS056302, awarded by the National Institutes of Health and National Institute of Neurological Disorders and Stroke (NINDS) and Grant No. 077501 4N, awarded by the American Heart Association. The government has certain rights in this invention.

FIELD OF THE INVENTION

The present invention provides compositions and methods for diagnosing stroke and the risk of stroke, as well as the cause of stroke.

BACKGROUND OF THE INVENTION

Stroke is a leading cause of adult death and disability [Thom T et al., *Circulation*, 113:e85-151 (2006); WHO, The atlas of heart disease and stroke (2005)]. The diagnosis of ischemic stroke (IS) is made with clinical assessment in combination with brain imaging. However, the diagnosis is not always straightforward, particularly in the acute setting where an accurate, inexpensive and rapid diagnosis is critical to optimally treat patients.

Extensive efforts have been directed toward identifying blood based biomarkers for IS. More than 58 proteins and 7 panels of proteins have been described as biomarkers of IS [Whiteley W et al., *Stroke*, 39:2902-2909 (2008); Foerch C et al., *Neurology*, 73:393-399 (2009); Jensen M B et al., *Expert Rev Cardiovasc Ther.*, 7:389-393 (2009)]. RNA expression profiles in the blood have also been described in IS [Tang Y et al., *J Cereb Blood Flow Metab.*, 26:1089-1102 (2006); Moore D F et al., *Circulation*, 111:212-221 2005]. We previously reported a 29-probe set expression profile predictive of IS [Tang Y et al., *J Cereb Blood Flow Metab.*, 26:1089-1102 (2006)]. This profile required validation in a second cohort, which has been done in the current study. Herein is described a 97-probe set expression profile that differentiates IS from controls, e.g., individuals who are healthy, have vascular risk factors, or who have experienced myocardial infarction. These profiles represent further refinement of gene expression as a diagnostic tool in patients with acute IS.

Ischemic stroke is most commonly classified using the Trial of ORG 10172 in Acute Stroke Treatment (TOAST) criteria, dividing patients into cardioembolic, large vessel, small vessel lacunar, other, and cryptogenic causes [Adams H P, Jr., et al., *Stroke*, 24:35-41 (1993)]. TOAST criteria improves rater reliability and guides treatment when a known cause can be clearly identified [Goldstein L B et al., *Stroke*, 32:1091-1098 (2001); Ay H et al., *Stroke*, 38:2979-2984 (2007)]. However, in many patients the cause of stroke remains unknown or cryptogenic in spite of extensive investigation. Given cryptogenic stroke accounts for approximately 30% of all ischemic strokes, better tools identify the cause of stroke are required [Ionita C C et al., *Prev Cardiol.*, 8:41-46 (2005)].

Blood based biomarkers present a valuable tool to determine the cause of stroke. A number of protein biomarkers have been associated with stroke subtypes. For example, cardioembolic stroke is associated with brain natriuretic peptide and D-dimer; large vessel stroke is associated with C-reactive protein; and small vessel lacunar stroke is associated with homocysteine, ICAM-1, and thrombomodulin [Laskowitz D T et al., *Stroke*, 40:77-85 (2009); Shibazaki K et al., *Intern Med.*, 48:259-264 (2009); Montaner J et al., *Stroke*, 39:2280-2287 (2008); Hassan A et al., *Brain*, 126:424-432 (2003)]. However, biomarkers of ischemic stroke subtype currently lack sufficient sensitivity and specificity to be used in clinical practice. Thus, a combination of biomarkers into a biomarker profile might be one method by which diagnostic specificity and sensitivity can be improved.

The present study determined that gene expression signatures in blood can be used to distinguish cardioembolic from large vessel ischemic stroke, and can be used to predict the cardioembolic and large vessel causes in patients with cryptogenic stroke. The rationale for why changes in blood cell RNA expression occur in ischemic stroke include inflammatory changes associated with acute cerebral ischemia, symptomatic atherosclerosis and thromboembolism [Xu H et al., *J Cereb Blood Flow Metab.*, 28:1320-1328 (2008) 9; Tang Y et al., *J Cereb Blood Flow Metab.*, 26:1089-1102 (2006); Du X et al., *Genomics*, 87:693-703 (2006)]. Using whole genome microarrays, a 40 gene profile was identified to distinguish cardioembolic stroke from large vessel stroke, and a 37 gene profile was identified to distinguish cardioembolic stroke due to atrial fibrillation from non-atrial fibrillation causes. These genes play roles in inflammation and represent a step toward better determining the cause of cryptogenic stroke.

BRIEF SUMMARY OF THE INVENTION

The present invention provides methods for diagnosing or predicting the occurrence of stroke and the cause of stroke by determining the overexpression and underexpression of biomarkers in blood.

Accordingly, in one aspect, the invention provides methods for diagnosing the occurrence and cause of ischemic stroke or a predisposition for developing ischemic stroke, the method comprising:

a) determining a level of expression of at least 15 ischemic stroke-associated biomarkers in a biological sample from a patient, wherein the biomarkers are selected from the group consisting of a plurality of biomarkers selected from Table 7A, a plurality of biomarkers selected from Table 13A, a plurality of biomarkers selected from Table 14 and a plurality of biomarkers selected from Table 15;

b) comparing the level of expression of the ischemic stroke-associated biomarkers to the expression level of a plurality of stably expressed endogenous reference biomarkers, wherein an increase or decrease of the expression level of the plurality of biomarkers selected from Table 7A compared to the expression level of the plurality of endogenous reference biomarkers indicates that the patient suffers from or is at risk of developing ischemic stroke;

wherein an increase or decrease of the expression level of the plurality of biomarkers selected from Table 13A compared to the expression level of the plurality of endogenous reference biomarkers indicates that the patient suffers from or is at risk of developing cardioembolic stroke;

wherein an increase or decrease of the expression level of the plurality of biomarkers selected from Table 14 compared to the expression level of the plurality of endogenous reference biomarkers indicates that the patient suffers from or is at risk of developing carotid stenosis;

wherein an increase or decrease of the expression level of the plurality of biomarkers selected from Table 15 compared to the expression level of the plurality of endogenous reference biomarkers indicates that the patient suffers from or is at risk of developing atrial fibrillation, thereby diagnosing the occurrence and cause of ischemic stroke or the predisposition for developing ischemic stroke. The levels of expression of the plurality of biomarkers can be concurrently or sequentially determined.

In a related aspect, the invention provides methods for diagnosing the occurrence and cause of ischemic stroke or a predisposition for developing ischemic stroke, the method comprising:

a) determining a level of expression of a plurality, e.g., at least 2, 3, 4, 5, 6, 7, 8, 9, 10, 11, 12, 13, 14, 15, or more or all, ischemic stroke-associated biomarkers in a biological sample from a patient, wherein the biomarkers are selected from the group consisting of a plurality of biomarkers selected from Table 7A, a plurality of biomarkers selected from Table 13A, a plurality of biomarkers selected from Table 14 and a plurality of biomarkers selected from Table 15;

b) comparing the level of expression of the ischemic stroke-associated biomarkers to a control expression level, wherein an increase or decrease of the expression level of the plurality of biomarkers selected from Table 7A compared to the control expression level indicates that the patient suffers from or is at risk of developing ischemic stroke;

wherein an increase or decrease of the expression level of the plurality of biomarkers selected from Table 13A compared to the control expression level indicates that the patient suffers from or is at risk of developing cardioembolic stroke;

wherein an increase or decrease of the expression level of the plurality of biomarkers selected from Table 14 compared to the control expression level indicates that the patient suffers from or is at risk of developing carotid stenosis;

wherein an increase or decrease of the expression level of the plurality of biomarkers selected from Table 15 compared to the control expression level indicates that the patient suffers from or is at risk of developing atrial fibrillation, thereby diagnosing the occurrence and cause of ischemic stroke or the predisposition for developing ischemic stroke. The levels of expression of the plurality of biomarkers can be concurrently or sequentially determined. The control expression level can be, e.g., with respect to a plurality of stably expressed endogenous reference biomarkers, with respect to the expression level of the same ischemia-associated biomarker in an otherwise healthy individual (optionally normalized to the expression levels of a plurality of stably expressed endogenous reference biomarkers), or with respect to a threshold level representative of the expression level of the same ischemia-associated biomarker in an otherwise healthy individual (optionally normalized to the expression levels of a plurality of stably expressed endogenous reference biomarkers).

In various embodiments, the plurality of biomarkers determined are from Table 7A. In various embodiments, the plurality of biomarkers determined are from Table 13A. In various embodiments, the plurality of biomarkers determined are from Table 14. In various embodiments, the plurality of biomarkers determined are from Table 15. In various embodiments, the plurality of biomarkers determined are from two or more of Table 7A, Table 13A, Table 14 and Table 15.

In some embodiments, the plurality of stably expressed endogenous reference biomarkers are selected from the biomarkers listed in Table 16. In some embodiments, the ischemic stroke-associated biomarkers are overexpressed or underexpressed at least about 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, or more, in comparison to the expression levels of a plurality of stably expressed endogenous reference biomarkers, e.g., those listed in Table 16. In some embodiments, the expression levels of 2, 3, 4, 5, 6, 7, 8, 9, 10, 15, 20, 25, 30, 35, or all, the endogenous reference biomarkers selected from the group consisting of USP7, MAPRE2, CSNK1G2, SAFB2, PRKAR2A, PI4 KB, CRTC1, HADHA, MAP1LC3B, KAT5, CDC2L1///CDC2L2, GTSE1, CDC2L1///CDC2L2, TCF25, CHP, LRRC40, hCG_2003956///LYPLA2///LYPLA2P1, DAXX, UBE2NL, EIF1, KCMF1, PRKRIP1, CHMP4A, TMEM184C, TINF2, PODNL1, FBXO42, LOC441258, RRP1, C10orf104, ZDHHC5, C9orf23, LRRC45, NACC1, LOC100133445///LOC115110, PEX16 are determined as a control.

In some embodiments, the level of expression of about 15-85, 20-70, 30-60 or 40-50 biomarkers are determined. In some embodiments, about 15, 20, 25, 30, 35, 40, 45, 50, 55, 60, 65, 70, 75, 80, 85, 90, 95 or 100 biomarkers are determined. In some embodiments, the expression levels of at least about 3, 5, 10, 15, 20, 25, 30 or more biomarkers from Table 7A are determined. In some embodiments, the expression levels of at least about 3, 5, 10, 15, 20, 25, 30 or more biomarkers from Table 13A are determined. In some embodiments, the expression levels of at least about 3, 5, 10, 15, 20, 25, 30 or more biomarkers from Table 14 are determined. In some embodiments, the expression levels of at least about 3, 5, 10, 15, 20, 25, 30 or more biomarkers from Table 15 are determined. In some embodiments, the level of expression of all biomarkers listed in Table 7A are determined. In some embodiments, the level of expression of all biomarkers listed in Table 13A are determined. In some embodiments, the level of expression of all biomarkers listed in Table 14 are determined. In some embodiments, the level of expression of all biomarkers listed in Table 15 are determined. Stroke-associated biomarkers with increased and/or decreased expression levels, e.g., in comparison to a control expression level, can be determined.

In some embodiments, the level of expression of biomarkers indicative of the occurrence of stroke is determined within 3 hours of a suspected ischemic event. In an otherwise healthy individual (i.e., no myocardial infarction, no vascular risk factors), an increased expression level of one or more or all ischemic stroke-associated biomarkers of Table 7A selected from the group consisting of FAT3, GADL1, CXADR, RNF141, CLEC4E, TIMP2, ANKRD28, TIMM8A, PTPRD, CCRL1, FCRL4, DLX6, GABRB2, GYPA, PHTF1, CKLF, CKLF, RRAGD, CLEC4E, CKLF, FGD4, CPEB2, LOC100290882, UBXN2B, ENTPD1, BST1, LTB4R, F5, IFRD1, KIAA0319, CHMP1B, MCTP1, VNN3, AMN1, LAMP2, FCHO2, ZNF608, REM2, QKI, RBM25, FAR2, ST3GAL6, HNRNPH2, GAB1, UBR5, VAPA, MCTP1 and SH3GL3 indicates that the patient suffers from or is at risk of developing ischemic stroke. In an otherwise healthy individual (i.e., no myocardial infarction, no vascular risk factors), a decreased expression level of one or more or all ischemic stroke-associated biomarkers of Table 7A selected from the group consisting of PGM5, CCDC144C///LOC100134159, LECT2, SHOX, TBX5, SPTLC3, SNIP, RBMS3, P704P, THSD4, SNRPN, GLYATL1, DKRZP434L187, OVOL2, SPIB, BXDC5, UNC5B, ASTN2, FLJ35934, CCDC144A, ALDOAP2, LDB3, LOC729222///PPFIBP1, HNRNPUL2, ELAVL2, PRTG, FOXA2, SCD5, LOC283027, LOC344595, RPL22, LOC100129488 and RPL22 indicates that the patient suffers from or is at risk of developing ischemic stroke.

In some embodiments, the level of expression of biomarkers indicative of the occurrence of stroke is determined within 3 hours of a suspected ischemic event. In an otherwise healthy individual (i.e., no myocardial infarction, no vascular risk factors), an increased expression level of 1, 2, 3, 4, 5, 6, 7, 8, 9, 10, 11, 12, 13, 14, 15, or more or all, ischemic stroke-associated biomarkers of Table 7A selected from the group consisting of FGD4, F5, ABCA1, LOC100290882, LTB4R, UBXN2B, CKLF, CLEC4E, PHTF1, ENTPD1, OSBPL1A, RRAGD, CPEB2, CKLF, BST1 and CKLF indicates that the patient suffers from or is at risk of developing ischemic stroke.

In various embodiments, in an individual presenting with myocardial infarction within 3 hours of a suspected ischemic event, an increased expression level of one or more or all ischemic stroke-associated biomarkers of Table 7A selected from the group consisting of CLEC4E, TIMP2, FGD4, CPEB2, LTB4R and VNN3 indicates that the individual suffers from or is at risk of developing ischemic stroke. In various embodiments, in an individual presenting with myocardial infarction within 3 hours of a suspected ischemic event, a decreased expression level of one or more or all ischemic stroke-associated biomarkers of Table 7A selected from the group consisting of PGM5, CCDC144C///LOC100134159, LECT2, SHOX, TBX5, SPTLC3, SNIP, RBMS3, P704P, THSD4, FAT3, SNRPN, GLYATL1, GADL1, CXADR, OVOL2, RNF141, SPIB, BXDC5, UNC5B, ASTN2, FLJ35934, ANKRD28, CCDC144A, TIMM8A, ALDOAP2, LDB3, PTPRD, LOC729222///PPFIBP1, CCRL1, HNRNPUL2, FCRL4, ELAVL2, PRTG, DLX6, FOXA2, SCD5, GABRB2, GYPA, PHTF1, CKLF, CKLF, RRAGD, CKLF, LOC100290882, UBXN2B, ENTPD1, BST1, F5, IFRD1, KIAA0319, CHMP1B, MCTP1, AMN1, LAMP2, FCHO2, ZNF608, REM2, QKI, RBM25, FAR2, ST3GAL6, HNRNPH2, GAB1, UBR5, VAPA, LOC283027, LOC344595, RPL22, LOC100129488, RPL22, MCTP1 and SH3GL3 indicates that the individual suffers from or is at risk of developing ischemic stroke.

In various embodiments, in an individual presenting with myocardial infarction within 3 hours of a suspected ischemic event, a decreased expression level of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more or all, ischemic stroke-associated biomarkers of Table 7A selected from the group consisting of THSD4, SNRPN, ASTN2, SNIP, FAT3, TIMM8A, CCDC144C///LOC100134159, ANKRD28, TBX5, PGM5, SCD5, FCRL4, SHOX, CCRL1, LECT2, PTPRD, CCDC144A, LDB3, LOC729222///PPFIBP1, RBMS3, P704P, GYPA, PRTG, GABRB2, HNRNPUL2, ELAVL2, SPTLC3, FOXA2, DLX6, ALDOAP2, and FLJ35934 indicates that the individual suffers from or is at risk of developing ischemic stroke. In various embodiments, in an individual presenting with myocardial infarction within 3 hours of a suspected ischemic event, a decreased expression level of 1, 2, 3, 4, 5, 6, 7, 8, 9 or 10, or more or all, ischemic stroke-associated biomarkers of Table 7A selected from the group consisting of THSD4, SNRPN, ASTN2, SNIP, FAT3, TIMM8A, CCDC144C///LOC100134159, ANKRD28, TBX5, PGM5 indicates that the individual suffers from or is at risk of developing ischemic stroke.

In various embodiments, in an individual presenting with one or more vascular risk factors (e.g., hypertension, diabetes mellitus, hyperlipidemia, or tobacco smoking) within 3 hours of a suspected ischemic event, an increased expression level of one or more or all ischemic stroke-associated biomarkers of Table 7A selected from the group consisting of RNF141, CLEC4E, TIMP2, PHTF1, CKLF, CKLF, RRAGD, CLEC4E, CKLF, FGD4, CPEB2, LOC100290882, UBXN2B, ENTPD1, BST1, LTB4R, F5, IFRD1, KIAA0319, CHMP1B, MCTP1, VNN3, AMN1, LAMP2, FCHO2, ZNF608, REM2, QKI, RBM25, FAR2, ST3GAL6, HNRNPH2, GAB1, UBR5, VAPA and MCTP1 indicates that the individual suffers from or is at risk of developing ischemic stroke. In various embodiments, in an individual presenting with one or more vascular risk factors within 3 hours of a suspected ischemic event, a decreased expression level of one or more or all ischemic stroke-associated biomarkers of Table 7A selected from the group consisting of PGM5, CCDC144C///LOC100134159, LECT2, SHOX, TBX5, SPTLC3, SNIP, RBMS3, P704P, THSD4, FAT3, SNRPN, GLYATL1, GADL1, CXADR, OVOL2, SPIB, BXDC5, UNC5B, ASTN2, FLJ35934, ANKRD28, CCDC144A, TIMM8A, ALDOAP2, LDB3, PTPRD, LOC729222///PPFIBP1, CCRL1, HNRNPUL2, FCRL4, ELAVL2, PRTG, DLX6, FOXA2, SCD5, GABRB2, GYPA, LOC283027, LOC344595, RPL22, LOC100129488, RPL22 and SH3GL3 indicates that the individual suffers from or is at risk of developing ischemic stroke.

In various embodiments, in an individual presenting with one or more vascular risk factors (e.g., hypertension, diabetes mellitus, hyperlipidemia, or tobacco smoking) within 3 hours of a suspected ischemic event, an increased expression level of 1, 2, 3 or 4 ischemic stroke-associated biomarkers of Table 7A selected from the group consisting of RNF141, ELL2, TIMP2 and CLEC4E indicates that the individual suffers from or is at risk of developing ischemic stroke. In various embodiments, in an individual presenting with one or more vascular risk factors within 3 hours of a suspected ischemic event, a decreased expression level of 1, 2, 3, 4, 5, 6, 7, 8, 9, 10, 11, 12, 13, 14, 15 or all, ischemic stroke-associated biomarkers of Table 7A selected from the group consisting of SNIP, BXDC5, FAT3, LECT2, THSD4, CCDC144C///LOC100134159, OVOL2, SPTLC3, GLYATL1, RBMS3, SPIB, DKFZP434L187, GADL1, SHOX, TBX5, UNC5B, PGM5 and CXADR indicates that the individual suffers from or is at risk of developing ischemic stroke.

In some embodiments, the level of expression of biomarkers indicative of the occurrence of stroke is determined 3 or more hours after a suspected ischemic event. In an otherwise healthy individual (i.e., no myocardial infarction, no vascular risk factors), an increased expression level of one or more or all ischemic stroke-associated biomarkers of Table 7A selected from the group consisting of PGM5, CCDC144C///LOC100134159, LECT2, SHOX, TBX5, SNIP, RBMS3, P704P, THSD4, FAT3, SNRPN, GLYATL1, GADL1, CXADR, OVOL2, RNF141, CLEC4E, BXDC5, UNC5B, TIMP2, ASTN2, FLJ35934, ANKRD28, CCDC144A, TIMM8A, ALDOAP2, LDB3, PTPRD, LOC729222///PPFIBP1, CCRL1, FCRL4, ELAVL2, PRTG, DLX6, SCD5, GABRB2, GYPA, PHTF1, CKLF, CKLF, RRAGD, CLEC4E, CKLF, FGD4, CPEB2, LOC100290882, UBXN2B, ENTPD1, BST1, LTB4R, F5, IFRD1, KIAA0319, CHMP1B, MCTP1, VNN3, AMN1, LAMP2, FCHO2, ZNF608, REM2, QKI, RBM25, FAR2, ST3GAL6, HNRNPH2, GAB1, UBR5, VAPA, LOC283027, LOC344595, RPL22, LOC100129488 and MCTP1 indicates that the patient suffers from or is at risk of developing ischemic stroke. In an otherwise healthy individual (i.e., no myocardial infarction, no vascular risk factors), a decreased expression level of one or more or all ischemic stroke-associated biomarkers of Table 7A selected from the group consisting of SPTLC3, DKRZP434L187, SPIB, HNRN-PUL2, FOXA2, RPL22 and SH3GL3 indicates that the patient suffers from or is at risk of developing ischemic stroke.

In some embodiments, the level of expression of biomarkers indicative of the occurrence of stroke is determined at least 24 hours after a suspected ischemic event. In an otherwise healthy individual (i.e., no myocardial infarction, no vascular risk factors), an increased expression level of 1, 2, 3, 4, 5, 6, 7, 8, 9, 10, 11, 12, 13, 14, 15, 16, 17, 18, 19 or 20 ischemic stroke-associated biomarkers of Table 7A selected from the group consisting of ZNF608, FCHO2, ST3GAL6, ABCA1, THBD, AMN1, QKI, KIAA0319, MCTP1, VNN3, UBR5, FAR2, RBM25, CHMP1B, LAMP2, VAPA, IFRD1, HNRNPH2, REM2 and GAB1 indicates that the patient suffers from or is at risk of developing ischemic stroke. In an otherwise healthy individual (i.e., no myocardial infarction, no vascular risk factors), an increased expression level of 1, 2, 3, 4, 5, 6, 7, 8, 9 or 10, or more or all, ischemic stroke-associated biomarkers of Table 7A selected from the group consisting of ZNF608, FCHO2, ST3GAL6, ABCA1, THBD, AMN1, QKI, KIAA0319, MCTP1 and VNN3 indicates that the patient suffers from or is at risk of developing ischemic stroke.

In various embodiments, in an individual presenting with myocardial infarction 3 or more hours after a suspected ischemic event, an increased expression level of one or more or all ischemic stroke-associated biomarkers of Table 7A selected from the group consisting of RNF141, CLEC4E, TIMP2, HNRNPUL2, PHTF1, CKLF, CKLF, RRAGD, CLEC4E, CKLF, FGD4, CPEB2, UBXN2B, BST1, LTB4R, F5, IFRD1, KIAA0319, MCTP1, VNN3, AMN1, LAMP2, ZNF608, FAR2, GAB1, VAPA and MCTP1 indicates that the individual suffers from or is at risk of developing ischemic stroke. In various embodiments, in an individual presenting with myocardial infarction 3 or more hours after a suspected ischemic event, a decreased expression level of one or more or all ischemic stroke-associated biomarkers of Table 7A selected from the group consisting of PGM5, CCDC144C///LOC100134159, LECT2, SHOX, TBX5, SPTLC3, SNIP, RBMS3, P704P, THSD4, FAT3, SNRPN, GLYATL1, GADL1, CXADR, OVOL2, SPIB, BXDC5, UNC5B, ASTN2, FLJ35934, ANKRD28, CCDC144A, TIMM8A, ALDOAP2, LDB3, PTPRD, LOC729222///PPFIBP1, CCRL1, FCRL4, ELAVL2, PRTG, DLX6, FOXA2, SCD5, GABRB2, GYPA, LOC100290882, ENTPD1, CHMP1B, FCHO2, LOC283027, REM2, QKI, RBM25, ST3GAL6, HNRNPH2, UBR5, LOC344595, RPL22, LOC100129488, RPL22 and SH3GL3 indicates that the individual suffers from or is at risk of developing ischemic stroke.

In various embodiments, in an individual presenting with myocardial infarction at least 24 hours after a suspected ischemic event, a decreased expression level of 1, 2, 3, 4, 5, 6, 7, or more or all, ischemic stroke-associated biomarkers of Table 7A selected from the group consisting of RPL22, LOC100129488, LOC283027, LOC344595, THSD4, FAT3, P704P indicates that the individual suffers from or is at risk of developing ischemic stroke.

In various embodiments, in an individual presenting with one or more vascular risk factors 3 or more hours after a suspected ischemic event, an increased expression level of one or more or all ischemic stroke-associated biomarkers of Table 7A selected from the group consisting of RNF141, CLEC4E, TIMP2, PHTF1, CKLF, CKLF, RRAGD, CLEC4E, CKLF, FGD4, CPEB2, LOC100290882, UBXN2B, ENTPD1, BST1, LTB4R, F5, IFRD1, KIAA0319, CHMP1B, MCTP1, VNN3, AMN1, LAMP2, FCHO2, ZNF608, REM2, QKI, RBM25, FAR2, ST3GAL6, HNRNPH2, GAB1, UBR5, VAPA and MCTP1 indicates that the individual suffers from or is at risk of developing ischemic stroke. In various embodiments, in an individual presenting with one or more vascular risk factors 3 or more hours after a suspected ischemic event, a decreased expression level of one or more or all ischemic stroke-associated biomarkers of Table 7A selected from the group consisting of PGM5, CCDC144C///LOC100134159, LECT2, SHOX, TBX5, SPTLC3, SNIP, RBMS3, P704P, THSD4, FAT3, SNRPN, GLYATL1, GADL1, CXADR, OVOL2, SPIB, BXDC5, UNC5B, ASTN2, FLJ35934, ANKRD28, CCDC144A, TIMM8A, ALDOAP2, LDB3, PTPRD, LOC729222///PPFIBP1, CCRL1, HNRNPUL2, FCRL4, ELAVL2, PRTG, DLX6, FOXA2, SCD5, GABRB2, GYPA, LOC283027, LOC344595, RPL22, LOC100129488, RPL22 and SH3GL3 indicates that the individual suffers from or is at risk of developing ischemic stroke.

In various embodiments, in an individual presenting with one or more vascular risk factors at least 24 hours after a suspected ischemic event, an increased expression level of one or both ischemic stroke-associated biomarkers of Table 7A selected from the group consisting of TIMP2 and MCTP1 indicates that the individual suffers from or is at risk of developing ischemic stroke. In various embodiments, in an individual presenting with one or more vascular risk factors at least 24 hours after a suspected ischemic event, a decreased expression level of 1, 2, 3, 4, 5, 6, or 7 ischemic stroke-associated biomarkers of Table 7A selected from the group consisting of RPL22, SNIP, SH3GL3, FAT3, SPTLC3, RBMS3 and SNRPN indicates that the individual suffers from or is at risk of developing ischemic stroke.

With respect to the determination of the cause of stroke, in some embodiments an increased expression level of one or more or all ischemic stroke-associated biomarkers of Table 13A selected from the group consisting of IRF6, ZNF254, GRM5, EXT2, AP3S2, PIK3C2B, ARHGEF5, COL13A1, PTPN20A///PTPN20B, LHFP, BANK1, HLA-DOA, EBF1, TMEM19, LHFP, FCRL1, OOEP and LRRC37A3 indicates that the patient has experienced or is at risk for cardioembolic stroke. In some embodiments, a decreased expression level of one or more or all ischemic stroke-associated biomarkers of Table 13A selected from the group consisting of LOC284751, CD46, ENPP2, C19orf28, TSKS, CHURC1, ADAMTSL4, FLJ40125, CLEC18A, ARHGEF12, C16orf68, TFDP1 and GSTK1 indicates that the patient has experienced or is at risk for cardioembolic stroke.

In some embodiments an increased expression level of 1, 2, 3, 4, 5, 6, 7, 8, 9, 10, 11, 12, 13, 14, 15, 16, 17, 18, 19 or 20 ischemic stroke-associated biomarkers of Table 13A selected from the group consisting of EBF1, GRM5, AP3S2, LRRC37A3, IRF6, LHFP, BANK1, ARHGEF5, ZNF254, COL13A1, P2RX5, LHFP, PIK3C2B, EXT2, HLA-DOA, OOEP, ZNF185, TMEM19, FCRL1 and PTPN20A/// PTPN20B indicates that the patient has experienced or is at risk for cardioembolic stroke. In some embodiments, a decreased expression level of 1, 2, 3, 4, 5, 6, 7, 8, 9, 10, 11, 12 or 13 ischemic stroke-associated biomarkers of Table 13A selected from the group consisting of TSKS, ENPP2, C16orf68, LOC284751, TFDP1, GSTK1, ADAMTSL4, CHURC1, FLJ40125, ARHGEF12, CLEC18A, CD46 and C19orf28 indicates that the patient has experienced or is at risk for cardioembolic stroke.

In some embodiments an increased expression level of 1, 2, 3, 4, 5, 6, 7, 8, 9, 10, or more or all, ischemic stroke-associated biomarkers of Table 13A selected from the group consisting of EBF1, GRM5, AP3S2, LRRC37A3, IRF6, LHFP, BANK1, ARHGEF5, ZNF254 and COL13A1 indicates that the patient has experienced or is at risk for cardioembolic stroke. In some embodiments, a decreased expression level of 1, 2, 3, 4, 5, 6, 7, 8, 9, 10, or more or all, ischemic stroke-associated biomarkers of Table 13A selected from the group consisting of TSKS, ENPP2, C16orf68, LOC284751, TFDP1, GSTK1, ADAMTSL4, CHURC1, FLJ40125 and ARHGEF12 indicates that the patient has experienced or is at risk for cardioembolic stroke.

With respect to the determination of the cause of stroke, in some embodiments, an increased expression level of one or more or all ischemic stroke-associated biomarkers of Table 14 selected from the group consisting of NT5E, CLASP2, GRM5, PROCR, ARHGEF5, AKR1C3, COL13A1, LHFP, RNF7, CYTH3, EBF1, RANBP10, PRSS35, C12orf42 and LOC100127980 indicates that the patient has experienced or is at risk for carotid stenosis. In some embodiments, a decreased expression level of one or more or all ischemic stroke-associated biomarkers of Table 14 selected from the group consisting of FLJ31945, LOC284751, LOC100271832, MTBP, ICAM4, SHOX2, DOPEY2, CMBL, LOC146880, SLC20A1, SLC6A19, ARHGEF12, C16orf68, GIPC2 and LOC100144603 indicates that the patient has experienced or is at risk for carotid stenosis.

With respect to the determination of the cause of stroke, in some embodiments, an increased expression level of 2, 5, 10, 15, or more or all, ischemic stroke-associated biomarkers of Table 14 selected from the group consisting of EBF1, COL13A1, LHFP, GRM5, ARHGEF5, RNF7, CLASP2, RANBP10, LOC100127980, CYTH3, PROCR, C12orf42, PRSS35, NT5E, and AKR1C3 indicates that the patient has experienced or is at risk for carotid stenosis. In some embodiments, a decreased expression level of 2, 5, 10, 15, or more or all ischemic stroke-associated biomarkers of Table 14 selected from the group consisting of FLJ31945, C16orf68, SLC20A1, DOPEY2, LOC284751, LOC100144603, MTBP, SHOX2, GIPC2, CMBL, LOC146880, SLC6A19, ICAM4, ARHGEF12, and LOC10027183 indicates that the patient has experienced or is at risk for carotid stenosis.

With respect to the determination of the cause of stroke, in some embodiments, an increased expression level of one or more or all ischemic stroke-associated biomarkers of Table 15 selected from the group consisting of SMC1A, SNORA68, GRLF1, SDC4, HIPK2, LOC100129034, CMTM1 and TTC7A indicates that the patient has experienced or is at risk for atrial fibrillation. In some embodiments, a decreased expression level of one or more or all ischemic stroke-associated biomarkers of Table 15 selected from the group consisting of LRRC43, MIF///SLC2A11, PER3, PPIE, COL13A1, DUSP16, LOC100129034, BRUNOL6, GPR176, C6orf164 and MAP3K7IP1 indicates that the patient has experienced or is at risk for atrial fibrillation.

With respect to the determination of the cause of stroke, in some embodiments, an increased expression level of 1, 2, 3, 4, 5, 6, 7 or 8 ischemic stroke-associated biomarkers of Table 15 selected from the group consisting of CMTM1, SDC4, SNORA68, HIPK2, TTC7A, GRLF1, LOC100129034, SMC1A indicates that the patient has experienced or is at risk for atrial fibrillation. In some embodiments, a decreased expression level of 1, 2, 3, 4, 5, 6, 7, 8, 9 or 10 ischemic stroke-associated biomarkers of Table 15 selected from the group consisting of COL13A1, C6orf164, GPR176, BRUNOL6, MIF///SLC2A11, DUSP16, PPIE, MAP3K7IP1, PER3, LRRC43 indicates that the patient has experienced or is at risk for atrial fibrillation.

In a related aspect, the invention provides methods for determining whether a stroke has occurred or predicting whether a stroke will occur. Accordingly, the invention provides methods for diagnosing ischemic stroke or a predisposition for developing ischemic stroke, the method comprising: determining a level of expression of a plurality of ischemic stroke-associated biomarkers in a biological sample from a patient, wherein an increase or decrease of the level compared to a control indicates that the patient suffers from or is at risk of developing ischemic stroke, wherein the plurality of ischemic stroke-associated biomarkers is selected from the biomarkers set forth in Table 7A. In some embodiments, the methods for determining the occurrence of stroke comprise further determining the level of expression of one or biomarkers listed in Table 7B. In some embodiments, the ischemic stroke is a member selected from the group consisting of: embolic stroke, thrombotic stroke, transient ischemic attack, cardioembolic stroke and atherothrombotic stroke.

In some embodiments, the level of expression of biomarkers indicative of the occurrence of stroke is determined within 3 hours of a suspected ischemic event. In an otherwise healthy individual (i.e., no myocardial infarction, no vascular risk factors), an increased expression level of one or more or all ischemic stroke-associated biomarkers of Table 7A selected from the group consisting of FAT3, GADL1, CXADR, RNF141, CLEC4E, TIMP2, ANKRD28, TIMM8A, PTPRD, CCRL1, FCRL4, DLX6, GABRB2, GYPA, PHTF1, CKLF, CKLF, RRAGD, CLEC4E, CKLF, FGD4, CPEB2, LOC100290882, UBXN2B, ENTPD1, BST1, LTB4R, F5, IFRD1, KIAA0319, CHMP1B, MCTP1, VNN3, AMN1, LAMP2, FCHO2, ZNF608, REM2, QKI, RBM25, FAR2, ST3GAL6, HNRNPH2, GAB1, UBR5, VAPA, MCTP1 and SH3GL3 indicates that the patient suffers from or is at risk of developing ischemic stroke. In an otherwise healthy individual (i.e., no myocardial infarction, no vascular risk factors), a decreased expression level of one or more or all ischemic stroke-associated biomarkers of Table 7A selected from the group consisting of PGM5, CCDC144C///LOC100134159, LECT2, SHOX, TBX5, SPTLC3, SNIP, RBMS3, P704P, THSD4, SNRPN, GLYATL1, DKRZP434L187, OVOL2, SPIB, BXDC5, UNC5B, ASTN2, FLJ35934, CCDC144A, ALDOAP2, LDB3, LOC729222///PPFIBP1, HNRNPUL2, ELAVL2, PRTG, FOXA2, SCD5, LOC283027, LOC344595, RPL22, LOC100129488 and RPL22 indicates that the patient suffers from or is at risk of developing ischemic stroke.

In various embodiments, in an individual presenting with myocardial infarction within 3 hours of a suspected ischemic event, an increased expression level of one or more or all ischemic stroke-associated biomarkers of Table 7A selected from the group consisting of CLEC4E, TIMP2, FGD4, CPEB2, LTB4R and VNN3 indicates that the individual suffers from or is at risk of developing ischemic stroke. In various embodiments, in an individual presenting with myocardial infarction within 3 hours of a suspected ischemic event, a decreased expression level of one or more or all ischemic stroke-associated biomarkers of Table 7A selected from the group consisting of PGM5, CCDC144C///LOC100134159, LECT2, SHOX, TBX5, SPTLC3, SNIP, RBMS3, P704P, THSD4, FAT3, SNRPN, GLYATL1, GADL1, CXADR, OVOL2, RNF141, SPIB, BXDC5, UNC5B, ASTN2, FLJ35934, ANKRD28, CCDC144A, TIMM8A, ALDOAP2, LDB3, PTPRD, LOC729222///PPFIBP1, CCRL1, HNRNPUL2, FCRL4, ELAVL2, PRTG, DLX6, FOXA2, SCD5, GABRB2, GYPA, PHTF1, CKLF, CKLF, RRAGD, CKLF, LOC100290882, UBXN2B, ENTPD1, BST1, F5, IFRD1, KIAA0319, CHMP1B, MCTP1, AMN1, LAMP2, FCHO2, ZNF608, REM2, QKI, RBM25, FAR2, ST3GAL6, HNRNPH2, GAB1, UBR5, VAPA, LOC283027, LOC344595, RPL22, LOC100129488, RPL22, MCTP1 and SH3GL3 indicates that the individual suffers from or is at risk of developing ischemic stroke.

In various embodiments, in an individual presenting with one or more vascular risk factors (e.g., hypertension, diabetes mellitus, hyperlipidemia, or tobacco smoking) within 3 hours of a suspected ischemic event, an increased expression level of one or more or all ischemic stroke-associated biomarkers of Table 7A selected from the group consisting of RNF141, CLEC4E, TIMP2, PHTF1, CKLF, CKLF, RRAGD, CLEC4E, CKLF, FGD4, CPEB2, LOC100290882, UBXN2B, ENTPD1, BST1, LTB4R, F5, IFRD1, KIAA0319, CHMP1B, MCTP1, VNN3, AMN1, LAMP2, FCHO2, ZNF608, REM2, QKI, RBM25, FAR2, ST3GAL6, HNRNPH2, GAB1, UBR5, VAPA and MCTP1 indicates that the individual suffers from or is at risk of developing ischemic stroke. In various embodiments, in an individual presenting with one or more vascular risk factors within 3 hours of a suspected ischemic event, a decreased expression level of one or more or all ischemic stroke-associated biomarkers of Table 7A selected from the group consisting of PGM5, CCDC144C///LOC100134159, LECT2, SHOX, TBX5, SPTLC3, SNIP, RBMS3, P704P, THSD4, FAT3, SNRPN, GLYATL1, GADL1, CXADR, OVOL2, SPIB, BXDC5, UNC5B, ASTN2, FLJ35934, ANKRD28, CCDC144A, TIMM8A, ALDOAP2, LDB3, PTPRD, LOC729222///PPFIBP1, CCRL1, HNRNPUL2, FCRL4, ELAVL2, PRTG, DLX6, FOXA2, SCD5, GABRB2, GYPA, LOC283027, LOC344595, RPL22, LOC100129488, RPL22 and SH3GL3 indicates that the individual suffers from or is at risk of developing ischemic stroke.

In some embodiments, the level of expression of biomarkers indicative of the occurrence of stroke is determined 3 or more hours after a suspected ischemic event. In an otherwise healthy individual (i.e., no myocardial infarction, no vascular risk factors), an increased expression level of one or more or all ischemic stroke-associated biomarkers of Table 7A selected from the group consisting of PGM5, CCDC144C///LOC100134159, LECT2, SHOX, TBX5, SNIP, RBMS3, P704P, THSD4, FAT3, SNRPN, GLYATL1, GADL1, CXADR, OVOL2, RNF141, CLEC4E, BXDC5, UNC5B, TIMP2, ASTN2, FLJ35934, ANKRD28, CCDC144A, TIMM8A, ALDOAP2, LDB3, PTPRD, LOC729222///PPFIBP1, CCRL1, FCRL4, ELAVL2, PRTG, DLX6, SCD5, GABRB2, GYPA, PHTF1, CKLF, CKLF, RRAGD, CLEC4E, CKLF, FGD4, CPEB2, LOC100290882, UBXN2B, ENTPD1, BST1, LTB4R, F5, IFRD1, KIAA0319, CHMP1B, MCTP1, VNN3, AMN1, LAMP2, FCHO2, ZNF608, REM2, QKI, RBM25, FAR2, ST3GAL6, HNRNPH2, GAB1, UBR5, VAPA, LOC283027, LOC344595, RPL22, LOC100129488 and MCTP1 indicates that the patient suffers from or is at risk of developing ischemic stroke. In an otherwise healthy individual (i.e., no myocardial infarction, no vascular risk factors), a decreased expression level of one or more or all ischemic stroke-associated biomarkers of Table 7A selected from the group consisting of SPTLC3, DKRZP434L187, SPIB, HNRNPUL2, FOXA2, RPL22 and SH3GL3 indicates that the patient suffers from or is at risk of developing ischemic stroke.

In various embodiments, in an individual presenting with myocardial infarction 3 or more hours after a suspected ischemic event, an increased expression level of one or more or all ischemic stroke-associated biomarkers of Table 7A selected from the group consisting of RNF141, CLEC4E, TIMP2, HNRNPUL2, PHTF1, CKLF, CKLF, RRAGD, CLEC4E, CKLF, FGD4, CPEB2, UBXN2B, BST1, LTB4R, F5, IFRD1, KIAA0319, MCTP1, VNN3, AMN1, LAMP2, ZNF608, FAR2, GAB1, VAPA and MCTP1 indicates that the individual suffers from or is at risk of developing ischemic stroke. In various embodiments, in an individual presenting with myocardial infarction 3 or more hours after a suspected ischemic event, a decreased expression level of one or more or all ischemic stroke-associated biomarkers of Table 7A selected from the group consisting of PGM5, CCDC144C///LOC100134159, LECT2, SHOX, TBX5, SPTLC3, SNIP, RBMS3, P704P, THSD4, FAT3, SNRPN, GLYATL1, GADL1, CXADR, OVOL2, SPIB, BXDC5, UNC5B, ASTN2, FLJ35934, ANKRD28, CCDC144A, TIMM8A, ALDOAP2, LDB3, PTPRD, LOC729222///PPFIBP1, CCRL1, FCRL4, ELAVL2, PRTG, DLX6, FOXA2, SCD5, GABRB2, GYPA, LOC100290882, ENTPD1, CHMP1B, FCHO2, LOC283027, REM2, QKI, RBM25, ST3GAL6, HNRNPH2, UBR5, LOC344595, RPL22, LOC100129488, RPL22 and SH3GL3 indicates that the individual suffers from or is at risk of developing ischemic stroke.

In various embodiments, in an individual presenting with one or more vascular risk factors 3 or more hours after a suspected ischemic event, an increased expression level of one or more or all ischemic stroke-associated biomarkers of Table 7A selected from the group consisting of RNF141, CLEC4E, TIMP2, PHTF1, CKLF, CKLF, RRAGD, CLEC4E, CKLF, FGD4, CPEB2, LOC100290882, UBXN2B, ENTPD1, BST1, LTB4R, F5, IFRD1, KIAA0319, CHMP1B, MCTP1, VNN3, AMN1, LAMP2, FCHO2, ZNF608, REM2, QKI, RBM25, FAR2, ST3GAL6, HNRNPH2, GAB1, UBR5, VAPA and MCTP1 indicates that the individual suffers from or is at risk of developing ischemic stroke. In various embodiments, in an individual presenting with one or more vascular risk factors 3 or more hours after a suspected ischemic event, a decreased expression level of one or more or all ischemic stroke-associated biomarkers of Table 7A selected from the group consisting of PGM5, CCDC144C///LOC100134159, LECT2, SHOX, TBX5, SPTLC3, SNIP, RBMS3, P704P, THSD4, FAT3, SNRPN, GLYATL1, GADL1, CXADR, OVOL2, SPIB, BXDC5, UNC5B, ASTN2, FLJ35934, ANKRD28, CCDC144A, TIMM8A, ALDOAP2, LDB3, PTPRD, LOC729222///PPFIBP1, CCRL1, HNRNPUL2, FCRL4, ELAVL2, PRTG, DLX6, FOXA2, SCD5, GABRB2, GYPA, LOC283027, LOC344595, RPL22, LOC100129488, RPL22 and SH3GL3 indicates that the individual suffers from or is at risk of developing ischemic stroke.

In a further aspect, the invention provides methods for determining the occurrence of or the predisposition of a subject to experience cardioembolic stroke, the method comprising: determining a level of expression of a plurality of ischemic stroke-associated biomarkers in a biological sample from a patient, wherein an increase or decrease of the level compared to a control indicates that the patient has experienced cardioembolic stroke, wherein the plurality of ischemic stroke-associated biomarkers is selected from the biomarkers set forth in Table 13A. In some embodiments, an increased expression level of one or more or all ischemic stroke-associated biomarkers selected from the group consisting of IRF6, ZNF254, GRM5, EXT2, AP3S2, PIK3C2B, ARHGEF5, COL13A1, PTPN20A///PTPN20B, LHFP, BANK1, HLA-DOA, EBF1, TMEM19, LHFP, FCRL1, OOEP and LRRC37A3 indicates that the patient has experienced or is at risk for cardioembolic stroke. In some embodiments, a decreased expression level of one or more or all ischemic stroke-associated biomarkers selected from the group consisting of LOC284751, CD46, ENPP2, C19orf28, TSKS, CHURC1, ADAMTSL4, FLJ40125, CLEC18A, ARHGEF12, C16orf68, TFDP1 and GSTK1 indicates that the patient has experienced or is at risk for cardioembolic stroke. In some embodiments, a level of expression of a plurality of ischemic stroke-associated biomarkers listed in Table 13B is further determined, wherein an increase or decrease of the level compared to a control indicates that the patient has experienced or is at risk for cardioembolic stroke. In some embodiments an increased expression level of 1, 2, 3, 4, 5, 6, 7, 8, 9, 10, or more or all, ischemic stroke-associated biomarkers of Table 13A selected from the group consisting of EBF1, GRM5, AP3S2, LRRC37A3, IRF6, LHFP, BANK1, ARHGEF5, ZNF254 and COL13A1 indicates that the patient has experienced or is at risk for cardioembolic stroke. In some embodiments, a decreased expression level of 1, 2, 3, 4, 5, 6, 7, 8, 9, 10, or more or all, ischemic stroke-associated biomarkers of Table 13A selected from the group consisting of TSKS, ENPP2, C16orf68, LOC284751, TFDP1, GSTK1, ADAMTSL4, CHURC1, FLJ40125 and ARHGEF12 indicates that the patient has experienced or is at risk for cardioembolic stroke.

In a further aspect, the invention provides methods for determining the occurrence of or the predisposition of a subject to experience carotid stenosis, the method comprising: determining a level of expression of a plurality of ischemic stroke-associated biomarkers in a biological sample from a patient who has suffered ischemic stroke, wherein an increase or decrease of the level compared to a control indicates that the patient has experienced carotid stenosis, wherein the plurality of ischemic stroke-associated biomarkers is selected from the biomarkers set forth in Table 14. In some embodiments, an increased expression level of one or more or all ischemic stroke-associated biomarkers selected from the group consisting of NT5E, CLASP2, GRM5, PROCR, ARHGEF5, AKR1C3, COL13A1, LHFP, RNF7, CYTH3, EBF1, RANBP10, PRSS35, C12orf42 and LOC100127980 indicates that the patient has experienced or is at risk for carotid stenosis. In some embodiments, a decreased expression level of one or more or all ischemic stroke-associated biomarkers selected from the group consisting of FLJ31945, LOC284751, LOC100271832, MTBP, ICAM4, SHOX2, DOPEY2, CMBL, LOC146880, SLC20A1, SLC6A19, ARHGEF12, C16orf68, GIPC2 and LOC100144603 indicates that the patient has experienced or is at risk for carotid stenosis. In some embodiments, an increased expression level of 2, 5, 10, 15, or more or all, ischemic stroke-associated biomarkers of Table 14 selected from the group consisting of EBF1, COL13A1, LHFP, GRM5, ARHGEF5, RNF7, CLASP2, RANBP10, LOC100127980, CYTH3, PROCR, C12orf42, PRSS35, NT5E, and AKR1C3 indicates that the patient has experienced or is at risk for carotid stenosis. In some embodiments, a decreased expression level of 2, 5, 10, 15, or more or all ischemic stroke-associated biomarkers of Table 14 selected from the group consisting of FLJ31945, C16orf68, SLC20A1, DOPEY2, LOC284751, LOC100144603, MTBP, SHOX2, GIPC2, CMBL, LOC146880, SLC6A19, ICAM4, ARHGEF12, and LOC10027183 indicates that the patient has experienced or is at risk for carotid stenosis.

In a further aspect, the invention provides methods for determining the occurrence of or the predisposition of a subject to experience atrial fibrillation in a patient, the method comprising: determining a level of expression of a plurality of ischemic stroke-associated biomarkers in a biological sample from the patient, wherein an increase or decrease of the level compared to a control indicates that the patient has experienced or is at risk for experiencing atrial fibrillation, wherein the plurality of ischemic stroke-associated biomarkers is selected from the biomarkers set forth in Table 15. In some embodiments, an increased expression level of one or more or all ischemic stroke-associated biomarkers selected from the group consisting of SMC1A, SNORA68, GRLF1, SDC4, HIPK2, LOC100129034, CMTM1 and TTC7A indicates that the patient has experienced or is at risk for atrial fibrillation. In some embodiments, a decreased expression level of one or more or all ischemic stroke-associated biomarkers selected from the group consisting of LRRC43, MIF///SLC2A11, PER3, PPIE, COL13A1, DUSP16, LOC100129034, BRUNOL6, GPR176, C6orf164 and MAP3K7IP1 indicates that the patient has experienced or is at risk for atrial fibrillation. In some embodiments, an increased expression level of 1, 2, 3, 4, 5, 6, 7 or 8 ischemic stroke-associated biomarkers of Table 15 selected from the group consisting of CMTM1, SDC4, SNORA68, HIPK2, TTC7A, GRLF1, LOC100129034, SMC1A indicates that the patient has experienced or is at risk for atrial fibrillation. In some embodiments, a decreased expression level of 1, 2, 3, 4, 5, 6, 7, 8, 9 or 10 ischemic stroke-associated biomarkers of Table 15 selected from the group consisting of COL13A1, C6orf164, GPR176, BRUNOL6, MIF///SLC2A11, DUSP16, PPIE, MAP3K7IP1, PER3, LRRC43 indicates that the patient has experienced or is at risk for atrial fibrillation.

With respect to embodiments of the methods for determination of occurrence and/or cause of stroke, in some embodiments, the level of expression of about 15-85, 20-70, 30-60 or 40-50 total biomarkers are determined. In some embodiments, about 15, 20, 25, 30, 35, 40, 45, 50, 55, 60, 65, 70, 75, 80, 85, 90, 95 or 100 biomarkers are determined. The levels of expression of the plurality of biomarkers can be concurrently or sequentially determined.

In some embodiments, the control level is the expression level of a plurality of stably expressed endogenous reference biomarkers. In some embodiments, the plurality of stably expressed endogenous reference biomarkers are selected from the biomarkers listed in Table 16. In some embodiments, the ischemic stroke-associated biomarkers are overexpressed or underexpressed at least about 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, or more, in comparison to the expression levels of a plurality of stably expressed endogenous reference biomarkers, e.g., those listed in Table 16. In some embodiments, the expression levels of 2, 3, 4, 5, 6, 7, 8, 9, 10, 15, 20, 25, 30, 35, or all, the endogenous reference biomarkers selected from the group consisting of USP7, MAPRE2, CSNK1G2, SAFB2, PRKAR2A, PI4 KB, CRTC1, HADHA, MAP1LC3B, KAT5, CDC2L1///CDC2L2, GTSE1, CDC2L1///CDC2L2, TCF25, CHP, LRRC40, hCG_2003956///LYPLA2///LYPLA2P1, DAXX, UBE2NL, EIF1, KCMF1, PRKRIP1, CHMP4A, TMEM184C, TINF2, PODNL1, FBXO42, LOC441258, RRP1, C10orf104, ZDHHC5, C9orf23, LRRC45, NACC1, LOC100133445///LOC115110, PEX16 are determined as a control.

In some embodiments, the control level is the expression level of the same biomarker in a healthy individual, e.g. an individual who has not experienced a vascular event and/or who is not at risk of experiencing a vascular event (e.g., TIA, ischemic stroke, myocardial infarction, peripheral vascular disease, or venous thromboembolism). In some embodiments, the control is a threshold level of expression, e.g., of the same ischemic stoke-associated biomarker, optionally normalized to the expression level of a stably expressed endogenous reference biomarker, representative of a population of healthy individuals.

Methods for determining the occurrence or predisposition of an ischemic event, may further comprise the step of determining whether the patient has suffered a myocardial infarction or whether the patient has vascular risk factors.

In some embodiments, the patient is asymptomatic. In some embodiments, the patient is exhibiting symptoms of ischemic stroke, e.g., of having experienced an ischemic event, of experiencing an ischemic event, or of an imminent ischemic event. In some embodiments, the patient has suffered an ischemic event. In some embodiments, the determining step is performed at 3 or fewer hours after the ischemic event. In some embodiments, the determining step is performed 3 or more hours after the ischemic event.

In some embodiments, the methods further comprise the step of recommending or providing a regime of treatment to the patient appropriate to the determined cause of stroke. For example, in patients diagnosed as experiencing or having a predisposition for experiencing cardioembolic stroke, the methods further provide for recommending or providing a regime of treatment or prevention for cardioembolic stroke. In patients diagnosed as experiencing or having a predisposition for experiencing carotid stenosis, the methods further provide for recommending or providing a regime of treatment or prevention for carotid stenosis. In patients diagnosed as experiencing or having a predisposition for experiencing atrial fibrillation, the methods further provide for recommending or providing a regime of treatment or prevention for atrial fibrillation.

With respect to embodiments for determination of the level of expression of the biomarkers, in some embodiments, the level of expression of the biomarker is determined at the transcriptional level. For example, in some embodiments, the level of expression is determined by detecting hybridization of an ischemic stroke-associated gene probe to gene transcripts of the biomarkers in the biological sample. In some embodiments, the hybridization step is performed on a nucleic acid array chip. In some embodiments, the hybridization step is performed in a microfluidics assay plate. In some embodiments, the level of expression is determined by amplification of gene transcripts of the biomarkers. In some embodiments, the amplification reaction is a polymerase chain reaction (PCR).

In some embodiments, the level of expression of the biomarker is determined at the protein level.

In some embodiments, the methods further comprise obtaining a biological sample from the patient. In some embodiments, the biological sample is blood, serum or plasma.

In a further aspect, the invention provides a solid support comprising a plurality of nucleic acids that hybridize to a plurality of the genes set forth in Tables 7A, 7B, 13A, 13B, 14 and 15 (and optionally Table 16), wherein the plurality of nucleic acids are attached to the solid support. The solid support may optionally comprise a plurality of nucleic acids that hybridize to a plurality of the genes set forth in Table 16. In various embodiments, the solid support is a microarray. In various embodiments, the solid support is attached to at least about 15, 20, 25, 30, 35, 40, 45, 50, 55, 60, 75, 80, 85, 90, 95 or 100, or more or all, genes set forth in Tables 7A, 7B, 13A, 13B, 14, 15 and/or 16.

In one embodiment, the solid support comprises a plurality of nucleic acids that hybridize to a plurality of the genes listed in Table 7A (and 7B). For example, in one embodiment, the solid support comprises 2, 5, 10, 15, 20, or more or all, nucleic acids that hybridize to a plurality of stroke-associated biomarkers selected from SNIP, BXDC5, FAT3, LECT2, THSD4, CCDC144C///LOC100134159, OVOL2, SPTLC3, CLEC4E, GLYATL1, RBMS3, SPIB, DKFZP434L187, GADL1, SHOX, TBX5, UNC5B, PGM5, TIMP2, ELL2, CXADR, and RNF141. In one embodiment, the solid support comprises 2, 3, 4, 5, 6, 7, 8, or 9, nucleic acids that hybridize to a plurality of stroke-associated biomarkers selected from RPL22, SNIP, SH3GL3, MCTP1, FAT3, SPTLC3, RBMS3, SNRPN, and TIMP2. In one embodiment, the solid support comprises 2, 5, 10, 15, or more or all, nucleic acids that hybridize to a plurality of stroke-associated biomarkers selected from FGD4, F5, ABCA1, LOC100290882, LTB4R, UBXN2B, CKLF, CLEC4E, PHTF1, ENTPD1, OSBPL1A, RRAGD, CPEB2, CKLF, BST1, and CKLF. In one embodiment, the solid support comprises 2, 5, 10, 15, 20, or more or all, nucleic acids that hybridize to a plurality of stroke-associated biomarkers selected from ZNF608, FCHO2, ST3GAL6, ABCA1, THBD, AMN1, QKI, KIAA0319, MCTP1, VNN3, UBR5, FAR2, RBM25, CHMP1B, LAMP2, VAPA, IFRD1, HNRNPH2, REM2, and GAB1. In one embodiment, the solid support comprises 2, 5, 10, 15, 20, 25, 30, or more or all, nucleic acids that hybridize to a plurality of stroke-associated biomarkers selected from THSD4, SNRPN, ASTN2, SNIP, FAT3, TIMM8A, CCDC144C///LOC100134159, ANKRD28, TBX5, PGM5, SCD5, FCRL4, SHOX, CCRL1, LECT2, PTPRD, CCDC144A, LDB3, LOC729222///PPFIBP1, RBMS3, P704P, GYPA, PRTG, GABRB2, HNRNPUL2, ELAVL2, SPTLC3, FOXA2, DLX6, ALDOAP2, and FLJ35934. In one embodiment, the solid support comprises 2, 5, 6, 7, or more or all, nucleic acids that hybridize to a plurality of stroke-associated biomarkers selected from RPL22, LOC100129488, LOC283027, LOC344595, THSD4, FAT3, and P704P. In one embodiment, the solid support comprises 15, 20, 25, 30, 35, 40, 50, 55, 60, 65, 70, 75, 80, 85, 90, 95, 100 or more or all, nucleic acids that hybridize to a plurality of stroke-associated biomarkers selected from SNIP, BXDC5, FAT3, LECT2, THSD4, CCDC144C///LOC100134159, OVOL2, SPTLC3, CLEC4E, GLYATL1, RBMS3, SPIB, DKFZP434L187, GADL1, SHOX, TBX5, UNC5B, PGM5, TIMP2, ELL2, CXADR, RNF141, RPL22, SH3GL3, MCTP1, SNRPN, FGD4, F5, ABCA1, LOC100290882, LTB4R, UBXN2B, CKLF, PHTF1, ENTPD1, OSBPL1A, RRAGD, CPEB2, CKLF, BST1, ZNF608, FCHO2, ST3GAL6, THBD, AMN1, QKI, KIAA0319, MCTP1, VNN3, UBR5, FAR2, RBM25, CHMP1B, LAMP2, VAPA, IFRD1, HNRNPH2, REM2, GAB1, ASTN2, TIMM8A, CCDC144C///LOC100134159, ANKRD28, SCD5, FCRL4, CCRL1, LECT2, PTPRD, CCDC144A, LDB3, LOC729222///PPFIBP1, P704P, GYPA, PRTG, GABRB2, HNRNPUL2, ELAVL2, FOXA2, DLX6, ALDOAP2, FLJ35934, LOC100129488, LOC283027, and LOC344595.

In one embodiment, the solid support comprises a plurality of nucleic acids that hybridize to a plurality of the genes listed in Table 13A (and 13B). In one embodiment, the solid support comprises 2, 5, 10, 15, 20, 25, 30, 35, or more or all, nucleic acids that hybridize to a plurality of cardioembolic stroke-associated biomarkers selected from EBF1, GRM5, TSKS, ENPP2, AP3S2, LRRC37A3, C16orf68, LOC284751, IRF6, LHFP, BANK1, ARHGEF5, ZNF254, TFDP1, COL13A1, GSTK1, ADAMTSL4, P2RX5, LHFP, PIK3C2B, CHURC1, EXT2, HLA-DOA, OOEP, ZNF185, TMEM19, FCRL1, FLJ40125, ARHGEF12, CLEC18A, CD46, PTPN20A///PTPN20B, and C19orf28.

In one embodiment, the solid support comprises a plurality of nucleic acids that hybridize to a plurality of the genes listed in Table 14. In one embodiment, the solid support comprises 2, 5, 10, 15, 20, 25, 30, 35, or more or all, nucleic acids that hybridize to a plurality of atrial fibrillation stroke-associated biomarkers selected from EBF1, FLJ31945, C16orf68, SLC20A1, DOPEY2, COL13A1, LHFP, LOC284751, GRM5, LOC100144603, MTBP, SHOX2, ARHGEF5, RNF7, CLASP2, GIPC2, RANBP10, CMBL, LOC100127980, CYTH3, PROCR, LOC146880, SLC6A19, ICAM4, C12orf42, ARHGEF12, PRSS35, NT5E, LOC100271832, LHFP, NT5E and AKR1C3.

In one embodiment, the solid support comprises a plurality of nucleic acids that hybridize to a plurality of the genes listed in Table 15. In one embodiment, the solid support comprises 2, 5, 10, 15, 18, or more or all, nucleic acids that hybridize to a plurality of atrial fibrillation stroke-associated biomarkers selected from CMTM1, COL13A1, SDC4, C6orf164, GPR176, BRUNOL6, SNORA68, MIF/// SLC2A11, DUSP16, HIPK2, TTC7A, PPIE, GRLF1, MAP3K7IP1, LOC100129034, PER3, SMC1A, and LRRC43.

In various embodiments, the solid support further comprises a plurality of nucleic acids that hybridize to a plurality of endogenous reference genes selected from the group consisting of USP7, MAPRE2, CSNK1G2, SAFB2, PRKAR2A, PI4 KB, CRTC1, HADHA, MAP1LC3B, KAT5, CDC2L1///CDC2L2, GTSE1, TCF25, CHP, LRRC40, hCG_2003956///LYPLA2///LYPLA2P1, DAXX, UBE2NL, EIF1, KCMF1, PRKRIP1, CHMP4A, TMEM184C, TINF2, PODNL1, FBXO42, LOC441258, RRP1, C10orf104, ZDHHC5, C9orf23, LRRC45, NACC1, LOC100133445///LOC115110, PEX16.

DEFINITIONS

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 3rd ed. (2001) Cold Spring Harbor Laboratory Press, Cold Spring Harbor, N.Y. and Ausubel, et al., CURRENT PROTOCOLS IN MOLECULAR BIOLOGY, 1990-2008, Wiley Interscience), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

"Ischemia" or "ischemic event" as used herein refers to diseases and disorders characterized by inadequate blood supply (i.e., circulation) to a local area due to blockage of the blood vessels to the area. Ischemia includes for example, strokes and transient ischemic attacks. Strokes include, e.g., ischemic stroke (including, but not limited to, cardioembolic strokes, atheroembolic or atherothrombotic strokes, i.e., strokes caused by atherosclerosis in the carotid, aorta, heart, and brain, small vessel strokes (i.e., lacunar strokes), strokes caused by diseases of the vessel wall, i.e., vasculitis, strokes caused by infection, strokes caused by hematological disorders, strokes caused by migraines, and strokes caused by medications such as hormone therapy), hemorrhagic ischemic stroke, intracerebral hemorrhage, and subarachnoid hemorrhage.

"Ischemia reference expression profile" refers to the pattern of expression of a set of genes (e.g., a plurality of the genes set forth in Tables 7A, 7B, 13A, 13B, 14 and 15) differentially expressed (i.e., overexpressed or underexpressed) in ischemia relative to a control (e.g., the expression level in an individual free of an ischemic event or the expression level of a stably expressed endogenous reference biomarker). A gene from Tables 7A, 7B, 13A, 13B, 14 and 15 that is expressed at a level that is at least about 1.2-, 1.3-, 1.4-, 1.5-, 1.6-, 1.7-, 1.8-, 1.9-, 2.0-, 2.1-, 2.2-, 2.3-, 2.4-, 2.5-, 2.6-, 2.7-, 2.8-, 2.9-, 3.0-, 3.1-, 3.2-, 3.3-, 3.4- or 3.5-fold higher than the level in a control is a gene overexpressed in ischemia and a gene from Tables 7A, 7B, 13A, 13B, 14 and 15 that is expressed at a level that is at least about 1.2-, 1.3-, 1.4-, 1.5-, 1.6-, 1.7-, 1.8-, 1.9-, 2.0-, 2.1-, 2.2-, 2.3-, 2.4-, 2.5-, 2.6-, 2.7-, 2.8-, 2.9-, 3.0-, 3.1-, 3.2-, 3.3-, 3.4- or 3.5-fold lower than the level in a control is a gene underexpressed in ischemia. Alternately, genes that are expressed at a level that is at least about 10%, 20%, 30%, 40%, 50%, 60%, 70%, 80%, 90%, or 100% higher than the level in a control is a gene overexpressed in ischemia and a gene that is expressed at a level that is at least about 10%, 20%, 30%, 40%, 50%, 60%, 70%, 80%, 90%, or 100% lower than the level in a control is a gene underexpressed in ischemia.

A "plurality" refers to two or more or all, for example, 2, 3, 4, 5, 6, 7, 8, 9, 10, 11, 12, 13, 14, 15, 16, 17, 18, 19, 20, 21, 22, 23 or more (e.g., genes). In some embodiments, a plurality refers to concurrent or sequential determination of about 15-85, 20-60 or 40-50 genes, for example, about 15, 20, 25, 30, 35, 40, 45, 50, 55, 60, 65, 70, 75, 80, 85, 90, 95 or 100, or more or all, genes. In some embodiments, "plurality" refers to all genes listed in one or more tables, e.g., all genes listed in Tables 7A, 7B, 13A, 13B, 14 and 15.

"Sample" or "biological sample" includes sections of tissues such as biopsy and autopsy samples, and frozen sections taken for histologic purposes. Such samples include blood, sputum, tissue, lysed cells, brain biopsy, cultured cells, e.g., primary cultures, explants, and transformed cells, stool, urine, etc. A biological sample is typically obtained from a eukaryotic organism, most preferably a mammal such as a primate, e.g., chimpanzee or human; cow; dog; cat; a rodent, e.g., guinea pig, rat, mouse; rabbit; or a bird; reptile; or fish.

"Array" as used herein refers to a solid support comprising attached nucleic acid or peptide probes. Arrays typically comprise a plurality of different nucleic acid or peptide probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 6,040,193, 5,424,186 and Fodor et al., *Science,* 251:767-777 (1991). These arrays may generally be produced using mechanical synthesis methods or light directed synthesis methods which incorporate a combination of photolithographic methods and solid phase synthesis methods. Techniques for the synthesis of these arrays using mechanical synthesis methods are described in, e.g., U.S. Pat. No. 5,384,261. Arrays may comprise a planar surface or may be nucleic acids or peptides on beads, gels, polymeric surfaces, fibers such as fiber optics, glass or any other appropriate substrate as described in, e.g., U.S. Pat. Nos. 5,770,358, 5,789,162, 5,708,153, 6,040,193 and 5,800, 992. Arrays may be packaged in such a manner as to allow for diagnostics or other manipulation of an all inclusive device, as described in, e.g., U.S. Pat. Nos. 5,856,174 and 5,922,591.

The term "gene" means the segment of DNA involved in producing a polypeptide chain; it includes regions preceding and following the coding region (leader and trailer) as well as intervening sequences (introns) between individual coding segments (exons).

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The phrase "stringent hybridization conditions" refers to conditions under which a probe will hybridize to its target subsequence, typically in a complex mixture of nucleic acid, but to no other sequences. Stringent hybridization conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes,* "Overview of principles of hybridization and the strategy of nucleic acid assays" (1993). Generally, stringent hybridization conditions are selected to be about 5-10° C. lower than the thermal melting point for the specific sequence at a defined ionic strength Ph. The $T_m$ is the temperature (under defined ionic strength, Ph, and nucleic concentration) at which 50% of the probes complementary to the target hybridize to the target sequence at equilibrium (as the target sequences are present in excess, at $T_m$, 50% of the probes are occupied at equilibrium). Stringent hybridization conditions will be those in which the salt concentration is less than about 1.0 M sodium ion, typically about 0.01 to 1.0 M sodium ion concentration (or other salts) at Ph 7.0 to 8.3 and the temperature is at least about 30° C. for short probes (e.g., 10 to 50 nucleotides) and at least about 60° C. for long probes (e.g., greater than 50 nucleotides). Stringent hybridization conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent hybridization conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, α-carboxyglutamate, and O-phosphoserine. "Amino acid analogs" refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine I, Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, preferably 65%, 70%, 75%, 80%, 85%, 90%, or 95% identity over a specified region of an ischemia-associated gene (e.g., a gene set forth in Tables 7A, 7B, 13A, 13B, 14 and 15), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to ischemia-associated nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J.*

Mol. Biol. 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=-4 and a comparison of both strands. For amino acid sequences, the BLASTP program uses as defaults a word length of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=-4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

By "host cell" is meant a cell that contains an expression vector and supports the replication or expression of the expression vector. Host cells may be, for example, prokaryotic cells such as *E. coli* or eukaryotic cells such as yeast cells or mammalian cells such as CHO cells.

"Inhibitors," "activators," and "modulators" of expression or of activity are used to refer to inhibitory, activating, or modulating molecules, respectively, identified using in vitro and in vivo assays for expression or activity, e.g., ligands, agonists, antagonists, and their homologs and mimetics. The term "modulator" includes inhibitors and activators. Inhibitors are agents that, e.g., inhibit expression of a polypeptide or polynucleotide of the invention or bind to, partially or totally block stimulation or enzymatic activity, decrease, prevent, delay activation, inactivate, desensitize, or down regulate the activity of a polypeptide or polynucleotide of the invention, e.g., antagonists. Activators are agents that, e.g., induce or activate the expression of a polypeptide or polynucleotide of the invention or bind to, stimulate, increase, open, activate, facilitate, enhance activation or enzymatic activity, sensitize or up regulate the activity of a polypeptide or polynucleotide of the invention, e.g., agonists. Modulators include naturally occurring and synthetic ligands, antagonists, agonists, small chemical molecules and the like. Assays to identify inhibitors and activators include, e.g., applying putative modulator compounds to cells, in the presence or absence of a polypeptide or polynucleotide of the invention and then determining the functional effects on a polypeptide or polynucleotide of the invention activity. Samples or assays comprising a polypeptide or polynucleotide of the invention that are treated with a potential activator, inhibitor, or modulator are compared to control samples without the inhibitor, activator, or modulator to examine the extent of effect. Control samples (untreated with modulators) are assigned a relative activity value of 100%. Inhibition is achieved when the activity value of a polypeptide or polynucleotide of the invention relative to the control is about 80%, optionally 50% or 25-1%. Activation is achieved when the activity value of a polypeptide or polynucleotide of the invention relative to the control is 110%, optionally 150%, optionally 200-500%, or 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, RNAi, oligonucleotide, etc. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 Daltons and less than about 2500 Daltons, preferably less than about 2000 Daltons, preferably between about 100 to about 1000 Daltons, more preferably between about 200 to about 500 Daltons.

BRIEF DESCRIPTION OF THE DRAWINGS

FIG. 11A. 3 h IS predictors. Combined 60-probe set predictors from combined analysis on 3 h IS vs all controls (healthy, MI and SAVVY) were input in PAM. FIG. 11B. 24 h IS predictors. Combined 46-probe set predictors from combined analysis on 24 h IS vs all controls (healthy, MI and SAVVY) were input in PAM. FIG. 11C. Combined 3 h and 24 h IS predictors. Combined 97-probe set predictors from combined analysis on 3 h IS and 24 h IS vs all controls (healthy, MI and SAVVY) were input in PAM.

FIG. 15A-B. A. Hierarchical cluster analysis of the 37 genes found to differentiate cardioembolic stroke due to atrial fibrillation from non-atrial fibrillation causes. Genes are shown on the y-axis and subjects are shown on the x-axis. Red indicates a high level of gene expression and blue indicates a low level of gene expression. Subjects can be observed to cluster by diagnosis. A group of genes have a high level of expression in cardioembolic stroke due to atrial fibrillation and a low level of expression in non-atrial fibrillation causes. A group of genes have a low level of expression in cardioembolic stroke due to atrial fibrillation and a high level of expression in non-atrial fibrillation causes. B. Principal Component Analysis of the 37 genes found to differentiate cardioembolic stroke due to atrial fibrillation from non-atrial fibrillation causes. Each sphere represents a single subject. The ellipsoid surrounding the spheres represents two standard deviations from the group mean.

DETAILED DESCRIPTION

1. Introduction

Figure 1:
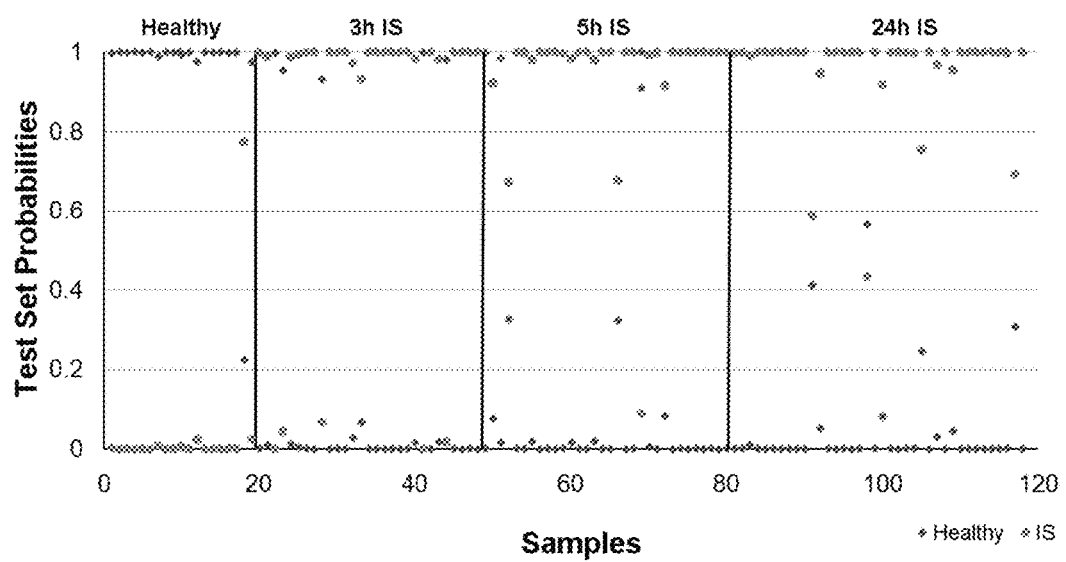
FIG. 1. PAM prediction accuracy of IS and Healthy controls using the set of 29 gene predictors of IS from Tang et al, 2006. The Prediction Analysis of Microarrays (PAM) algorithm (K-NN, number of neighbors n=10) was trained on the expression values of a first random half of IS (n=35, 100 samples) and healthy (n=19) subjects from the current study using the 29 IS predictors from Tang et al, 2006. Then, these 29 IS predictors were used to predict the class of the second half of the samples (IS n=35, 99 samples; and healthy n=19, Test Set) and calculate the prediction accuracy. The X-axis represents the patient sample number and the Y-axis represents the Test Set probability of diagnosis. A sample is considered misclassified if the predicted class does not match the known class with a probability greater than 0.5.

The present invention provides biomarkers for diagnosing the occurrence and risk of stroke in a patient, and further biomarkers for determining the cause of stroke in an individual diagnosed as experiencing a stroke or with a predisposition for experiencing a stroke. Evaluation of the expression levels of combined biomarkers, e.g., in a sample of blood, serum or plasma, allows the rapid diagnosis of the occurrence and cause of stroke in a patient who has experienced a suspected stroke event or who is experiencing symptoms indicative of a risk of stroke. By simultaneously determining whether a stroke has occurred, and the underlying cause of the stroke, appropriate medical treatment or intervention regimes are delivered to the patient as rapidly as possible. It is particularly desirable to be able to diagnose and treat a patient within 3 hours of a suspected stroke event. The present invention makes this possible, e.g., using available microarray technologies.

The biomarkers described herein for the diagnosis of the occurrence and risk of stroke can be used together, e.g., on a single microarray or in a single assay procedure. The biomarkers also find use independently for the diagnosis of the occurrence of stroke, e.g., in conjunction with alternative methods for determining the cause of stroke, and for determining the cause of stroke, e.g., in conjunction with alternative methods for determining whether a stroke has occurred.

2. Patients Who can Benefit from the Present Methods

Individuals who will benefit from the present methods may be exhibiting symptoms of ischemic stroke. In some embodiments, the subject has experienced an ischemic event (e.g., TIA, ischemic stroke, myocardial infarction, peripheral vascular disease, or venous thromboembolism). Alternatively, the subject may be suspected of having experienced an ischemic event. In some embodiments, the subject has not experienced and/or is not at risk of having an intracerebral hemorrhage or hemorrhagic stroke. In some embodiments, the subject has been diagnosed as having not experienced and/or not at risk of having an intracerebral hemorrhage or hemorrhagic stroke.

In some embodiments, the levels of expression of the panel of biomarkers are determined within 3 hours of a suspected ischemic event. In some embodiments, the levels of expression of the panel of biomarkers are determined at 3 or more hours after a suspected ischemic event. In some embodiments, the levels of expression of the panel of biomarkers are determined within 6, 12, 18, 24, 36, 48 hours of a suspected ischemic event.

In some cases, the subject is asymptomatic, but may have a risk or predisposition to experiencing ischemic stroke, e.g., based on genetics, a related disease condition, environment or lifestyle. In some embodiments, the patient has one or more vascular risk factors, e.g., hypertension, diabetes mellitus, hyperlipidemia, or tobacco smoking.

3. Biomarkers Useful for the Prediction or Diagnosis of Stroke

Biomarkers useful for the prediction, diagnosis or confirmation of the occurrence of ischemic stroke are listed in Tables 7A and 7B. Determination of the expression levels of a plurality of the biomarkers of Table 7A can be performed for the prediction, diagnosis or confirmation of the occurrence of stroke in conjunction with other biomarkers known in the art for the prediction, diagnosis or confirmation of the occurrence of stroke, in conjunction with other methods known in the art for the diagnosis of stroke, in conjunction with biomarkers described herein and known in the art useful for determining the cause of stroke (e.g., as described herein) and/or in conjunction with methods known in the art for determining the cause of stroke.

Determination of the expression levels of a plurality of the biomarkers of Table 7A can be performed for the prediction, diagnosis or confirmation of the occurrence of stroke can also be performed independently, e.g., to diagnose that a stroke has occurred or determine the risk that a patient may suffer a stroke, independently of its cause.

In some embodiments, the expression levels of at least about 3, 5, 10, 15, 20, 25, 30, 40, 50, 60 or more biomarkers from Table 7A (and Table 7B) are determined. In some embodiments, the expression levels of a plurality of biomarkers in Table 7A and a plurality of biomarkers in Table 7B are determined.

In some embodiments, the level of expression of biomarkers indicative of the occurrence of stroke is determined within 3 hours of a suspected ischemic event. In an otherwise healthy individual (i.e., no myocardial infarction, no vascular risk factors), an increased expression level of one or more or all ischemic stroke-associated biomarkers of Table 7A selected from the group consisting of FAT3, GADL1, CXADR, RNF141, CLEC4E, TIMP2, ANKRD28, TIMM8A, PTPRD, CCRL1, FCRL4, DLX6, GABRB2, GYPA, PHTF1, CKLF, CKLF, RRAGD, CLEC4E, CKLF, FGD4, CPEB2, LOC100290882, UBXN2B, ENTPD1, BST1, LTB4R, F5, IFRD1, KIAA0319, CHMP1B, MCTP1, VNN3, AMN1, LAMP2, FCHO2, ZNF608, REM2, QKI, RBM25, FAR2, ST3GAL6, HNRNPH2, GAB1, UBR5, VAPA, MCTP1 and SH3GL3 indicates that the patient suffers from or is at risk of developing ischemic stroke. In an otherwise healthy individual (i.e., no myocardial infarction, no vascular risk factors), a decreased expression level of one or more or all ischemic stroke-associated biomarkers of Table 7A selected from the group consisting of PGM5, CCDC144C///LOC100134159, LECT2, SHOX, TBX5, SPTLC3, SNIP, RBMS3, P704P, THSD4, SNRPN, GLYATL1, DKRZP434L187, OVOL2, SPIB, BXDC5, UNC5B, ASTN2, FLJ35934, CCDC144A, ALDOAP2, LDB3, LOC729222///PPFIBP1, HNRNPUL2, ELAVL2, PRTG, FOXA2, SCD5, LOC283027, LOC344595, RPL22, LOC100129488 and RPL22 indicates that the patient suffers from or is at risk of developing ischemic stroke.

In various embodiments, in an individual presenting with myocardial infarction within 3 hours of a suspected ischemic event, an increased expression level of one or more or all ischemic stroke-associated biomarkers of Table 7A selected from the group consisting of CLEC4E, TIMP2, FGD4, CPEB2, LTB4R and VNN3 indicates that the individual suffers from or is at risk of developing ischemic stroke. In various embodiments, in an individual presenting with myocardial infarction within 3 hours of a suspected ischemic event, a decreased expression level of one or more or all ischemic stroke-associated biomarkers of Table 7A selected from the group consisting of PGM5, CCDC144C///LOC100134159, LECT2, SHOX, TBX5, SPTLC3, SNIP, RBMS3, P704P, THSD4, FAT3, SNRPN, GLYATL1, GADL1, CXADR, OVOL2, RNF141, SPIB, BXDC5, UNC5B, ASTN2, FLJ35934, ANKRD28, CCDC144A, TIMM8A, ALDOAP2, LDB3, PTPRD, LOC729222///PPFIBP1, CCRL1, HNRNPUL2, FCRL4, ELAVL2, PRTG, DLX6, FOXA2, SCD5, GABRB2, GYPA, PHTF1, CKLF, CKLF, RRAGD, CKLF, LOC100290882, UBXN2B, ENTPD1, BST1, F5, IFRD1, KIAA0319, CHMP1B, MCTP1, AMN1, LAMP2, FCHO2, ZNF608, REM2, QKI, RBM25, FAR2, ST3GAL6, HNRNPH2, GAB1, UBR5, VAPA, LOC283027, LOC344595, RPL22, LOC100129488, RPL22, MCTP1 and SH3GL3 indicates that the individual suffers from or is at risk of developing ischemic stroke.

In various embodiments, in an individual presenting with one or more vascular risk factors (e.g., hypertension, diabetes mellitus, hyperlipidemia, or tobacco smoking) within 3 hours of a suspected ischemic event, an increased expression level of one or more or all ischemic stroke-associated biomarkers of Table 7A selected from the group consisting of RNF141, CLEC4E, TIMP2, PHTF1, CKLF, CKLF, RRAGD, CLEC4E, CKLF, FGD4, CPEB2, LOC100290882, UBXN2B, ENTPD1, BST1, LTB4R, F5, IFRD1, KIAA0319, CHMP1B, MCTP1, VNN3, AMN1, LAMP2, FCHO2, ZNF608, REM2, QKI, RBM25, FAR2, ST3GAL6, HNRNPH2, GAB1, UBR5, VAPA and MCTP1 indicates that the individual suffers from or is at risk of developing ischemic stroke. In various embodiments, in an individual presenting with one or more vascular risk factors within 3 hours of a suspected ischemic event, a decreased expression level of one or more or all ischemic stroke-associated biomarkers of Table 7A selected from the group consisting of PGM5, CCDC144C///LOC100134159, LECT2, SHOX, TBX5, SPTLC3, SNIP, RBMS3, P704P, THSD4, FAT3, SNRPN, GLYATL1, GADL1, CXADR, OVOL2, SPIB, BXDC5, UNC5B, ASTN2, FLJ35934, ANKRD28, CCDC144A, TIMM8A, ALDOAP2, LDB3, PTPRD, LOC729222///PPFIBP1, CCRL1, HNRNPUL2, FCRL4, ELAVL2, PRTG, DLX6, FOXA2, SCD5, GABRB2, GYPA, LOC283027, LOC344595, RPL22, LOC100129488, RPL22 and SH3GL3 indicates that the individual suffers from or is at risk of developing ischemic stroke.

In some embodiments, the level of expression of biomarkers indicative of the occurrence of stroke is determined 3 or more hours after a suspected ischemic event. In an otherwise healthy individual (i.e., no myocardial infarction, no vascular risk factors), an increased expression level of one or more or all ischemic stroke-associated biomarkers of Table 7A selected from the group consisting of PGM5, CCDC144C///LOC100134159, LECT2, SHOX, TBX5, SNIP, RBMS3, P704P, THSD4, FAT3, SNRPN, GLYATL1, GADL1, CXADR, OVOL2, RNF141, CLEC4E, BXDC5, UNC5B, TIMP2, ASTN2, FLJ35934, ANKRD28, CCDC144A, TIMM8A, ALDOAP2, LDB3, PTPRD, LOC729222///PPFIBP1, CCRL1, FCRL4, ELAVL2, PRTG, DLX6, SCD5, GABRB2, GYPA, PHTF1, CKLF, CKLF, RRAGD, CLEC4E, CKLF, FGD4, CPEB2, LOC100290882, UBXN2B, ENTPD1, BST1, LTB4R, F5, IFRD1, KIAA0319, CHMP1B, MCTP1, VNN3, AMN1, LAMP2, FCHO2, ZNF608, REM2, QKI, RBM25, FAR2, ST3GAL6, HNRNPH2, GAB1, UBR5, VAPA, LOC283027, LOC344595, RPL22, LOC100129488 and MCTP1 indicates that the patient suffers from or is at risk of developing ischemic stroke. In an otherwise healthy individual (i.e., no myocardial infarction, no vascular risk factors), a decreased expression level of one or more or all ischemic stroke-associated biomarkers of Table 7A selected from the group consisting of SPTLC3, DKRZP434L187, SPIB, HNRNPUL2, FOXA2, RPL22 and SH3GL3 indicates that the patient suffers from or is at risk of developing ischemic stroke.

In various embodiments, in an individual presenting with myocardial infarction 3 or more hours after a suspected ischemic event, an increased expression level of one or more or all ischemic stroke-associated biomarkers of Table 7A selected from the group consisting of RNF141, CLEC4E, TIMP2, HNRNPUL2, PHTF1, CKLF, CKLF, RRAGD, CLEC4E, CKLF, FGD4, CPEB2, UBXN2B, BST1, LTB4R, F5, IFRD1, KIAA0319, MCTP1, VNN3, AMN1, LAMP2, ZNF608, FAR2, GAB1, VAPA and MCTP1 indicates that the individual suffers from or is at risk of developing ischemic stroke. In various embodiments, in an individual presenting with myocardial infarction 3 or more hours after a suspected ischemic event, a decreased expression level of one or more or all ischemic stroke-associated biomarkers of Table 7A selected from the group consisting of PGM5, CCDC144C///LOC100134159, LECT2, SHOX, TBX5, SPTLC3, SNIP, RBMS3, P704P, THSD4, FAT3, SNRPN, GLYATL1, GADL1, CXADR, OVOL2, SPIB, BXDC5, UNC5B, ASTN2, FLJ35934, ANKRD28, CCDC144A, TIMM8A, ALDOAP2, LDB3, PTPRD, LOC729222///PPFIBP1, CCRL1, FCRL4, ELAVL2, PRTG, DLX6, FOXA2, SCD5, GABRB2, GYPA, LOC100290882, ENTPD1, CHMP1B, FCHO2, LOC283027, REM2, QKI, RBM25, ST3GAL6, HNRNPH2, UBR5, LOC344595, RPL22, LOC100129488, RPL22 and SH3GL3 indicates that the individual suffers from or is at risk of developing ischemic stroke.

In various embodiments, in an individual presenting with one or more vascular risk factors 3 or more hours after a suspected ischemic event, an increased expression level of one or more or all ischemic stroke-associated biomarkers of Table 7A selected from the group consisting of RNF141, CLEC4E, TIMP2, PHTF1, CKLF, CKLF, RRAGD, CLEC4E, CKLF, FGD4, CPEB2, LOC100290882, UBXN2B, ENTPD1, BST1, LTB4R, F5, IFRD1, KIAA0319, CHMP1B, MCTP1, VNN3, AMN1, LAMP2, FCHO2, ZNF608, REM2, QKI, RBM25, FAR2, ST3GAL6, HNRNPH2, GAB1, UBR5, VAPA and MCTP1 indicates that the individual suffers from or is at risk of developing ischemic stroke. In various embodiments, in an individual presenting with one or more vascular risk factors 3 or more hours after a suspected ischemic event, a decreased expression level of one or more or all ischemic stroke-associated biomarkers of Table 7A selected from the group consisting of PGM5, CCDC144C///LOC100134159, LECT2, SHOX, TBX5, SPTLC3, SNIP, RBMS3, P704P, THSD4, FAT3, SNRPN, GLYATL1, GADL1, CXADR, OVOL2, SPIB, BXDC5, UNC5B, ASTN2, FLJ35934, ANKRD28, CCDC144A, TIMM8A, ALDOAP2, LDB3, PTPRD, LOC729222///PPFIBP1, CCRL1, HNRNPUL2, FCRL4, ELAVL2, PRTG, DLX6, FOXA2, SCD5, GABRB2, GYPA, LOC283027, LOC344595, RPL22, LOC100129488, RPL22 and SH3GL3 indicates that the individual suffers from or is at risk of developing ischemic stroke.

Overexpression or underexpression of a plurality of biomarkers from Table 7A (and Table 7B) that is at least about 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, or more, in comparison to the expression levels of a plurality of stably expressed endogenous reference biomarkers, e.g., those listed in Table 16 indicates that the subject has experienced or is at risk of experiencing an ischemic stroke. Overexpression or underexpression of a plurality of biomarkers from Table 7A (and Table 7B) that is at least about 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, or more, in comparison to the expression level of the same biomarker in an individual or a population of individuals who have not experienced a vascular event indicates that the subject has experienced or is at risk of experiencing an ischemic stroke.

4. Biomarkers Useful for the Diagnosis of Cause of Stroke

Biomarkers useful for the determination and diagnosis of the cause of stroke are listed in Tables 13A, 13B, 14 and 15. Determination of the expression levels of a plurality of the biomarkers of Tables 13A, 13B, 14 and 15 independently can be performed for the determination of the cause of stroke in conjunction with biomarkers described herein and known in the art for the prediction, diagnosis or confirmation of the occurrence of stroke, in conjunction with other methods known in the art for the diagnosis of stroke, in conjunction with other biomarkers known in the art useful for determining the cause of stroke (e.g., as described herein) and/or in conjunction with methods known in the art for determining the cause of stroke. Classification of stroke subtypes is known in the art and reviewed in, e.g., in Amarenco, et al., *Cerebrovasc Dis* (2009) 27:493-501.

Determination of the expression levels of a plurality of the biomarkers of Tables 13A, 14 and 15 can be performed for the determination of the cause of stroke can also be performed independently, e.g., to diagnose the cause of a stroke when it is already known that a stroke has occurred or that the patient has a predisposition to experience ischemic stroke.

In some embodiments, the expression levels of at least about 3, 5, 10, 15, 20, 25, 30, 40, 50, 60 or more biomarkers from Tables 13A (and Table 13B) are independently determined. In some embodiments, the expression levels of at least about 3, 5, 10, 15, 20, 25, 30, 40, 50, 60 or more biomarkers from Table 14 are independently determined. In some embodiments, the expression levels of at least about 3, 5, 10, 15, 20, 25, 30, 40, 50, 60 or more biomarkers from Table 15 are independently determined. In some embodiments, the expression levels of a plurality of biomarkers in Table 13A and a plurality of biomarkers in Table 13B are determined. In some embodiments, the expression levels of a plurality of biomarkers in Table 14 are determined. In some embodiments, the expression levels of a plurality of biomarkers in Table 15 are determined.

The biomarkers in Tables 13A and 13B find use in the determination of whether a patient has experienced or has a predisposition to experience cardioembolic stroke (a.k.a, cardiac embolism, cardioembolism emboligenic heart disease). A cardioembolic stroke occurs when a thrombus (clot) dislodges from the heart, travels through the cardiovascular system and lodges in the brain, first cutting off the blood supply and then often causing a hemorrhagic bleed. In some embodiments an increased expression level of one or more or all ischemic stroke-associated biomarkers of Table 13A selected from the group consisting of IRF6, ZNF254, GRM5, EXT2, AP3S2, PIK3C2B, ARHGEF5, COL13A1, PTPN20A///PTPN20B, LHFP, BANK1, HLA-DOA, EBF1, TMEM19, LHFP, FCRL1, OOEP and LRRC37A3 indicates that the patient has experienced or is at risk for cardioembolic stroke. In some embodiments, a decreased expression level of one or more or all ischemic stroke-associated biomarkers of Table 13A selected from the group consisting of LOC284751, CD46, ENPP2, C19orf28, TSKS, CHURC1, ADAMTSL4, FLJ40125, CLEC18A, ARHGEF12, C16orf68, TFDP1 and GSTK1 indicates that the patient has experienced or is at risk for cardioembolic stroke.

Overexpression or underexpression of a plurality of biomarkers from Table 13A (and Table 13B) that is at least about 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, or more, in comparison to the expression levels of a plurality of stably expressed endogenous reference biomarkers, e.g., those listed in Table 16 indicates that the subject has experienced or is at risk of experiencing cardioembolic stroke. Overexpression or underexpression of a plurality of biomarkers from Table 13A (and Table 13B) that is at least about 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, or more, in comparison to the expression level of the same biomarker in an individual or a population of individuals who have not experienced a vascular event indicates that the subject has experienced or is at risk of experiencing cardioembolic stroke.

The biomarkers in Table 14 find use in the determination of whether a patient has experienced or has a predisposition to experience carotid stenosis. Carotid stenosis is a narrowing or constriction of the inner surface (lumen) of the carotid artery, usually caused by atherosclerosis. An inflammatory buildup of plaque can narrow the carotid artery and can be a source of embolization. Emboli break off from the plaque and travel through the circulation to blood vessels in the brain, causing ischemia that can either be temporary (e.g., a transient ischemic attack), or permanent resulting in a thromboembolic stroke (a.k.a., atherothrombosis, large-artery atherosclerosis, atherosclerosis with stenosis). In some embodiments, an increased expression level of one or more or all ischemic stroke-associated biomarkers of Table 14 selected from the group consisting of NT5E, CLASP2, GRM5, PROCR, ARHGEF5, AKR1C3, COL13A1, LHFP, RNF7, CYTH3, EBF1, RANBP10, PRSS35, C12orf42 and LOC100127980 indicates that the patient has experienced or is at risk for carotid stenosis. In some embodiments, a decreased expression level of one or more or all ischemic stroke-associated biomarkers of Table 14 selected from the group consisting of FLJ31945, LOC284751, LOC100271832, MTBP, ICAM4, SHOX2, DOPEY2, CMBL, LOC146880, SLC20A1, SLC6A19, ARHGEF12, C16orf68, GIPC2 and LOC100144603 indicates that the patient has experienced or is at risk for carotid stenosis.

Overexpression or underexpression of a plurality of biomarkers from Table 14 that is at least about 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, or more, in comparison to the expression levels of a plurality of stably expressed endogenous reference biomarkers, e.g., those listed in Table 16 indicates that the subject has experienced or is at risk of experiencing carotid stenosis. Overexpression or underexpression of a plurality of biomarkers from Table 14 that is at least about 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, or more, in comparison to the expression level of the same biomarker in an individual or a population of individuals who have not experienced a vascular event indicates that the subject has experienced or is at risk of experiencing carotid stenosis.

The biomarkers in Table 15 find use in the determination of whether a patient has experienced or has a predisposition to experience atrial fibrillation. Atrial fibrillation (AF or A-fib) is the most common cardiac arrhythmia and involves the two upper chambers (atria) of the heart fibrillating (i.e., quivering) instead of a coordinated contraction. In some instances, cardioembolic stroke can occur as a result of atrial fibrillation. Cardioembolic stroke can be a downstream result of atrial fibrillation in that stagnant blood in the fibrillating atrium can form a thrombus that then embolises to the cerebral circulation, blocking arterial blood flow and causing ischaemic injury. In some embodiments, an increased expression level of one or more or all ischemic stroke-associated biomarkers of Table 15 selected from the group consisting of SMC1A, SNORA68, GRLF1, SDC4, HIPK2, LOC100129034, CMTM1 and TTC7A indicates that the patient has experienced or is at risk for atrial fibrillation. In some embodiments, a decreased expression level of one or more or all ischemic stroke-associated biomarkers of Table 15 selected from the group consisting of LRRC43, MIF///SLC2A11, PER3, PPIE, COL13A1, DUSP16, LOC100129034, BRUNOL6, GPR176, C6orf164 and MAP3K7IP1 indicates that the patient has experienced or is at risk for atrial fibrillation.

Overexpression or underexpression of a plurality of biomarkers from Table 15 that is at least about 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, or more, in comparison to the expression levels of a plurality of stably expressed endogenous reference biomarkers, e.g., those listed in Table 16 indicates that the subject has experienced or is at risk of experiencing atrial fibrillation. Overexpression or underexpression of a plurality of biomarkers from Table 15 that is at least about 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, or more, in comparison to the expression level of the same biomarker in an individual or a population of individuals who have not experienced a vascular event indicates that the subject has experienced or is at risk of experiencing atrial fibrillation.

5. Comparison to a Control Level of Expression

The expression of the ischemic stroke-associated biomarkers are compared to a control ischemic stroke level of expression. As appropriate, the control level of expression can be the expression level of the same ischemic stroke-associated biomarker in an otherwise healthy individual (e.g., in an individual who has not experienced and/or is not at risk of experiencing TIA). In some embodiments, the control level of expression is the expression level of a plurality of stably expressed endogenous reference biomarkers, as described herein or known in the art. In some embodiments, the control level of expression is a predetermined threshold level of expression of the same ischemic stroke-associated biomarker, e.g., based on the expression level of the biomarker in a population of otherwise healthy individuals. In some embodiments, the expression level of the ischemic stroke-associated biomarker and the ischemic stroke-associated biomarker in an otherwise healthy individual are normalized to (i.e., divided by), e.g., the expression levels of a plurality of stably expressed endogenous reference biomarkers.

In some embodiments, the overexpression or underexpression of a ischemic stroke-associated biomarker is determined with reference to the expression of the same ischemic stroke associated biomarker in an otherwise healthy individual. For example, a healthy or normal control individual has not experienced and/or is not at risk of experiencing ischemic stroke. The healthy or normal control individual generally has not experienced a vascular event (e.g., TIA, ischemic stroke, myocardial infarction, peripheral vascular disease, or venous thromboembolism). The healthy or normal control individual generally does not have one or more vascular risk factors (e.g., hypertension, diabetes mellitus, hyperlipidemia, or tobacco smoking). As appropriate, the expression levels of the target ischemic stroke-associated biomarker in the healthy or normal control individual can be normalized (i.e., divided by) the expression levels of a plurality of stably expressed endogenous reference biomarkers.

In some embodiments, the overexpression or underexpression of a ischemic stroke-associated biomarker is determined with reference to one or more stably expressed endogenous reference biomarkers. Internal control biomarkers or endogenous reference biomarkers are expressed at the same or nearly the same expression levels in the blood of patients with stroke or TIAs as compared to control patients. Target biomarkers are expressed at higher or lower levels in the blood of the stroke or TIA patients. The expression levels of the target biomarker to the reference biomarker are normalized by dividing the expression level of the target biomarker to the expression levels of a plurality of endogenous reference biomarkers. The normalized expression level of a target biomarker can be used to predict the occurrence or lack thereof of stroke or TIA, and/or the cause of stroke or TIA.

In some embodiments, the expression level of the ischemic stroke-associated biomarker from a patient suspected of having or experiencing ischemic stroke and from a control patient are normalized with respect to the expression levels of a plurality of stably expressed endogenous. The expression levels of the normalized expression of the ischemic stroke-associated biomarker is compared to the expression levels of the normalized expression of the same ischemic stroke-associated biomarker in a control patient. The determined fold change in expression=normalized expression of target biomarker in ischemic stroke patient/normalized expression of target biomarker in control patient. Overexpression or underexpression of the normalized ischemic stroke-associated biomarker in the ischemic stroke patient by at least about 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, or more, in comparison to the expression levels of the normalized ischemic stroke-associated biomarker in a healthy control patient indicates that the ischemic stroke patient has experienced or is at risk of experiencing ischemic stroke.

In some embodiments, the control level of expression is a predetermined threshold level. The threshold level can correspond to the level of expression of the same ischemic stroke-associated biomarker in an otherwise healthy individual or a population of otherwise healthy individuals, optionally normalized to the expression levels of a plurality of endogenous reference biomarkers. After expression levels and normalized expression levels of the ischemic stroke-associated biomarkers are determined in a representative number of otherwise healthy individuals and individuals predisposed to experiencing ischemic stroke, normal and ischemic stroke expression levels of the ischemic stroke-associated biomarkers can be maintained in a database, allowing for determination of threshold expression levels indicative of the presence or absence of risk to experience ischemic stroke or the occurrence of ischemic stroke. If the predetermined threshold level of expression is with respect to a population of normal control patients, then overexpression or underexpression of the ischemic stroke-associated biomarker (usually normalized) in the ischemic stroke patient by at least about 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, or more, in comparison to the threshold level indicates that the ischemic stroke patient has experienced or is at risk of experiencing ischemic stroke. If the predetermined threshold level of expression is with respect to a population of patients known to have experienced ischemic stroke or known to be at risk for experiencing ischemic stroke, then an expression level in the patient suspected of experiencing ischemic stroke that is approximately equal to the threshold level (or overexpressed or underexpressed greater than the threshold level of expression), indicates that the ischemic stroke patient has experienced or is at risk of experiencing ischemic stroke.

With respect to the endogenous reference biomarkers used for comparison, preferably, Exemplary endogenous reference biomarkers that find use are listed in Table 16, below. Further suitable endogenous reference biomarkers are published, e.g., in Stamova, et al., *BMC Medical Genomics* (2009) 2:49. In some embodiments, the expression levels of a plurality of endogenous reference biomarkers are determined as a control. In some embodiments, the expression levels of at least about 2, 3, 4, 5, 6, 7, 8, 9, 10, 15, 20, 25, 30, 35, or more or all, endogenous reference biomarkers, e.g., as listed in Table 16 or known in the art, are determined as a control.

In some embodiments, the expression levels of the endogenous reference biomarkers GAPDH, ACTB, B2M, HMBS and PPM are determined as a control. In some embodiments, the expression levels of 2, 3, 4, 5, 6, 7, 8, 9, 10, 15, 20, 25, or more or all, endogenous reference biomarkers selected from the group consisting of USP7, MAPRE2, CSNK1G2, SAFB2, PRKAR2A, PI4 KB, CRTC1, HADHA, MAP1LC3B, KAT5, CDC2L1///CDC2L2, GTSE1, CDC2L1///CDC2L2, TCF25, CHP, LRRC40, hCG_2003956///LYPLA2///LYPLA2P1, DAXX, UBE2NL, EIF1, KCMF1, PRKRIP1, CHMP4A, TMEM184C, TINF2, PODNL1, FBXO42, LOC441258, RRP1, C10orf104, ZDHHC5, C9orf23, LRRC45, NACC1, LOC100133445/// LOC115110, PEX16 are determined as a control.

Biomarkers indicative of stroke or a particular cause of stroke have levels of expression that are at least about 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, or more, in comparison to the expression levels of a plurality of stably expressed endogenous reference biomarkers, e.g., the geometric average expression level of the evaluated endogenous reference biomarkers, e.g., 2, 3, 4, 5, 6, 7, 8, 9, 10, 15, 20, 25, 30, 35, or more biomarkers listed in Table 16.

6. Methods of Detecting Biomarkers

Gene expression may be measured using any method known in the art. One of skill in the art will appreciate that the means of measuring gene expression is not a critical aspect of the invention. The expression levels of the biomarkers can be detected at the transcriptional or translational (i.e., protein) level.

In some embodiments, the expression levels of the biomarkers are detected at the transcriptional level. A variety of methods of specific DNA and RNA measurement using nucleic acid hybridization techniques are known to those of skill in the art (see, Sambrook, supra and Ausubel, supra) and may be used to detect the expression of the genes set forth in Tables 7A, 7B, 13A, 13B, 14 and 15. Some methods involve an electrophoretic separation (e.g., Southern blot for detecting DNA, and Northern blot for detecting RNA), but measurement of DNA and RNA can also be carried out in the absence of electrophoretic separation (e.g., by dot blot). Southern blot of genomic DNA (e.g., from a human) can be used for screening for restriction fragment length polymorphism (RFLP) to detect the presence of a genetic disorder affecting a polypeptide of the invention. All forms of RNA can be detected, including, e.g., message RNA (mRNA), microRNA (miRNA), ribosomal RNA (rRNA) and transfer RNA (tRNA).

The selection of a nucleic acid hybridization format is not critical. A variety of nucleic acid hybridization formats are known to those skilled in the art. For example, common formats include sandwich assays and competition or displacement assays. Hybridization techniques are generally described in Hames and Higgins *Nucleic Acid Hybridization, A Practical Approach*, IRL Press (1985); Gall and Pardue, *Proc. Natl. Acad. Sci. U.S.A.*, 63:378-383 (1969); and John et al. *Nature*, 223:582-587 (1969).

Detection of a hybridization complex may require the binding of a signal-generating complex to a duplex of target and probe polynucleotides or nucleic acids. Typically, such binding occurs through ligand and anti-ligand interactions as between a ligand-conjugated probe and an anti-ligand conjugated with a signal. The binding of the signal generation complex is also readily amenable to accelerations by exposure to ultrasonic energy.

The label may also allow indirect detection of the hybridization complex. For example, where the label is a hapten or antigen, the sample can be detected by using antibodies. In these systems, a signal is generated by attaching fluorescent or enzyme molecules to the antibodies or in some cases, by attachment to a radioactive label (see, e.g., Tijssen, *"Practice and Theory of Enzyme Immunoassays," Laboratory Techniques in Biochemistry and Molecular Biology*, Burdon and van Knippenberg Eds., Elsevier (1985), pp. 9-20).

The probes are typically labeled either directly, as with isotopes, chromophores, lumiphores, chromogens, or indirectly, such as with biotin, to which a streptavidin complex may later bind. Thus, the detectable labels used in the assays of the present invention can be primary labels (where the label comprises an element that is detected directly or that produces a directly detectable element) or secondary labels (where the detected label binds to a primary label, e.g., as is common in immunological labeling). Typically, labeled signal nucleic acids are used to detect hybridization. Complementary nucleic acids or signal nucleic acids may be labeled by any one of several methods typically used to detect the presence of hybridized polynucleotides. The most common method of detection is the use of autoradiography with $^3$H, $^{125}$I, $^{35}$S, $^{14}$C, or $^{32}$P-labeled probes or the like.

Other labels include, e.g., ligands that bind to labeled antibodies, fluorophores, chemiluminescent agents, enzymes, and antibodies which can serve as specific binding pair members for a labeled ligand. An introduction to labels, labeling procedures and detection of labels is found in Polak and Van Noorden *Introduction to Immunocytochemistry*, 2nd ed., Springer Verlag, NY (1997); and in Haugland *Handbook of Fluorescent Probes and Research Chemicals*, a combined handbook and catalogue Published by Molecular Probes, Inc. (1996).

In general, a detector which monitors a particular probe or probe combination is used to detect the detection reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill in the art. Commonly, an optical image of a substrate comprising bound labeling moieties is digitized for subsequent computer analysis.

Most typically, the amount of RNA is measured by quantifying the amount of label fixed to the solid support by binding of the detection reagent. Typically, the presence of a modulator during incubation will increase or decrease the amount of label fixed to the solid support relative to a control incubation which does not comprise the modulator, or as compared to a baseline established for a particular reaction type. Means of detecting and quantifying labels are well known to those of skill in the art.

In preferred embodiments, the target nucleic acid or the probe is immobilized on a solid support. Solid supports suitable for use in the assays of the invention are known to those of skill in the art. As used herein, a solid support is a matrix of material in a substantially fixed arrangement.

For example, in one embodiment of the invention, microarrays are used to detect the pattern of gene expression. Microarrays provide one method for the simultaneous measurement of the expression levels of large numbers of genes. Each array consists of a reproducible pattern of a plurality of nucleic acids (e.g., a plurality of nucleic acids that hybridize to a plurality of the genes set forth in Tables 7A, 7B, 13A, 13B, 14 and 15) attached to a solid support. In one embodiment, the array contains a plurality of nucleic acids that hybridize to a plurality of the genes listed in Table 7A (and 7B). In one embodiment, the array contains a plurality of nucleic acids that hybridize to a plurality of the genes listed in Table 13A (and 13B). In one embodiment, the array contains a plurality of nucleic acids that hybridize to a plurality of the genes listed in Table 14. In one embodiment, the array contains a plurality of nucleic acids that hybridize to a plurality of the genes listed in Table 15. Labeled RNA or DNA is hybridized to complementary probes on the array and then detected by laser scanning. Hybridization intensities for each probe on the array are determined and converted to a quantitative read-out of relative gene expression levels in ischemia (e.g., stroke or transient ischemic attacks).

In some embodiments, a sample is obtained from a subject, total mRNA is isolated from the sample and is converted to labeled cRNA and then hybridized to an array. Relative transcript levels are calculated by reference to appropriate controls present on the array and in the sample. See Mahadevappa and Warrington, *Nat. Biotechnol.* 17, 1134-1136 (1999).

A variety of automated solid-phase assay techniques are also appropriate. For instance, very large scale immobilized polymer arrays (VLSIPS™), available from Affymetrix, Inc. (Santa Clara, Calif.) can be used to detect changes in expression levels of a plurality of genes involved in the same regulatory pathways simultaneously. See, Tijssen, supra., Fodor et al. (1991) *Science*, 251: 767-777; Sheldon et al. (1993) *Clinical Chemistry* 39(4): 718-719, and Kozal et al. (1996) *Nature Medicine* 2(7): 753-759. Integrated microfluidic systems and other point-of-care diagnostic devices available in the art also find use. See, e.g., Liu and Mathies, *Trends Biotechnol.* (2009) 27(10):572-81 and Tothill, *Semin Cell Dev Biol* (2009) 20(1):55-62. Microfluidics systems for use in detecting levels of expression of a plurality of nucleic acids are available, e.g., from NanoString Technologies, on the internet at nanostring.com.

Detection can be accomplished, for example, by using a labeled detection moiety that binds specifically to duplex nucleic acids (e.g., an antibody that is specific for RNA-DNA duplexes). One preferred example uses an antibody that recognizes DNA-RNA heteroduplexes in which the antibody is linked to an enzyme (typically by recombinant or covalent chemical bonding). The antibody is detected when the enzyme reacts with its substrate, producing a detectable product. Coutlee et al. (1989) *Analytical Biochemistry* 181: 153-162; Bogulayski (1986) et al. *J. Immunol. Methods*

89:123-130; Prooijen-Knegt (1982) *Exp. Cell Res.* 141:397-407; Rudkin (1976) *Nature* 265:472-473, Stollar (1970) *Proc. Nat'l Acad. Sci. USA* 65:993-1000; Ballard (1982) *Mol. Immunol.* 19:793-799; Pisetsky and Caster (1982) *Mol. Immunol.* 19:645-650; Viscidi et al. (1988) *J. Clin. Microbial.* 41:199-209; and Kiney et al. (1989) *J. Clin. Microbiol.* 27:6-12 describe antibodies to RNA duplexes, including homo and heteroduplexes. Kits comprising antibodies specific for DNA:RNA hybrids are available, e.g., from Digene Diagnostics, Inc. (Beltsville, Md.).

In addition to available antibodies, one of skill in the art can easily make antibodies specific for nucleic acid duplexes using existing techniques, or modify those antibodies that are commercially or publicly available. In addition to the art referenced above, general methods for producing polyclonal and monoclonal antibodies are known to those of skill in the art (see, e.g., Paul (3rd ed.) *Fundamental Immunology* Raven Press, Ltd., NY (1993); Coligan, et al., *Current Protocols in Immunology*, Wiley Interscience (1991-2008); Harlow and Lane, *Antibodies: A Laboratory Manual* Cold Spring Harbor Press, NY (1988); Harlow and Lane, *Using Antibodies*, Cold Spring Harbor Press, NY (1999); Stites et al. (eds.) *Basic and Clinical Immunology* (4th ed.) Lange Medical Publications, Los Altos, Calif., and references cited therein; *Goding Monoclonal Antibodies: Principles and Practice* (2d ed.) Academic Press, New York, N.Y., (1986); and Kohler and Milstein *Nature* 256: 495-497 (1975)). Other suitable techniques for antibody preparation include selection of libraries of recombinant antibodies in phage or similar vectors (see, Huse et al. *Science* 246:1275-1281 (1989); and Ward et al. *Nature* 341:544-546 (1989)). Specific monoclonal and polyclonal antibodies and antisera will usually bind with a $K_D$ of at least about 0.1 µM, preferably at least about 0.01 µM or better, and most typically and preferably, 0.001 µM or better.

The nucleic acids used in this invention can be either positive or negative probes. Positive probes bind to their targets and the presence of duplex formation is evidence of the presence of the target. Negative probes fail to bind to the suspect target and the absence of duplex formation is evidence of the presence of the target. For example, the use of a wild type specific nucleic acid probe or PCR primers may serve as a negative probe in an assay sample where only the nucleotide sequence of interest is present.

The sensitivity of the hybridization assays may be enhanced through use of a nucleic acid amplification system that multiplies the target nucleic acid being detected. Examples of such systems include the polymerase chain reaction (PCR) system, in particular RT-PCR or real time PCR, and the ligase chain reaction (LCR) system. Other methods recently described in the art are the nucleic acid sequence based amplification (NASBA, Cangene, Mississauga, Ontario) and Q Beta Replicase systems. These systems can be used to directly identify mutants where the PCR or LCR primers are designed to be extended or ligated only when a selected sequence is present. Alternatively, the selected sequences can be generally amplified using, for example, nonspecific PCR primers and the amplified target region later probed for a specific sequence indicative of a mutation. High throughput multiplex nucleic acid sequencing or "deep sequencing" to detect captured expressed biomarker genes also finds use. High throughput sequencing techniques are known in the art (e.g., 454 Sequencing on the internet at 454.com).

An alternative means for determining the level of expression of the nucleic acids of the present invention is in situ hybridization. In situ hybridization assays are well known and are generally described in Angerer et al., *Methods Enzymol.* 152:649-660 (1987). In an in situ hybridization assay, cells, preferentially human cells, e.g., blood cells, are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

In other embodiments, quantitative RT-PCR is used to detect the expression of a plurality of the genes set forth in Tables 7A, 7B, 13A, 13B, 14 and 15. In one embodiment, quantitative RT-PCR is used to detect a plurality of the genes listed in Table 7A (and 7B). In one embodiment, quantitative RT-PCR is used to detect a plurality of the genes listed in Table 13A (and 13B). In one embodiment, quantitative RT-PCR is used to detect a plurality of the genes listed in Table 14. In one embodiment, quantitative RT-PCR is used to detect a plurality of the genes listed in Table 15. A general overview of the applicable technology can be found, for example, in *A-Z of Quantitative PCR*, Bustin, ed., 2004, International University Line; *Quantitative PCR Protocols*, Kochanowski and Reischl, eds., 1999, Humana Press; *Clinical Applications of PCR*, Lo, ed., 2006, Humana Press; *PCR Protocols: A Guide to Methods and Applications* (Innis et al. eds. (1990)) and *PCR Technology: Principles and Applications for DNA Amplification* (Erlich, ed. (1992)). In addition, amplification technology is described in U.S. Pat. Nos. 4,683,195 and 4,683,202. Methods for multiplex PCR, known in the art, are applicable to the present invention.

Accordingly, in one embodiment of the invention provides a reaction mixture comprising a plurality of polynucleotides which specifically hybridize (e.g., primers) to a plurality of nucleic acid sequences of the genes set forth in Tables 7A, 7B, 13A, 13B, 14 and 15. In some embodiments, the invention provides a reaction mixture comprising a plurality of polynucleotides which specifically hybridize (e.g., primers) to a plurality of nucleic acid sequences of the genes set forth in Table 7A (and 7B). In some embodiments, the invention provides a reaction mixture comprising a plurality of polynucleotides which specifically hybridize (e.g., primers) to a plurality of nucleic acid sequences of the genes set forth in Table 13A (and 13B). In some embodiments, the invention provides a reaction mixture comprising a plurality of polynucleotides which specifically hybridize (e.g., primers) to a plurality of nucleic acid sequences of the genes set forth in Table 14. In some embodiments, the invention provides a reaction mixture comprising a plurality of polynucleotides which specifically hybridize (e.g., primers) to a plurality of nucleic acid sequences of the genes set forth in Table 15. In some embodiments, the reaction mixture is a PCR mixture, for example, a multiplex PCR mixture.

This invention relies on routine techniques in the field of recombinant genetics. Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. Basic texts disclosing the general methods of use in this invention include Sambrook et al., Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994-2008, Wiley Interscience)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, Tetrahedron Letts. 22:1859-1862 (1981), using an automated synthesizer, as described in Van Devanter et. al., Nucleic Acids Res. 12:6159-6168 (1984). Purification of oligonucleotides is by either native acrylamide gel electrophoresis or by anion-exchange HPLC as described in Pearson & Reanier, J. Chrom. 255:137-149 (1983).

In some embodiments, the expression level of the biomarkers described herein are detected at the translational or protein level. Detection of proteins is well known in the art, and methods for protein detection known in the art find use. Exemplary assays for determining the expression levels of a plurality of proteins include, e.g., ELISA, flow cytometry, mass spectrometry (e.g., MALDI or SELDI), surface plasmon resonance (e.g., BiaCore), microfluidics and other biosensor technologies. See, e.g., Tothill, *Semin Cell Dev Biol* (2009) 20(1):55-62.

7. Ischemic Stroke Reference Profiles

The invention also provides ischemia reference profiles. The reference profiles comprise information correlating the expression levels of a plurality of ischemia-associated genes (i.e., a plurality of the genes set forth in Tables 7A, 7B, 13A, 13B, 14 and 15) to particular types of ischemia. In one embodiment, the ischemia reference profile correlates the expression levels of a plurality of the genes listed in Tables 7A (and 7B) to the occurrence or risk of ischemia. In one embodiment, the ischemia reference profile correlates the expression levels of a plurality of the genes listed in Tables 13A (and 13B) to the occurrence or risk of cardioembolic stroke. In one embodiment, the ischemia reference profile correlates the expression levels of a plurality of the genes listed in Table 14 to the occurrence or risk of carotid stenosis. In one embodiment, the ischemia reference profile correlates the expression levels of a plurality of the genes listed in Table 15 to the occurrence or risk of atrial fibrillation. The profiles can conveniently be used to diagnose, monitor and prognose ischemia.

One embodiment of the invention provides an ischemia reference profile for subjects who have experienced or are at risk for experiencing stroke, regardless of cause. Accordingly, the ischemia reference profile correlates the expression levels of a plurality of the genes selected from Table 7A (and Table 7B). For example, an expression profile exhibiting at least about a 1.2-fold increase in expression of a plurality of the following genes: PGM5, CCDC144C/// LOC100134159, LECT2, SHOX, TBX5, SNIP, RBMS3, P704P, THSD4, FAT3, SNRPN, GLYATL1, GADL1, CXADR, OVOL2, RNF141, CLEC4E, BXDC5, UNC5B, TIMP2, ASTN2, FLJ35934, ANKRD28, CCDC144A, TIMM8A, ALDOAP2, LDB3, PTPRD, LOC729222///PP-FIBP1, CCRL1, FCRL4, ELAVL2, PRTG, DLX6, SCD5, GABRB2, GYPA, PHTF1, CKLF, CKLF, RRAGD, CLEC4E, CKLF, FGD4, CPEB2, LOC100290882, UBXN2B, ENTPD1, BST1, LTB4R, F5, IFRD1, KIAA0319, CHMP1B, MCTP1, VNN3, AMN1, LAMP2, FCHO2, ZNF608, REM2, QKI, RBM25, FAR2, ST3GAL6, HNRNPH2, GAB1, UBR5, VAPA, LOC283027, LOC344595, RPL22, LOC100129488 and MCTP1 when compared to the control level, and at least about a 1.2-fold decrease in expression of a plurality of the following genes: SPTLC3, DKRZP434L187, SPIB, HNRNPUL2, FOXA2, RPL22 and SH3GL3 when compared to the control level is a reference profile for a subject who has experienced or is at risk for stroke.

One embodiment of the invention provides an ischemia reference profile for subjects who have experienced or are at risk for experiencing cardioembolic stroke. Accordingly, the ischemia reference profile correlates the expression levels of a plurality of the genes selected from Table 13A (and Table 13B). For example, an expression profile exhibiting at least about a 1.2-fold increase in expression of a plurality of the following genes: IRF6, ZNF254, GRM5, EXT2, AP3S2, PIK3C2B, ARHGEF5, COL13A1, PTPN20A///PTPN20B, LHFP, BANK1, HLA-DOA, EBF1, TMEM19, LHFP, FCRL1, OOEP and LRRC37A3 when compared to the control level, and at least about a 1.2-fold decrease in expression of a plurality of the following genes: LOC284751, CD46, ENPP2, C19orf28, TSKS, CHURC1, ADAMTSL4, FLJ40125, CLEC18A, ARHGEF12, C16orf68, TFDP1 and GSTK1 when compared to the control level is a reference profile for a subject who has experienced or is at risk for a cardioembolic stroke.

One embodiment of the invention provides an ischemia reference profile for subjects who have experienced or are at risk for experiencing carotid stenosis and atherosclerotic stroke. Accordingly, the ischemia reference profile correlates the expression levels of a plurality of the genes selected from Table 14. For example, an expression profile exhibiting at least about a 1.2-fold increase in expression of a plurality of the following genes: NT5E, CLASP2, GRM5, PROCR, ARHGEF5, AKR1C3, COL13A1, LHFP, RNF7, CYTH3, EBF1, RANBP10, PRSS35, C12orf42 and LOC100127980 when compared to the control level, and at least about a 1.2-fold decrease in expression of a plurality of the following genes: FLJ31945, LOC284751, LOC100271832, MTBP, ICAM4, SHOX2, DOPEY2, CMBL, LOC146880, SLC20A1, SLC6A19, ARHGEF12, C16orf68, GIPC2 when compared to the control level is a reference profile for a subject who has experienced or is at risk for carotid stenosis and atherothrombotic stroke.

One embodiment of the invention provides an ischemia reference profile for subjects who have experienced or are at risk for experiencing atrial fibrillation. Accordingly, the ischemia reference profile correlates the expression levels of a plurality of the genes selected from Table 15. For example, an expression profile exhibiting at least about a 1.2-fold increase in expression of a plurality of the following genes: SMC1A, SNORA68, GRLF1, SDC4, HIPK2, LOC100129034, CMTM1 and TTC7A when compared to the control level, and at least about a 1.2-fold decrease in expression of a plurality of the following genes: LRRC43, MIF///SLC2A11, PER3, PPIE, COL13A1, DUSP16, LOC100129034, BRUNOL6, GPR176, C6orf164 and MAP3K7IP1 when compared to the control level is a reference profile for a subject who has experienced or is at risk for atrial fibrillation.

The reference profiles can be entered into a database, e.g., a relational database comprising data fitted into predefined categories. Each table, or relation, contains one or more data categories in columns. Each row contains a unique instance of data for the categories defined by the columns. For example, a typical database for the invention would include a table that describes a sample with columns for age, gender, reproductive status, expression profile and so forth. Another table would describe a disease: symptoms, level, sample identification, expression profile and so forth. In one embodiment, the invention matches the experimental sample to a database of reference samples. The database is assembled with a plurality of different samples to be used as reference samples. An individual reference sample in one embodiment will be obtained from a patient during a visit to a medical professional. Information about the physiological, disease and/or pharmacological status of the sample will also be obtained through any method available. This may include, but is not limited to, expression profile analysis, clinical analysis, medical history and/or patient interview. For example, the patient could be interviewed to determine age, sex, ethnic origin, symptoms or past diagnosis of disease, and the identity of any therapies the patient is currently undergoing. A plurality of these reference samples will be taken. A single individual may contribute a single reference sample or more than one sample over time. One skilled in the art will recognize that confidence levels in predictions based on comparison to a database increase as the number of reference samples in the database increases.

The database is organized into groups of reference samples. Each reference sample contains information about physiological, pharmacological and/or disease status. In one aspect the database is a relational database with data organized in three data tables, one where the samples are grouped primarily by physiological status, one where the samples are grouped primarily by disease status and one where the samples are grouped primarily by pharmacological status. Within each table the samples can be further grouped according to the two remaining categories. For example the physiological status table could be further categorized according to disease and pharmacological status.

As will be appreciated by one of skill in the art, the present invention may be embodied as a method, data processing system or program products. Accordingly, the present invention may take the form of data analysis systems, methods, analysis software, etc. Software written according to the present invention is to be stored in some form of computer readable medium, such as memory, hard-drive, DVD ROM or CD ROM, or transmitted over a network, and executed by a processor. The present invention also provides a computer system for analyzing physiological states, levels of disease states and/or therapeutic efficacy. The computer system comprises a processor, and memory coupled to said processor which encodes one or more programs. The programs encoded in memory cause the processor to perform the steps of the above methods wherein the expression profiles and information about physiological, pharmacological and disease states are received by the computer system as input. Computer systems may be used to execute the software of an embodiment of the invention (see, e.g., U.S. Pat. No. 5,733,729).

8. Providing Appropriate Treatment and Prevention Regimes to Patient

Upon a positive determination or confirmation that a patient has experienced a stroke, and a determination of the cause of stroke, e.g., using the biomarkers provided herein, the methods further provide for the step of prescribing, providing or administering a regime for the prophylaxis or treatment of ischemic stroke. By diagnosing the occurrence and/or the cause of stroke using the biomarkers described herein, a patient can rapidly receive treatment that is tailored to and appropriate for the type of stroke that has been experienced, or that the patient is at risk of experiencing.

If the expression levels of the plurality of biomarkers evaluated from Table 7A (and 7B) indicate the occurrence or risk of stroke, a positive diagnosis of stroke can be confirmed using methods known in the art. For example, the patient can be subject to MRI imaging of brain and vessels, additional blood tests, EKG, and/or echocardiogram.

If the expression levels of the plurality of biomarkers evaluated from Table 13A (and 13B) indicate the occurrence or risk of cardioembolic stroke, the patient can be prescribed or administered a regime of an anticoagulant. Exemplary anticoagulants include aspirin, heparin, warfarin, and dabigatran.

If the expression levels of the plurality of biomarkers evaluated from Table 14 indicate the occurrence or risk of carotid stenosis, the patient can be prescribed or administered a regime of an anti-platelet drug. The most frequently used anti-platelet medication is aspirin. An alternative to aspirin is the anti-platelet drug clopidogrel (Plavix). Some studies indicate that aspirin is most effective in combination with another anti-platelet drug. In some embodiments, the patient is prescribed a combination of low-dose aspirin and the anti-platelet drug dipyridamole (Aggrenox), to reduce blood clotting. Ticlopidine (Ticlid) is another anti-platelet medication that finds use. Patients having a moderately or severely narrowed neck (carotid) artery, may require or benefit from carotid endarterectomy. This preventive surgery clears carotid arteries of fatty deposits (atherosclerotic plaques) to prevent a first or subsequent strokes. In some embodiments, the patient may require or benefit from carotid angioplasty, or stenting. Carotid angioplasty involves using a balloon-like device to open a clogged artery and placing a small wire tube (stent) into the artery to keep it open.

If the expression levels of the plurality of biomarkers evaluated from Table 15 indicate the occurrence or risk of atrial fibrillation, the patient can be prescribed a regime of an anticoagulant (to prevent stroke) and/or a pharmacological agent to achieve rate control. Exemplary anticoagulants include aspirin, heparin, warfarin, and dabigatran. Exemplary rate control drugs include beta blockers (e.g., metoprolol, atenolol, bisoprolol), non-dihydropyridine calcium channel blockers (e.g., diltiazem or verapamil), and cardiac glycosides (e.g., digoxin).

9. Solid Supports and Kits

The invention further provides a solid supports comprising a plurality of nucleic acid probes that hybridize to a plurality (e.g., two or more, or all) of the genes set forth in Tables 7A, 7B, 13A, 13B, 14, 15, and optionally 16. For example, the solid support can be a microarray attached to a plurality of nucleic acid probes that hybridize to a plurality (e.g., two or more, or all) of the genes set forth in Table 7A, and optionally Table 16. For example, the solid support can be a microarray attached to a plurality of nucleic acid probes that hybridize to a plurality (e.g., two or more, or all) of the genes set forth in Table 13A, and optionally Table 16. For example, the solid support can be a microarray attached to a plurality of nucleic acid probes that hybridize to a plurality (e.g., two or more, or all) of the genes set forth in Table 14, and optionally Table 16. For example, the solid support can be a microarray attached to a plurality of nucleic acid probes that hybridize to a plurality (e.g., two or more, or all) of the genes set forth in Table 15, and optionally Table 16.

In various embodiments, the solid supports are configured to exclude genes not associated with or useful to the diagnosis, prediction or confirmation of a stroke or the causes of stroke. For example, genes which are overexpressed or underexpressed less than 1.2-fold in subjects having or suspected of having stroke, regardless of cause, in comparison to a control level of expression can be excluded from the present solid supports. In some embodiments, genes that are overexpressed or underexpressed less than 1.2-fold in subjects with ischemic stroke, including cardioembolic stroke, atherothrombotic stroke, and stroke subsequent to atrial fibrillation, in comparison to a control level of expression can be excluded from the present solid supports. The solid support can comprise a plurality of nucleic acid probes that hybridize to a plurality (e.g., two or more, or all) of the genes useful for the diagnosis of ischemic stroke, cardioembolic stroke, carotid stenosis, and/or atrial fibrillation, as described herein. As appropriate, nucleic acid probes that hybridize to a plurality (e.g., two or more, or all) of the genes useful for the diagnosis of ischemic stroke, cardioembolic stroke, carotid stenosis, and/or atrial fibrillation can be arranged in a predetermined array on the solid support. In various embodiments, nucleic acids not specifically identified and/or not relating to the diagnosis of and/or not associated with the diagnosis of ischemic stroke, cardioembolic stroke, carotid stenosis, and/or atrial fibrillation are not attached to the solid support. The solid support may be a component in a kit.

The invention also provides kits for diagnosing ischemia or a predisposition for developing ischemia. For example, the invention provides kits that include one or more reaction vessels that have aliquots of some or all of the reaction components of the invention in them. Aliquots can be in liquid or dried form. Reaction vessels can include sample processing cartridges or other vessels that allow for the containment, processing and/or amplification of samples in the same vessel. The kits may comprise a plurality of nucleic acid probes that hybridize to a plurality the genes set forth in Tables 7A, 7B, 13A, 13B, 14 and 15. In one embodiment, the kits comprise a plurality of nucleic acid probes that hybridize to a plurality of the genes set forth in Table 7A (and 7B). In one embodiment, the kits comprise a plurality of nucleic acid probes that hybridize to a plurality of the genes set forth in Table 13A (and 13B). In one embodiment, the kits comprise a plurality of nucleic acid probes that hybridize to a plurality of the genes set forth in Table 14. In one embodiment, the kits comprise a plurality of nucleic acid probes that hybridize to a plurality of the genes set forth in Table 15. The probes may be immobilized on an array as described herein.

In some embodiments, the kits comprise a solid support comprising a plurality of nucleic acid probes that hybridize to a plurality the genes set forth in Tables 7A, 7B, 13A, 13B, 14 and 15, and optionally Table 16. For example, the solid support can be a microarray attached to a plurality of nucleic acid probes that hybridize to a plurality the genes set forth in Tables 7A, 7B, 13A, 13B, 14 and 15, and optionally Table 16.

In addition, the kit can comprise appropriate buffers, salts and other reagents to facilitate amplification and/or detection reactions (e.g., primers, labels) for determining the expression levels of a plurality of the genes set forth in Tables 7A, 7B, 13A, 13B, 14 and 15. In one embodiment, the kit comprises appropriate buffers, salts and other reagents to facilitate amplification and/or detection reactions (e.g., primers, labels) for determining the expression levels of a plurality of the genes set forth in Table 7A (and 7B). In one embodiment, the kit comprises appropriate buffers, salts and other reagents to facilitate amplification and/or detection reactions (e.g., primers) for determining the expression levels of a plurality of the genes set forth in Table 13A (and 13B). In one embodiment, the kit comprises appropriate buffers, salts and other reagents to facilitate amplification and/or detection reactions (e.g., primers) for determining the expression levels of a plurality of the genes set forth in Table 14. In one embodiment, the kit comprises appropriate buffers, salts and other reagents to facilitate amplification and/or detection reactions (e.g., primers) for determining the expression levels of a plurality of the genes set forth in Table 15. The kits can also include written instructions for the use of the kit.

In one embodiment, the kits comprise a plurality of antibodies that bind to a plurality of the biomarkers set forth in Tables 7A, 7B, 13A, 13B, 14 and 15. The antibodies may or may not be immobilized on a solid support, e.g., an ELISA plate.

EXAMPLES

The following examples are offered to illustrate, but not to limit the claimed invention.

Example 1

Biomarkers for the Diagnosis of the Occurrence and/or Risk of Ischemic Stroke

Materials and Methods

The study had two objectives: (1) Demonstrate that the previously identified 29 probes distinguish IS from healthy controls [Tang Y et al., *J Cereb Blood Flow Metab.*, 26:1089-1102 (2006)] in a new cohort; and (2) Identify additional genes that discriminate IS from vascular risk factor (SAVVY) controls and myocardial infarction (MI) controls. Whole blood was drawn from IS patients (n=70, 199 samples) at ≤3, 5 and 24 hours (3 h IS, 5 h IS, 24 IS) as part of the CLEAR trial [Pancioli A M et al., *Stroke*, 39:3268-3276 (2008)] (NCT00250991 at Clinical-Trials.gov). IS subjects were treated with r-tPA with or without eptifibatide after the 3 h blood sample was obtained. Controls included healthy subjects (n=38), subjects with acute myocardial infarction (MI, n=17) and subjects with at least one cardiovascular risk factor (hypertension, diabetes mellitus, hyperlipidemia, or tobacco smoking) recruited from the SAVVY (Sex, Age and Variation in Vascular functionalitY) study (n=52). The institutional review board at each site approved the study, and each patient provided informed consent. Blood samples were collected in PAXgene tubes (PreAnlytix, Germany). Isolated RNA was processed using Ovation Whole Blood reagents (Nugen Technologies, San Carlos, Calif.) and hybridized onto Affymetrix Genome U133 Plus 2 GeneChips (Affymetrix Santa Clara, Calif.). Data was normalized using Robust Multichip Averaging (RMA) [Bolstad B M et al., *Bioinformatics*, 19:185-193 (2003)] and our internal-gene normalization approach. [Stamova B S et al., *BMC Med Genomics*, 2:49 (2009)]

Objective 1: The predictive ability of the 29 previously identified genes was determined using k-nearest neighbor in PAM (Prediction Analysis of Microarrays) [Tibshirani R et al., *Proc Natl Acad Sci USA*, 99:6567-6572 (2002)]. IS and healthy subjects were randomly split in half, stratified by Group and Time-Point (for the IS samples) into a Training Set to develop the prediction algorithm and an independent Test (Validation) Set for evaluating the accuracy of the prediction algorithm.

Objective 2: To identify genes able to discriminate between IS and all controls groups, an ANCOVA adjusted for age, gender and microarray batch effect was used. The numbers of predictive genes were minimized using the nearest-shrunken centroids algorithm (PAM). The ability of the identified genes to predict IS from controls was assessed using (1) 10-fold cross-validation (CV), and (2) assessed in a second (independent) Test (Validation) Set using several prediction algorithms (k-nearest neighbor (K-NN), support vector machine (SVM), linear discriminant analysis (LDA), and quadratic discriminant analysis (QDA)). Only the 3 h IS (not treated) and 24 h IS samples were analyzed for objective 2 since they were considered most clinically relevant. See supplementary materials and methods for details of the prediction and cross-validation analyses for Objectives 1 and 2.

Study Participants

Ischemic Stroke (IS) Patients

Participants with acute IS (n=68) were recruited from the CLEAR trial, a multicenter, randomized double blind safety study of recombinant tissue-plasminogen activator (r-tPA) and eptifibatide as previously described [Pancioli A M et al., Stroke, 39:3268-3276 (2008)] (NCT00250991 at ClinicalTrials.gov). Blood samples were collected at ≤3 hours (3 h IS), 5 hours (5 hr IS) and 24 hours (24 IS) following ischemic stroke onset. r-tPA, with or without eptifibatide, was administered following the 3 h blood draw. IS was diagnosed by a stroke neurologist with access to all clinical and diagnostic tests including neurovascular imaging data.

Control Groups

Vascular Risk Factor Subjects (SAVVY)

Subjects with at least one cardiovascular risk factor (hypertension, diabetes mellitus, hyperlipidemia, or tobacco smoking) were recruited from the SAVVY (Sex, Age and Variation in Vascular functionalitY) study (n=52). These subjects are referred to as vascular risk factor SAVVY Controls in the current study. Exclusion criteria were past history of cardiovascular disease (including stroke, coronary artery disease, peripheral artery disease or deep vein thrombosis), BMI>46 kg/m$^2$, history of cancer, chronic infection, autoimmune disease or blood dyscrasias.

Patients with Myocardial Infarction (MI)

Subjects with MI (n=16) were recruited from the University of California Davis Medical Center. The average time since the event was 58.0 h (range 19.3-176.5). All were treated acutely with anti-platelet drugs and an anticoagulant prior to the blood draw. Angioplasty (n=8) or CABG (n=1) were performed in some of the patients prior to the blood draw. No MI patient received r-tPA.

Healthy Controls

Healthy controls were recruited from the University of Cincinnati (n=15), UC Davis (n=3) and Stanford (n=20). These subjects had never been hospitalized, were on no medications, and had no known major medical, surgical or psychiatric diseases.

Baseline demographic data were compared between the previous [Tang Y et al., J Cereb Blood Flow Metab., 26:1089-1102 (2006)] and current study as well as between current IS and control subjects using Student's 2-tail t-test for continuous variables (age) and a $\chi^2$ or Fisher Exact tests for categorical variables (gender, race).

Probe-Level Data Analysis

Raw expression values of each probe from the Affymetrix U133 Plus 2.0 expression arrays were collapsed into probe set level data using Robust Multichip Averaging (RMA) normalization [Bolstad B M et al., Bioinformatics, 19:185-193 (2003)], as well as by modified internal-gene normalization (manuscript in preparation) to a subset of stably expressed internal genes [Stamova B S et al., BMC Med Genomics, 2:49 (2009)]. This involved Median Polishing summarization step, division of each individual gene expression value by the geometric mean of the reference genes, and log$_2$-transformation. For the analysis in Objective 1, both RMA and Internal control gene normalized values were used. For all the analysis of Objective 2, the derivation of the discriminatory genes was performed using the internal control gene normalized values. The same values were used in developing the Classifiers.

Batch Correction

Due to the unbalanced nature of the batches, bias is introduced when batch is used as a factor in an ANCOVA model. However, it is still desirable to account for the existing technical variation. This was accomplished by selecting genes that were common to the ANCOVA output sets with and without batch as a factor. While this technique introduced strict criteria for the selection of discriminating genes, it was intended to improve the chance of validation of the results upon subsequent studies and to achieve greater generalization, which can be translated into IS predictive clinical test.

Identification of Discriminatory Genes

Figure 3:
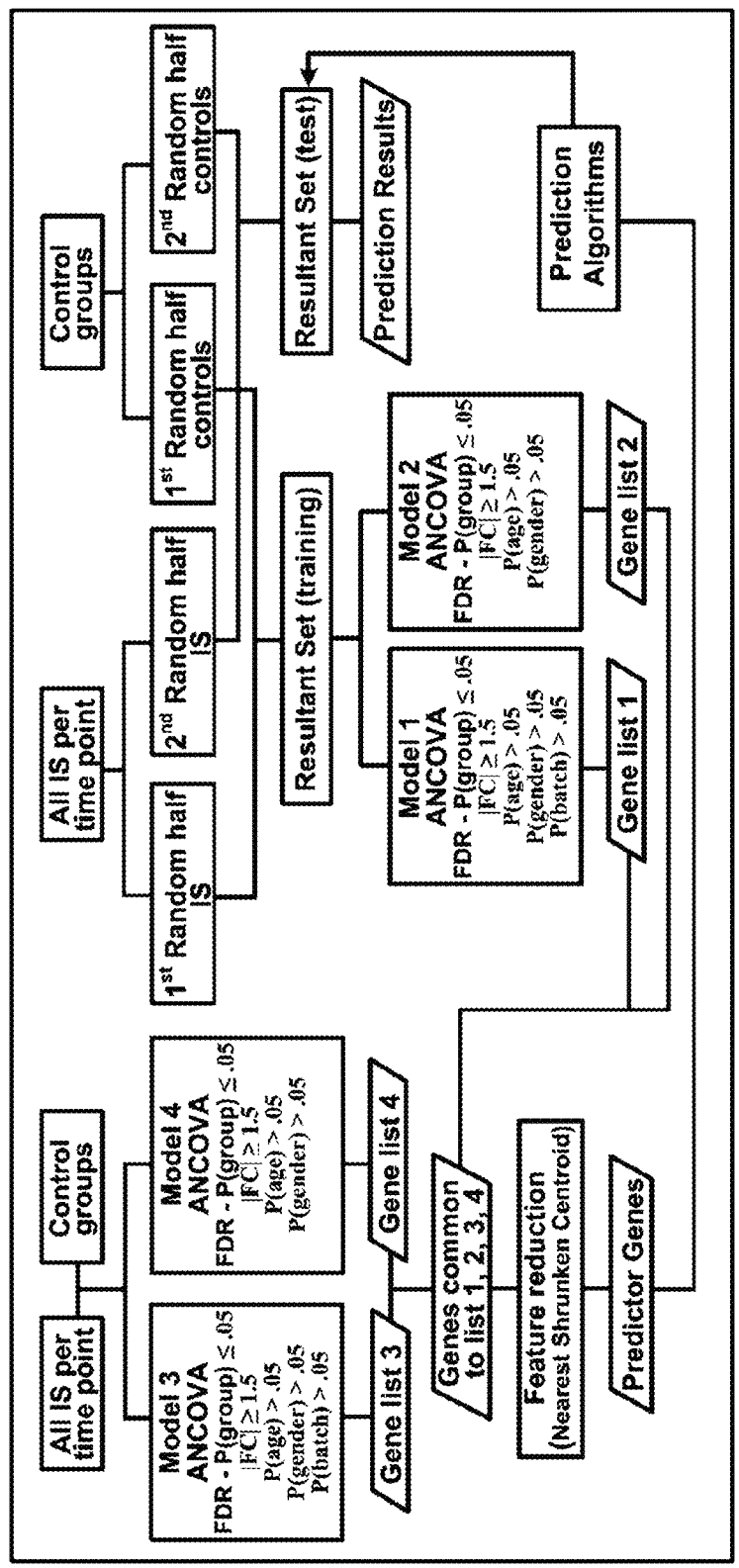
FIG. 3. Diagram of the analysis work flow for the identification of IS predictors.

Analysis of each comparison (IS per time-point (3 h and 24 h) vs Healthy, MI and SAVVY, respectively) was performed individually. The samples were randomly split, stratified by Group, in order to perform a split-sample analysis, where the Prediction Algorithms are trained on half of the samples (Training Set), and the performance of the Classifiers is tested on the second half of the samples (Test Set). The Analysis Workflow Chart is shown in FIG. 3. The feature selection for the derivation of the discriminatory genes between Healthy and IS at 3 h and IS at 24 h, respectively, involved finding common probe sets from four different ANCOVA analysis, referred to here as Models 1-4. All factors used in the analysis were common to all models (Group, Age, Gender) with the exception of Batch, which was only factored in Model 1 and 3. Models 1 and 2 were applied to a randomly selected one-half of the samples stratified by Group and time-point (for the IS samples) named here 1$^{st}$ random half, whereas Models 3 and 4 were applied to the complete data sets. Overlap of models with and without batch was performed due to the unbalanced nature of batches in an attempt to select more reliable probe sets. Overlap of complete-set and split-set models was performed to achieve greater generalization compared to the split set model which can be translated into IS predictive clinical test.

Gene lists satisfying the following criteria were developed: FDR-corrected p-value (Group)≤0.05 and fold-change ≤−1.5 or ≥1.5, as well as being not-significant for the rest of the factors (uncorrected p (Age)>0.5 and uncorrected p (Gender)>0.05 and, for the models including Batch, uncorrected p (Batch)>0.05). The goal is to find genes whose expressions are not affected by significant technical (batch), gender, or age effects.

Exception to Flow Chart Analysis for IS at 24 h vs Healthy was at Model 1, where the uncorrected p (Group) <0.01 was used to generate a larger gene list. Analysis of SAVVY vs IS at 3 h and IS at 24 h, respectively, included only Models 2 and 4, since Batch could not be factored in, due to the complete confounding of the batches. Analysis of MI vs IS at 3 h and IS at 24 h, respectively, included only Models 3 and 4, since the sample size of the MI patients was very small (n=17). In this case a 10-fold cross-validation procedure was used to determine the performance of the Classification Algorithms. If the number of the probe sets at the feature selection step was large, we proceeded with excluding probe sets not annotated, annotated as chromosomal segments, annotated as hypothetical proteins, probe sets which per Affimetrix annotation may potentially detect more than one unique gene (*_x_at, *_a_at, *_s_at), and exclusion of duplicates.

Predictions/Classification

Different prediction algorithms were used. Prediction Analysis of Microarrays (PAM) uses the K-nearest neighbor as a classification engine (default k=10) as well as nearest shrunken centroid as a feature-selection method [Tibshirani R et al., *Proc Natl Acad Sci USA*, 99:6567-6572 (2002)]. The differentially expressed genes that passed the criteria outlined above were input into PAM and the minimum numbers of genes with the optimal classification accuracy were selected. In addition, multiple other classification methods were evaluated in the analysis of the combined 3 h IS predictors, 24 h IS predictors and 3 h plus 24 h IS predictors in order to find an optimal model and to produce an unbiased estimate of prediction accuracy (analysis performed in Partek Genomics Suite, Partek Inc., St. Louis, Mich., USA). A combination of the ANCOVA models and nearest-shrunken centroids for our feature reduction step was used. In addition to PAM, the classification models used in this study were K-Nearest Neighbor (K-NN) with k=1, 3, 5, 7, and 9 number of neighbors with Euclidian Distance similarity measure; Nearest-Centroid (NC) with equal and proportional prior probabilities; Quadratic Discriminant Analysis (QDA) with equal and proportional prior probabilities, Linear Discriminant Analysis (LDA) with equal and proportional prior probabilities, and Support Vector Machine, constituting a 121-model space. For overview of these methods, see [Asyali M H et al., *Current Bioinformatics*, 1:55-73 (2006); Jain A K et al., Statistical pattern recognition: A review, IEEE Transactions On Pattern Analysis and Machine Intelligence., 22:4-37 (2000)]. 2-level nested cross-validation (CV) was performed to generate a less biased estimate of classification success (reported as accuracy (normalized) estimate). In this approach, an "outer" cross-validation is performed in order to produce an unbiased estimate of prediction error (by holding out samples as an independent test set). To select the optimal model to be applied to the held out test sample, additional "inner" cross-validation is performed on the training data (which is the data not held out as test data by the "outer" cross-validation). Full leave-one-out cross validation (CV) was used in cases where the complete set was used to train and CV the prediction accuracy.

For Table 4 in the Results section, the following parameters were used: *Accuracy (normalized) estimate of 121-Model Space=91.2% (80.3/88). Best Model: SVM (shrink=yes, cost=101, nu=0.5, tol=0.001, kern rbf deg=3, radial basis function (gamma)=0.01, coef=0.0). Kappa=0.83. †Accuracy (normalized) estimate of 121-Model Space=87.9% (76.4/87). Best Model: SVM (shrink=yes, cost=101, nu=0.5, tol=0.001, kern rbf deg=3, radial basis function (gamma)=0.0001, coef=0.0). Kappa=0.83. ‡Accuracy (normalized) estimate of 121-Model Space=91.2% (110/121). Best Model: SVM (shrink=yes, cost=701, nu=0.5, tol=0.001, kern rbf deg=3, radial basis function (gamma)=0.00001, coef=0.0). ||Correct classification at 3 h=76%, at 24 h=97%. #Correct classification at 3 h=94%, at 24 h=97%.

Gene Enrichment Analysis of Discriminatory Genes to Identify Biological Themes in the Combined 3 h and 24 h IS Predictors Ingenuity Pathway Analysis (IPA 8.0, Ingenuity® Systems) was used for identifying over-represented biological functions in the combined 97 probe set list of 3 h and 24 h predictors. A Fisher's exact test (p<0.1) was used to determine whether there was over representation of the 97 probe sets/genes in any given biological function. Gene ontology of the stroke predictors was extracted from Affymetrix NetAffix website (on the internet at affymetrix.com/user/login.jsp?toURL=-/analysis/netaffx/index.affx).

Results

Subject Demographics

Demographic information is presented in Table 1 (Objective 1) and Table 2 (Objective 2). Age was significantly different between IS and control groups (p<0.05) (Tables 1 and 2). Gender was significantly different (p<0.05) between IS and healthy subjects in the Tang et al, 2006 study [Tang Y et al., *J Cereb Blood Flow Metab.*, 26:1089-1102 (2006)] and the current study (Table 1), as well as between IS and Vascular Risk Factor (SAVVY) Control subjects from the current study (Table 2). Race was significantly different between IS compared to Healthy and MI controls (Table 2). Hypertension and diabetes were not significantly different between the groups.

TABLE 1

Demographic Summary of Subjects from our previous Tang et al. 2006 Study [Tang Y et al., *J Cereb Blood Flow Metab.*, 26: 1089-1102 (2006)] and our Current Study of Ischemic Stroke (IS) and Healthy Controls.

|  | IS Tang et. al, 2006 | Healthy Tang et. al, 2006 | IS Current Study | Healthy Controls Current Study |
|---|---|---|---|---|
| N | 15 | 15 | 70† | 38 |
| Mean Age, years (SD) | 64 ± 14 | 49 ± 11 | 66.8 ± 12.7 | 45.0 ± 19.8 |
| Gender, % | | | | |
| Male | 73.3 | 87.5* | 57.1 | 47.4* |
| Female | 26.7 | 12.5* | 42.9 | 52.6* |
| Race, % | | | | |
| Caucasian | 80.0 | 75.0 | 80.0 | 55.3 |
| African American | 20.0 | 0.0 | 20.0 | 15.8 |
| Other | 0.0 | 25.0 | 0.0 | 28.9 |
| NIH Stroke Scale | | | | |
| 1st Blood Draw (3 h) | 15 ± 7 | N/A | 14 ± 7 | N/A |
| 2nd Blood Draw (5 h) | 12 ± 8 | | 11 ± 8 | |
| 3rd Blood Draw (24 h) | 9 ± 7 | | 10 ± 8 | |

N = number of subjects.

†N = 67 at 3 h, 66 at 5 h, 66 at 24 h. 61 subjects had all three time points.

*Gender distribution significantly different (p < 0.05) between healthy subjects in the current study compared to the Tang et al. 20061 study and marginally different between IS subjects in the current study compared to the Tang et al. 2006 [Tang Y et al., *J Cereb Blood Flow Metab.*, 26: 1089-1102 (2006)] study.

TABLE 2

Demographic Summary of Current Study Participants.

| | IS | Healthy Controls | MI Controls | Vascular SAVVY Controls |
|---|---|---|---|---|
| N | 70† | 38 | 17 | 52 |
| Mean Age, years (SD) | 66.8 ± 12.7 | 45.0 ± 19.8 | 59.6 ± 12.2 | 56.2 ± 5.4 |
| Gender, % | | | | |
| Male | 57.1 | 47.4 | 70.6 | 32.7 |
| Female | 42.9 | 52.6 | 29.4 | 67.3* |
| Race, % | | | | |
| Caucasian | 80.0 | 55.3 | 47.1 | 86.5 |
| African American | 20.0 | 15.8 | 17.6 | 11.5 |
| Other | 0.0 | 28.9** | 35.3** | 2.0 |
| NIH Stroke Scale | | | | |
| 1$^{st}$ Blood Draw (3 h) | 14 ± 7 | N/A | N/A | N/A |
| 2$^{nd}$ Blood Draw (5 h) | 11 ± 8 | | | |
| 3$^{rd}$ Blood Draw (24 h) | 10 ± 8 | | | |

†N = 67 at 3 h, 66 at 5 h, 66 at 24 h. 61 subjects had all three time points;
*Gender distribution significantly different (p < 0.05) between Ischemic Stroke (IS) and Vascular Risk Factor (SAVVY) controls.
MI = myocardial infarction.
N = number of subjects.
**Race significantly different (p < 0.05) between IS compared to healthy and MI.

Figure 4:
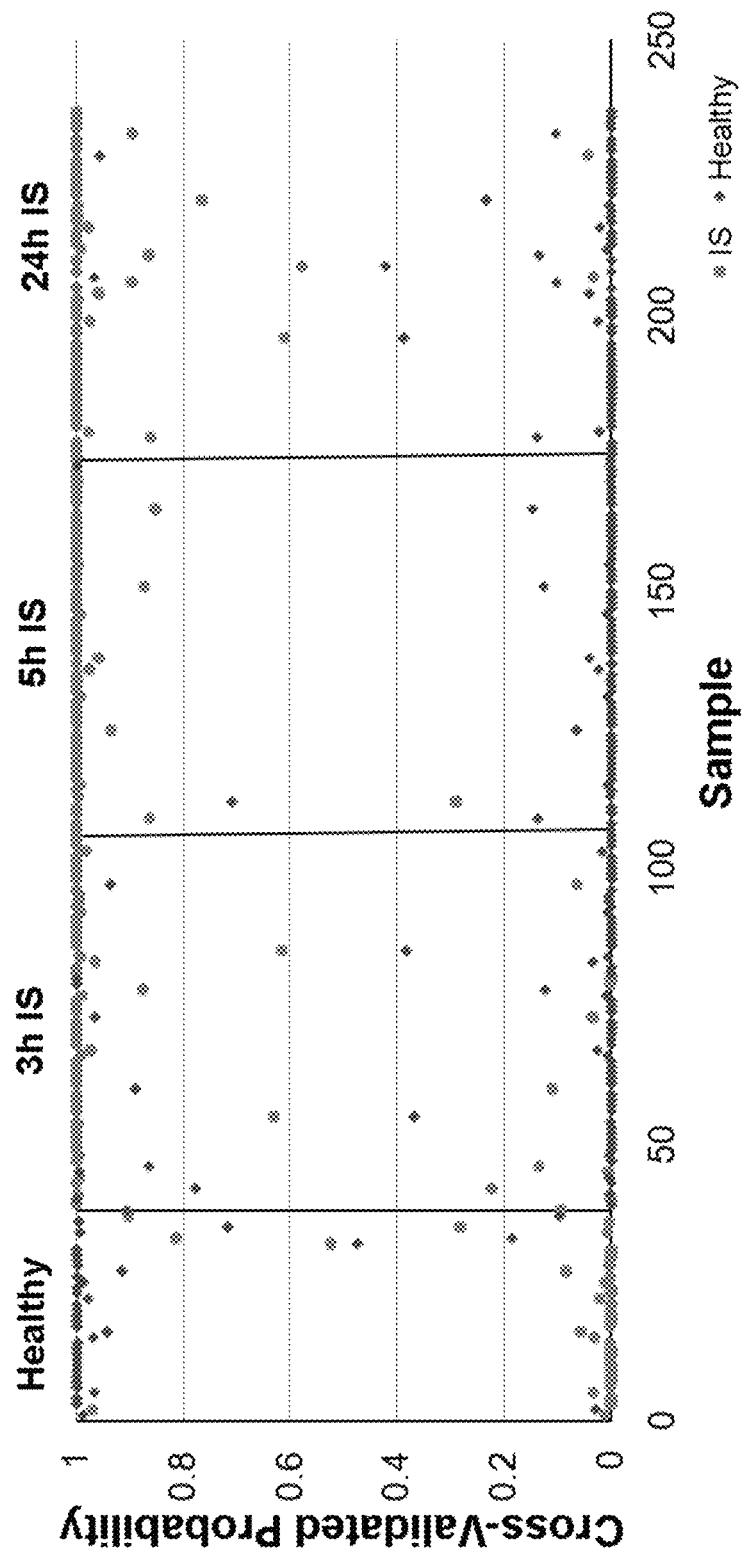
FIG. 4. PAM prediction accuracy of IS and healthy using the 29 probe set predictors of IS from Tang et al, 2006. The internal gene normalized expression values of all IS (n=70, 199 samples) and healthy (n=38) for the 29 IS predictors from Tang et al, 2006 were used as input in PAM. K-NN (number of neighbors n=10) threshold=0 (including all 29 predictors, and a 10-fold cross-validation was used to estimate prediction accuracy. X-axis represents sample number and the Y-axis represents cross-validated probability of diagnosis. A sample is considered misclassified if the predicted class does not match the known class with a probability greater than 0.5.

1) Replication of Tang et al, 2006 [Tang Y et al., *J Cereb Blood Flow Metab.*, 26:1089-1102 (2006)] IS Predictors in a Larger Cohort Due to the different array processing protocols in the study by Tang et al, 2006 [Tang Y et al., *J Cereb Blood Flow Metab.*, 26:1089-1102 (2006)] and the current studies, the following analyses were performed: (1) the prediction algorithm was retrained on the first random half of the new samples (Training Set) and the performance of the 29 probe sets evaluated in the second half (Test/Validation Set); and (2) the samples used in the Tang et al, 2006 study [Tang Y et al., *J Cereb Blood Flow Metab.*, 26:1089-1102 (2006)] and the current study were internal gene normalized. Overall, 92.9% sensitivity for IS and 94.7% specificity for healthy controls with high Test Set probabilities were achieved (FIG. 1, Table 3). The results are similar to the ability of these predictors to classify the previously published patients [Tang Y et al., *J Cereb Blood Flow Metab.*, 26:1089-1102 (2006)], with 88.9% sensitivity for IS and 100% specificity for healthy controls (Table 3). In addition, for comparison purposes to the previous study [Tang Y et al., *J Cereb Blood Flow Metab.*, 26:1089-1102 (2006)], RMA normalization and Cross-Validation (used in the previous study [Tang Y et al., *J Cereb Blood Flow Metab.*, 26:1089-1102 (2006)]) on our complete set of IS and healthy samples was performed. Similar results were obtained (Table 5 and FIG. 4).

TABLE 3

Validation of the of the 29 probe sets from the Tang et al. 2006 study [Tang Y et al., *J Cereb Blood Flow Metab.*, 26: 1089-1102 (2006)]. These probe sets were trained on the first half (Training Set) of the subjects in this study (n = 35 IS, n = 19 Healthy), and then used predict the Test Set probabilities on a second half of the ischemic stroke (IS) subjects (Test Set) (n = 35, 99 samples) and Healthy subjects (n = 19, 19 samples) in the Current Study. In addition, the same probe sets were used to predict the Test set probabilities on the original subjects in the Tang et al. 2006 study.

| Class Prediction | Study | 3 h | 5 h | 24 h | All Time Points |
|---|---|---|---|---|---|
| IS, Sensitivity, % | Tang et al, 2006 | 73.3 | 93.3 | 100 | 88.9 |
| | Current Study | 84.8 | 97.0 | 97.0 | 92.9 |
| Healthy, Specificity, % | Tang et al, 2006 | N/A | N/A | N/A | 100 |
| | Current Study | N/A | N/A | N/A | 94.7 |

Sensitivity = % correct classification of IS samples
Specificity = % correct classification of healthy samples

TABLE 4

Classification Accuracy (%) of 3 h and 24 h Ischemic Stroke (IS) Predictors. Half of the subjects (training set) were used to derive the IS Predictors. For the Test Set prediction accuracy estimate on the second half of the subjects, there were 3 h IS (n = 33), 24 h IS (n = 33), healthy (n = 19), Vascular Risk Factor (SAVVY) (n = 26) and MI (n = 8). The 60-probe set 3 h IS predictors represented the sum of the 3 h IS comparison to the three control groups: Healthy(17), SAVVY(22) and MI(31), of which 10 were common to the 3 h IS vs MI and 3 h IS vs SAVVY predictors, yielding 60 probe sets. The 46-probe set 24 h IS predictors represented the sum of the 24 h IS comparison to the three control groups: Healthy(20), SAVVY(9) and MI(17). The 3 h and 24 h IS Combined predictors represent the sum of the 3 h IS predictors (60) and 24 h IS predictors(46) of which 9 were common, yielding 97 probe sets.

| | 60 probe sets 3 h IS vs Controls (Healthy, MI, SAVVY) | | 46 probe sets 24 h IS vs Controls (Healthy, MI, SAVVY) | | 97 probe sets 3 h and 24 h IS Combined vs Controls (Healthy, MI, SAVVY) | |
|---|---|---|---|---|---|---|
| Group | PAM | SVM* | PAM | SVM† | PAM | SVM‡ |
| IS | 85 | 94 | 91 | 94 | 86∥ | 95# |
| SAVVY | 92 | 96 | 92 | 96 | 96 | 96 |
| MI | 88 | 88 | 63 | 50 | 75 | 75 |
| Healthy | 84 | 68 | 89 | 84 | 84 | 68 |

∥Correct classification at 3 h = 76%, at 24 h = 97%.
Correct classification at 3 h = 94%, at 24 h = 97%.

TABLE 5

Validation of the of the 29 probe sets from the Tang et al, 2006 study [Tang Y et al., *J Cereb Blood Flow Metab.*, 26: 1089-1102 (2006)]. Cross-validated Probabilities. Trained and cross-validated on current study samples (IS: n = 70, 199 samples) and Healthy (n = 38, 38 samples).

| Normalization Method | Class Prediction | Study | 3 h | 5 h | 24 h | All Time Points |
|---|---|---|---|---|---|---|
| RMA | IS, Sensitivity, % | Tang et al, 2006 | 66.7 | 86.7 | 100 | 84.4 |
| | | Current Study | 86.6 | 98.5 | 89.4 | 91.5 |

TABLE 5-continued

Validation of the of the 29 probe sets from the Tang et al, 2006 study [Tang Y et al., *J Cereb Blood Flow Metab.*, 26: 1089-1102 (2006)]. Cross-validated Probabilities. Trained and cross-validated on current study samples (IS: n = 70, 199 samples) and Healthy (n = 38, 38 samples).

| Normalization Method | Class Prediction | Study | 3 h | 5 h | 24 h | All Time Points |
|---|---|---|---|---|---|---|
| | Healthy, Specificity, % | Tang et al, 2006 | N/A | N/A | N/A | 100 |
| | | Current Study | N/A | N/A | N/A | 84.2 |
| Internal Genes | IS, Sensitivity, % | Tang et al, 2006 | 73.3 | 93.3 | 100 | 88.9 |
| | | Current Study | 86.6 | 98.5 | 95.5 | 93.5 |
| | Healthy, Specificity, % | Tang et al, 2006 | N/A | N/A | N/A | 100 |
| | | Current Study | N/A | N/A | N/A | 89.5 |

Figure 5:
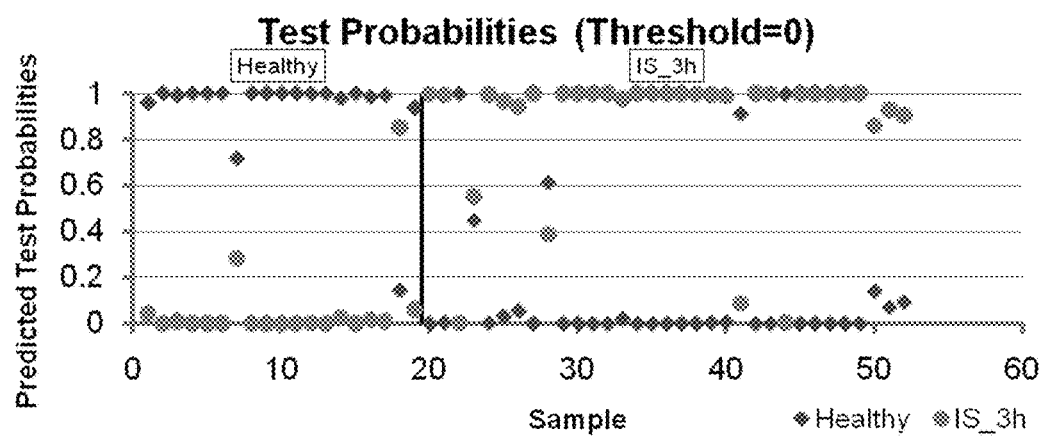
FIG. 5. PAM 3 h vs. Healthy test set+test set confusion matrix
Figure 6:
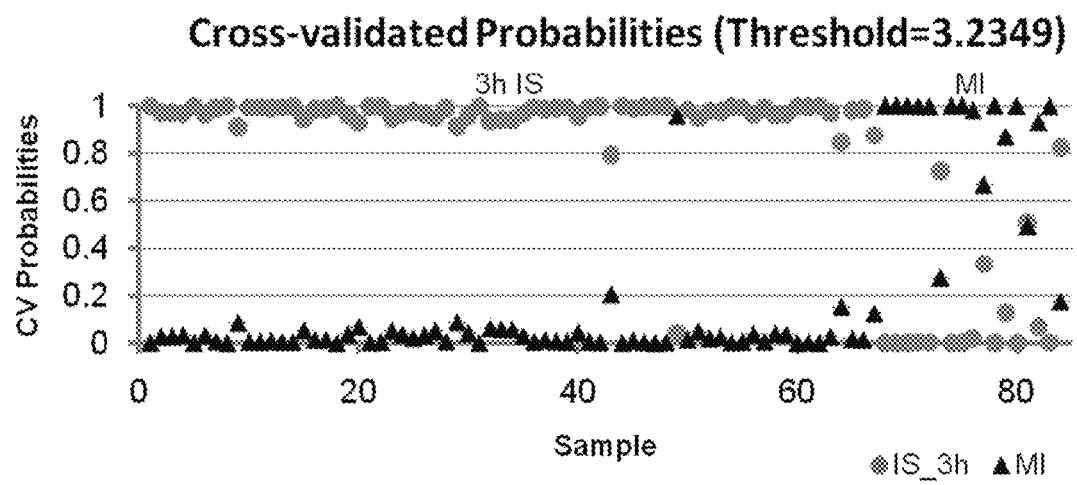
FIG. 6. PAM 3 h vs. MI CV+CV confusion matrix
Figure 7:
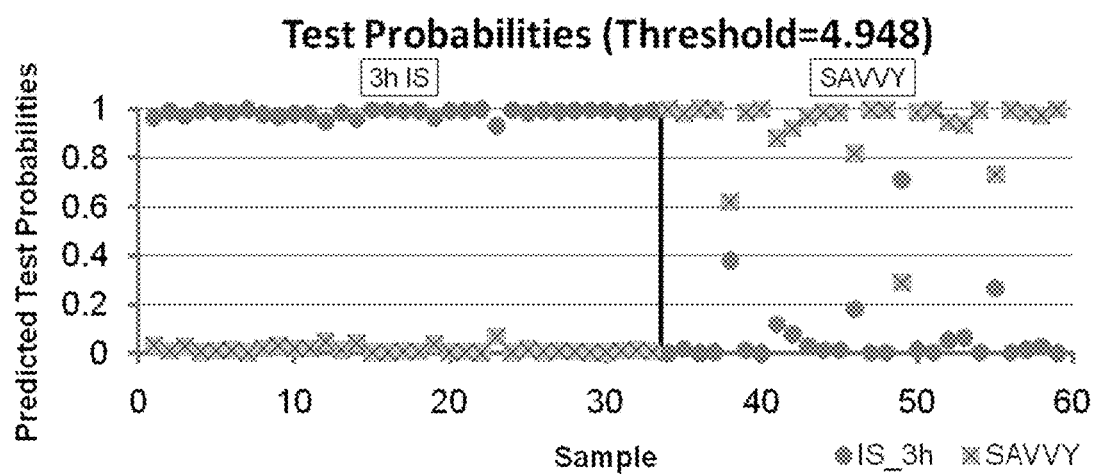
FIG. 7. PAM 3 h vs. SAVVY test set+test set confusion matrix

Sensitivity = % correct classification of IS samples
Specificity = % correct classification of healthy samples 2) Refinement of Prediction of IS Against Several Different Control Groups Differentiation of IS Patients from Controls Predictive gene expression signatures were derived individually for each comparison. To discriminate the 3 h IS group from the healthy (training set), MI (Cross Validation set, due to small sample size for MI), and SAVVY (training set) control groups, the PAM classification algorithm derived 17, 31, and 22 predictor probesets/genes, respectively. Putting these genes into PAM to predict the class of the subjects in the test groups yielded 87.9/94.7%, 98.5/82.4%, and 100/96.2% sensitivity/specificity for 3 h IS compared to healthy, MI and SAVVY control samples, respectively (FIGS. 5, 6 and 7, respectively).

Figure 8:
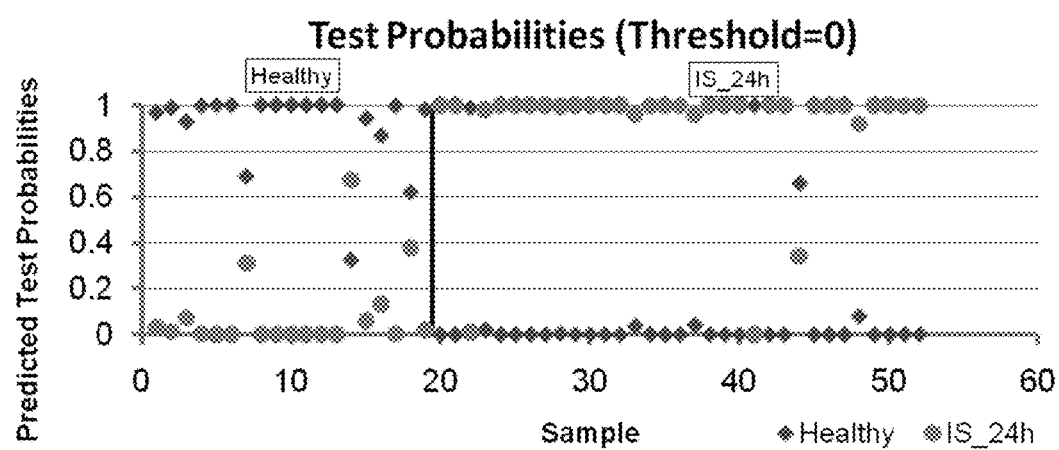
FIG. 8. PAM 24 h vs. healthy test set+test set confusion matrix
Figure 9:
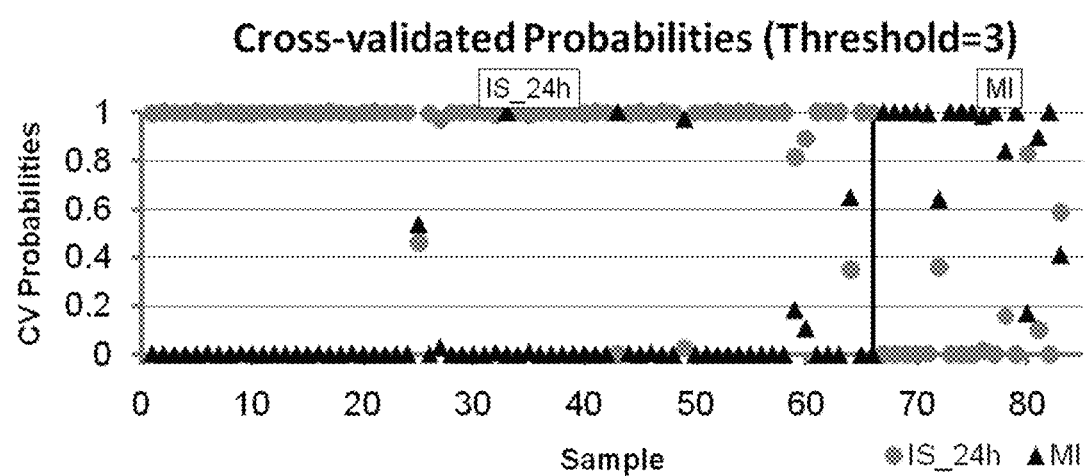
FIG. 9. PAM 24 h vs. MI CV+CV confusion matrix
Figure 10:
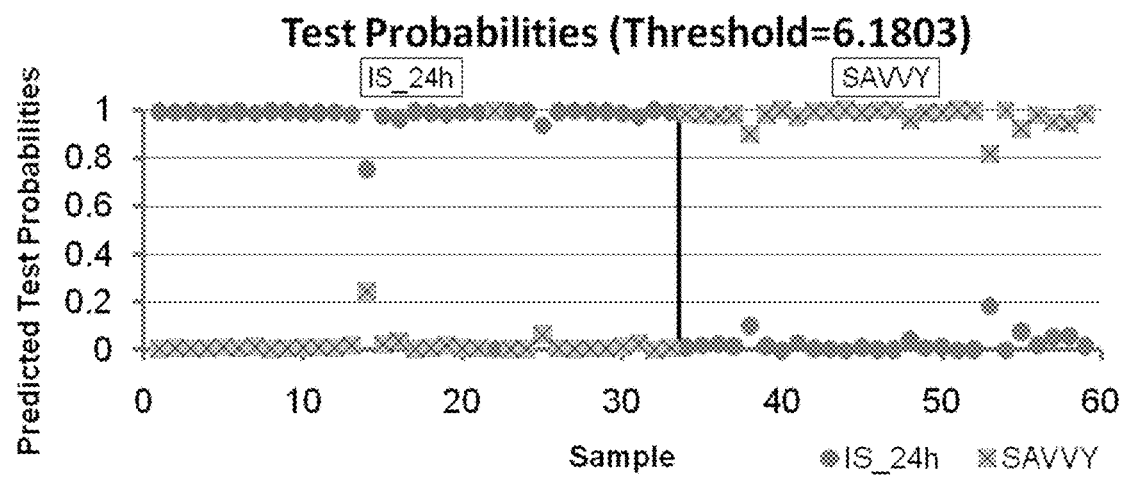
FIG. 10. PAM 24 h vs. SAVVY test set+test set confusion matrix

To discriminate the 24 h IS group from the healthy (training set), MI (CV set, due to small sample size for MI), and SAVVY (training set) control groups, the PAM classification algorithm derived 20, 19, and 9 predictor probesets/genes, respectively. Putting these genes into PAM to predict the class of the subjects in the test groups yielded 90.9/94.7%, 93.9/88.2%, and 97/100% sensitivity/specificity for 24 h IS compared to healthy, MI and SAVVY control samples, respectively (FIGS. 8, 9, and 10, respectively).

Figure 2:
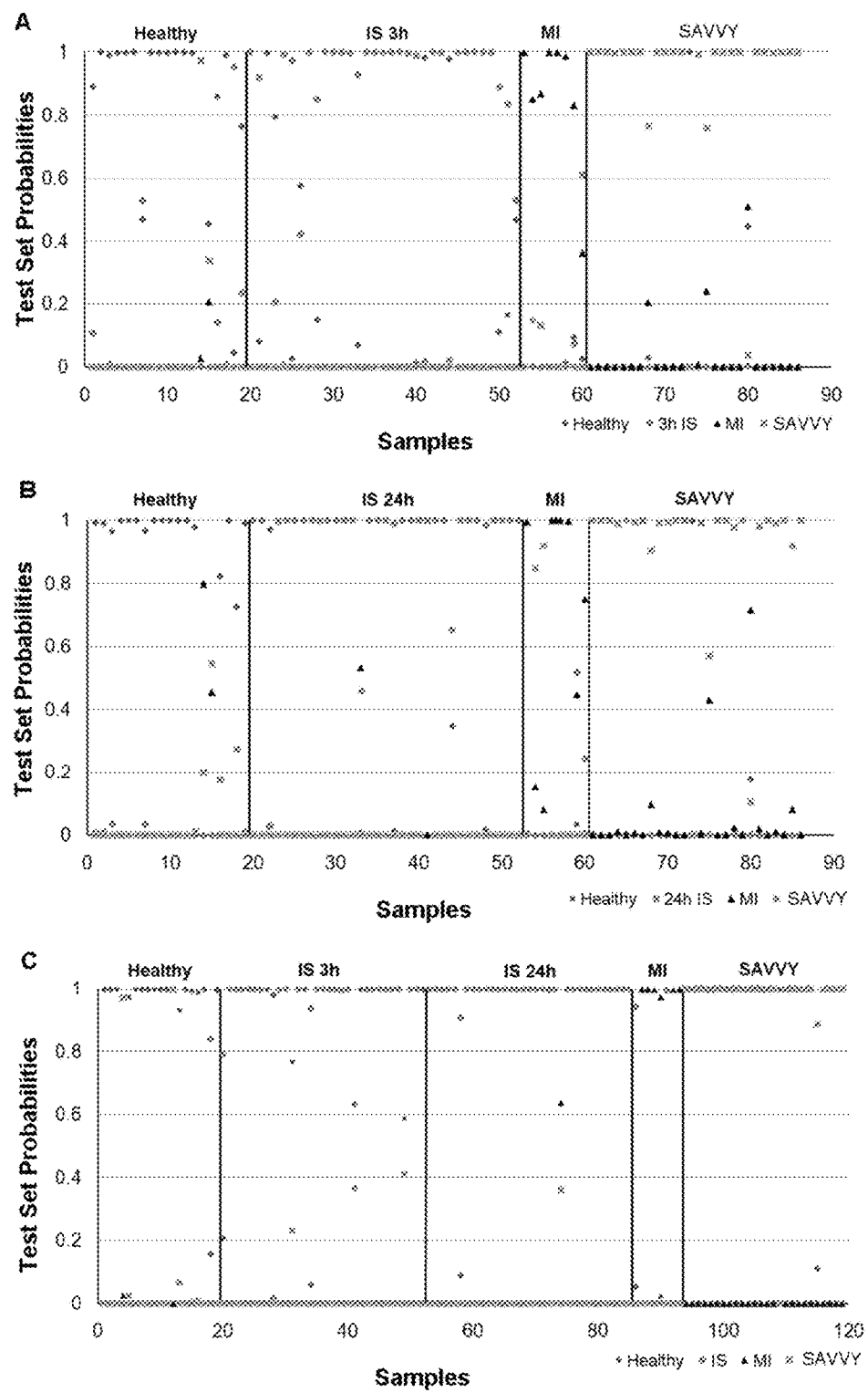
FIGS. 2A-C. PAM prediction accuracy of IS predictors in the current study. Prediction accuracy of the Test Set using PAM. Prediction Analysis of Microarrays (PAM) was used to perform the predictions (K-NN, neighbors n=10; threshold=0). For panels A, B and C the X-axis represents the patient sample number and the Y-axis represents Test Set probabilities. A sample is considered miss-classified if its correct class predicted probability is less than 0.5. The numbers of subjects in the Training Set were: 3 h IS n=34; 24 h IS n=33; SAVVY vascular controls n=26; and MI n=9. The numbers of subjects in the Test Set were: 3 h IS n=33; 24 h IS n=33; SAVVY n=26; and MI n=8. A. 3 h IS predictors. The 60-probe set predictors for 3 h IS (combined from comparisons of 3 h IS samples to healthy, MI and SAVVY samples from the Training Set) were put into PAM to predict the class of the Test Set subject samples by calculating the probability that they were in a given class. B. 24 h IS predictors. The 46-probe set predictors for 24 h IS (combined from comparisons of 24 h IS samples to healthy, MI and SAVVY samples from the Training Set) were put into PAM to predict the class of the Test Set subject samples by calculating the probability that they were in a given class. C. Combined 3 h and 24 h IS predictors. The 97-probe set predictors for 3 h IS and 24 h IS (combined from comparisons of 3 h IS and 24 h IS samples to healthy, MI and SAVVY samples from the Training Set) were put into PAM to predict the class of the Test Set subject samples by calculating the probability that they were in a given class.
Figure 11:
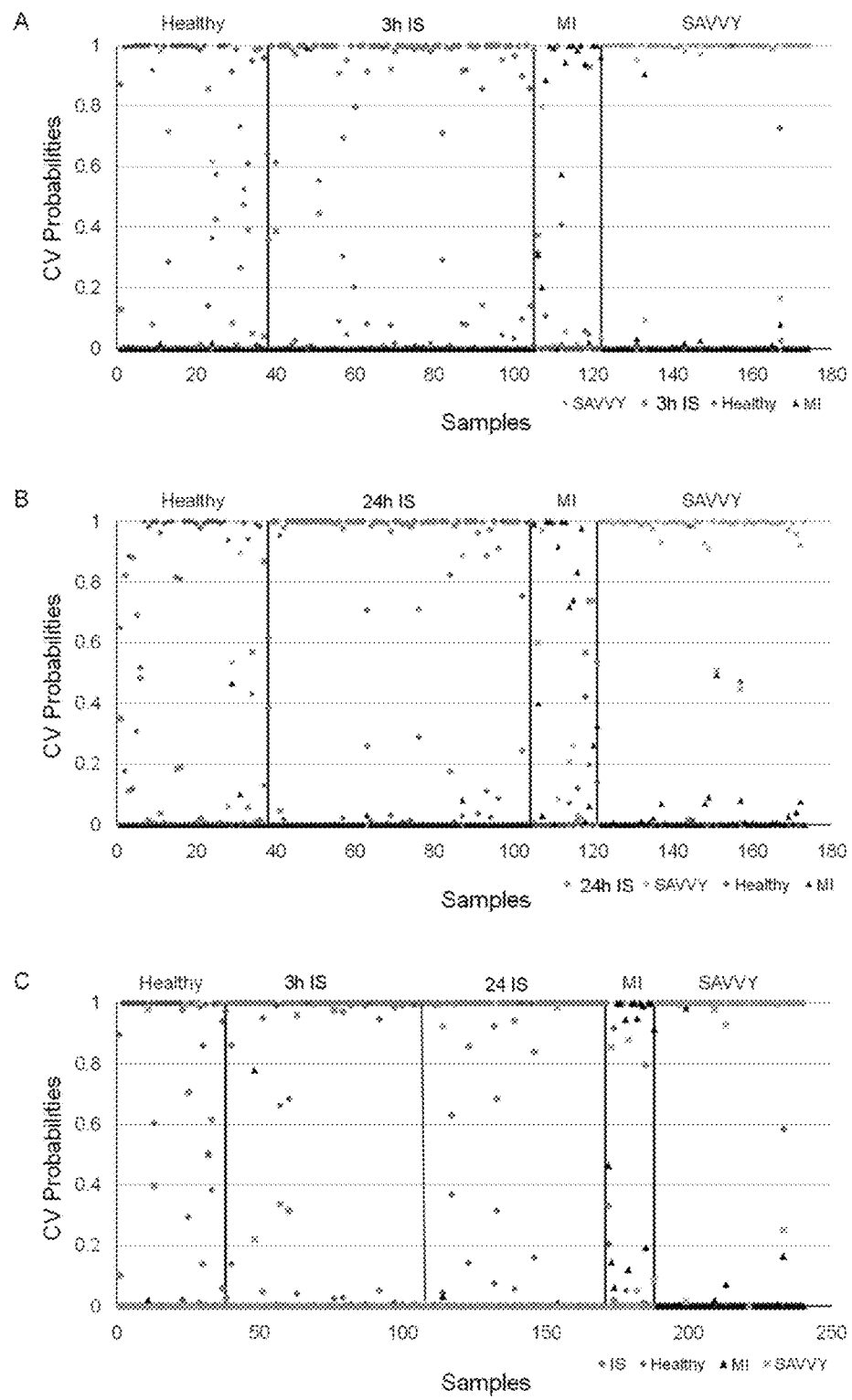
FIGS. 11A-C. PAM on Combined 3 h, 24 h and 3+24 h IS predictors. CV Probabilities.

Prediction Accuracy of 3 h IS Predictors on 3 h IS, Healthy, MI and SAVVY Subjects Combining the lists of the 3 h predictors from the individual comparison analyses yielded 60 unique probe sets representing 56 annotated genes. Their prediction probability using PAM on the Test Set is presented in FIG. 2A. The percent correctly predicted samples from PAM as well as the best performing prediction model (SVM) are presented in Table 4. Overall (normalized) accuracy was 91.2%. With SVM the sensitivity was 94% and specificities were 96% for SAVVY, 88% for MI, and 68% for healthy. Analysis in PAM produced lower sensitivity for IS but higher specificity for healthy subjects compared to SVM (Table 4). In addition to the split sample analysis, a 10-fold Cross Validation was performed which is a preferred method for developing and evaluating prediction algorithms for small sample sizes. This produced the expected better prediction results (Table 6 and FIG. 11A).

TABLE 6

Classification Accuracy (% correct classification) of 3 h and 24 h Ischemic Stroke (IS) Predictors.

| | 60 probe sets 3 h IS vs Controls (Healthy, MI, SAVVY) | | 46 probe sets 24 h IS vs Controls (Healthy, MI, SAVVY) | | 97 probe sets 3 h and 24 h IS Combined vs Controls (Healthy, MI, SAVVY) | |
|---|---|---|---|---|---|---|
| Group | PAM | SVM* | PAM | SVM† | PAM | SVM‡ |
| IS | 90 | 91 | 88 | 91 | 90∥ | 96 |
| SAVVY | 94 | 98 | 98 | 98 | 94 | 98 |
| MI | 71 | 88 | 65 | 82 | 71 | 82 |
| Healthy | 82 | 84 | 79 | 84 | 79 | 76 |

Sample sizes used for Cross-Validation were n = 67 at 3 h IS, n = 66 at 24 h IS, n = 52 for SAVVY, n = 17 for MI. Sample sizes used for split-sample prediction performance estimate on the test set were n = 33 at 3 h IS, n = 33 at 24 h IS, n = 26 for SAVVY, n = 8 for MI. The 60-probe set 3 h IS predictors represented the sum of the 3 h IS comparison to the three control groups: Healthy (17 probe sets), SAVVY controls (22 probe sets) and MI (31 probe sets). The 46-probe set 24 h IS predictors represented the sum of the 24 h IS comparison to the three control groups: Healthy (20 probe sets), SAVVY controls (9 probe sets) and MI (17 probe sets). The 3 h and 24 h IS Combined predictors represent the sum of the 3 h IS predictors (60 probe sets) and 24 h IS predictors (n = 46) of which 9 were common, thus yielding 97 probe sets.
*Accuracy (normalized) estimate of 121-Model Space = 86.4% (150/174). Best Model: SVM (shrink = yes, cost = 201, nu = 0.5, tol = 0.001, kern rbf deg = 3, radial basis function (gamma) = 0.001, coef = 0.0).
†Accuracy (normalized) estimate of 121-Model Space = 89.2% (154/173). Best Model: SVM (shrink = yes, cost = 201, nu = 0.5, tol = 0.001, kern rbf deg = 3, radial basis function (gamma) = 0.0001, coef = 0.0).
‡Accuracy (normalized) estimate of 121-Model Space = 88.2% (212/240). Best Model: SVM (shrink = yes, cost = 101, nu = 0.5, tol = 0.001, kern rbf deg = 3, radial basis function (gamma) = 0.01, coef = 0.0).
∥Correct classification at 3 h = 87%, at 24 h = 96%

Prediction Accuracy of 24 h IS Predictors on 24 h IS, Healthy, MI and SAVVY Subjects Combining the lists of the 24 h predictors from the individual comparison analyses yielded 46 unique probe sets representing 32 annotated genes. Their prediction probability using PAM on the Test Set is presented in FIG. 2B. The percent correctly predicted samples from PAM as well as SVM (best performing prediction model) are presented in Table 4. Overall (normalized) accuracy was 89.2%. With SVM the sensitivity was 94% and specificities were 96% for SAVVY, 50% for MI and 84% for healthy. Better results were again obtained using a 10-fold cross validation (Table 6 and FIG. 11B).

Prediction Accuracy of Combined 3 h and 24 IS Predictors on 3 h and 24 h IS, Healthy, MI and SAVVY Subjects Combining the lists of the 3 h and 24 h predictors from the individual comparison analyses yielded 97 unique probe sets representing 79 annotated genes. Their prediction probability using PAM on the Test Set is presented in FIG. 2C. The percent correctly predicted samples from PAM and SVM (best performing prediction model) are presented in Table 4. Overall (normalized) accuracy was 91.2%. With SVM the sensitivity was 95% and specificities were 96% for SAVVY, 75% for MI, and 68% for healthy. Analysis in PAM produced lower sensitivity for IS but higher specificity for healthy subjects compared to SVM (Table 4). Similarly, due to the small sample numbers of MI subjects, 10-fold cross-validation was performed which yielded somewhat better results (Table 6 and FIG. 11C).

IV. Main Biological Function of Biomarkers Described

Using Ingenuity Pathway analysis software (see Supplementary Materials) the coagulation system was the only statistically over-represented bio-function in the combined 97-probe set list of 3 h and 24 h IS predictors. The coagulation genes included coagulation factor V (proaccelerin, labile factor) (F5) and thrombomodulin (THBD). GO annotations and the complete list of predictors are presented in Tables 7A-C. Less stringent criteria yielded large numbers of genes with many more regulated pathways.

TABLE 7A

Combined 3 h and 24 h IS predictors - Identification of Genes
Table 7A. Biomarkers Useful to Predict the Occurrence of Stroke

| Probe Set ID | Gene Symbol | Gene Title | GenBank ID | UniGene ID | RefSeq Transcript ID | RefSeq Protein ID |
| --- | --- | --- | --- | --- | --- | --- |
| 1554560_at | PGM5 | phosphoglucomutase 5 | BC033073.1 | Hs.307835 | NM_021965 | NP_068800 |
| 1561271_at | CCDC144C /// LOC100134159 | coiled-coil domain containing 144C /// similar to Coiled-coil domain containing 144B | BC036241.1 | Hs.652797 | NR_023380 /// XM_001718261 | XP_001718313 |
| 207409_at | LECT2 | leukocyte cell-derived chemotaxin 2 | NM_002302.1 | Hs.512580 | NM_002302 | NP_002293 |
| 207570_at | SHOX | short stature homeobox | NM_000451.2 | Hs.105932 | NM_000451 /// NM_006883 | NP_000442 /// NP_006874 |
| 240715_at | TBX5 | T-box 5 | AW269421 | Hs.381715 | NM_000192 /// NM_080717 /// NM_080718 /// NM_181486 | NP_000183 /// NP_542448 /// NP_542449 /// NP_852259 |
| 220456_at | SPTLC3 | serine palmitoyltransferase, long chain base subunit 3 | NM_018327.1 | Hs.425023 | NM_018327 | NP_060797 |
| 232547_at | SNIP | SNAP25-interacting protein | BF062187 | Hs.448872 | NM_025248 | NP_079524 |
| 238447_at | RBMS3 | RNA binding motif, single stranded interacting protein | AA428240 | Hs.696468 | NM_001003792 /// NM_001003793 /// NM_014483 | NP_001003792 /// NP_001003793 /// NP_055298 |
| 242912_at | P704P | prostate-specific P704P | AI041215 | Hs.654289 | NM_001145442 | NP_001138914 |
| 222835_at | THSD4 | thrombospondin, type I, domain containing 4 | BG163478 | Hs.387057 | NM_024817 | NP_079093 |
| 236029_at | FAT3 | FAT tumor suppressor homolog 3 (*Drosophila*) | AI283093 | Hs.98523 | NM_001008781 | NP_001008781 |
| 1559545_at | SNRPN | small nuclear ribonucleoprotein polypeptide N | AI371649 | Hs.632166 | NM_003097 /// NM_022805 /// NM_022806 /// NM_022807 /// NM_022808 | NP_003088 /// NP_073716 /// NP_073717 /// NP_073718 /// NP_073719 |
| 1562089_at | GLYATL1 | glycine-N-acyltransferase-like 1 | BC013929.1 | Hs.616909 | NM_080661 | NP_542392 |
| 1563533_at | GADL1 | glutamate decarboxylase-like 1 | AL832766.1 | Hs.657052 | NM_207359 | NP_997242 |
| 203917_at | CXADR | coxsackie virus and adenovirus receptor | NM_001338.1 | Hs.634837 | NM_001338 | NP_001329 |
| 206048_at | OVOL2 | ovo-like 2 (*Drosophila*) | NM_021220.1 | Hs.661013 | NM_021220 | NP_067043 |
| 219104_at | RNF141 | ring finger protein 141 | NM_016422.1 | Hs.44685 | NM_016422 | NP_057506 |
| 219859_at | CLEC4E | C-type lectin domain family 4, member E | NM_014358.1 | Hs.236516 | NM_014358 | NP_055173 |
| 232739_at | SPIB | Spi-B transcription factor (Spi-1/PU.1 related) | AK025419.1 | Hs.437905 | NM_003121 | NP_003112 |
| 234243_at | BXDC5 | brix domain containing 5 | AL359584.1 | Hs.481202 | NM_025065 | NP_079341 |
| 226899_at | UNC5B | unc-5 homolog B (*C. elegans*) | AK022859.1 | Hs.522997 | NM_170744 | NP_734465 |
| 203167_at | TIMP2 | TIMP metallopeptidase inhibitor 2 | NM_003255.2 | Hs.633514 | NM_003255 | NP_003246 |
| 1554816_at | ASTN2 | astrotactin 2 | BC010680.1 | Hs.601562 | NM_014010 /// NM_198186 /// NM_198187 /// NM_198188 | NP_054729 /// NP_937829 /// NP_937830 /// NP_937831 |
| 1557895_at | FLJ35934 | FLJ35934 protein | BC033201.1 | Hs.375092 | XR_041166 | — |
| 1561079_at | ANKRD28 | ankyrin repeat domain 28 | BC035170.1 | Hs.335239 | NM_015199 | NP_056014 |
| 1561477_at | CCDC144A | coiled-coil domain containing 144A | BC034617.1 | — | NM_014695 | NP_055510 |
| 210800_at | TIMM8A | translocase of inner mitochondrial membrane 8 homolog A (yeast) | BC005236.1 | Hs.447877 | NM_001145951 /// NM_004085 | NP_001139423 /// NP_004076 |
| 211617_at | ALDOAP2 | aldolase A, fructose-bisphosphate pseudogene 2 | M21191.1 | Hs.652473 | — | — |
| 213371_at | LDB3 | LIM domain binding 3 | AI803302 | Hs.657271 | NM_001080114 /// NM_001080115 /// NM_001080116 /// NM_007078 | NP_001073583 /// NP_001073584 /// NP_001073585 /// NP_009009 |
| 214043_at | PTPRD | protein tyrosine phosphatase, receptor type, D | BF062299 | Hs.446083 | NM_001040712 /// NM_002839 /// NM_130391 /// NM_130392 /// NM_130393 | NP_001035802 /// NP_002830 /// NP_569075 /// NP_569076 /// NP_569077 |

TABLE 7A-continued

Combined 3 h and 24 h IS predictors - Identification of Genes
Table 7A. Biomarkers Useful to Predict the Occurrence of Stroke

| Probe Set ID | Gene Symbol | Gene Title | GenBank ID | UniGene ID | RefSeq Transcript ID | RefSeq Protein ID |
|---|---|---|---|---|---|---|
| 214375_at | LOC729222 /// PPFIBP1 | similar to PTPRF interacting protein binding protein 1 /// PTPRF interacting protein, binding protein 1 (liprin beta 1) | AI962377 | Hs.172445 | NM_003622 /// NM_177444 /// XR_015484 /// XR_037707 /// XR_037871 | NP_003613 /// NP_803193 |
| 220351_at | CCRL1 | chemokine (C-C motif) receptor-like 1 | NM_016557.1 | Hs.310512 | NM_016557 /// NM_178445 | NP_057641 /// NP_848540 |
| 222264_at | HNRNPUL2 | heterogeneous nuclear ribonucleoprotein U-like 2 | BG167570 | Hs.714969 | NM_001079559 | NP_001073027 |
| 224403_at | FCRL4 | Fc receptor-like 4 | AF343661.1 | Hs.120260 | NM_031282 | NP_112572 |
| 228260_at | ELAVL2 | ELAV (embryonic lethal, abnormal vision, *Drosophila*)-like 2 (Hu antigen B) | AL161628 | Hs.166109 | NM_004432 | NP_004423 |
| 229073_at | PRTG | protogenin homolog (*Gallus gallus*) | AA912476 | Hs.130957 | NM_173814 | NP_776175 |
| 239309_at | DLX6 | distal-less homeobox 6 | T65128 | Hs.249196 | NM_005222 | NP_005213 |
| 40284_at | FOXA2 | forkhead box A2 | AB028021 | Hs.155651 | NM_021784 /// NM_153675 /// XM_002345401 | NP_068556 /// NP_710141 /// XP_002345442 |
| 220232_at | SCD5 | stearoyl-CoA desaturase 5 | NM_024906.1 | Hs.379191 | NM_001037582 /// NM_024906 | NP_001032671 /// NP_079182 |
| 242344_at | GABRB2 | gamma-aminobutyric acid (GABA) A receptor, beta 2 | AA772920 | Hs.303527 | NM_000813 /// NM_021911 | NP_000804 /// NP_068711 |
| 1559520_at | GYPA | Glycophorin A (MNS blood group) | AL833104.1 | Hs.434973 | NM_002099 | NP_002090 |
| 215285_s_at | PHTF1 | putative homeodomain transcription factor 1 | AA927671 | Hs.655824 | NM_006608 | NP_006599 |
| 219161_s_at | CKLF | chemokine-like factor | NM_016951.2 | Hs.15159 | NM_001040138 /// NM_016326 /// NM_016951 /// NM_181640 /// NM_181641 | NP_001035228 /// NP_057410 /// NP_058647 /// NP_857591 /// NP_857592 |
| 221058_s_at | CKLF | chemokine-like factor | NM_016326.2 | Hs.15159 | NM_001040138 /// NM_016326 /// NM_016951 /// NM_181640 /// NM_181641 | NP_001035228 /// NP_057410 /// NP_058647 /// NP_857591 /// NP_857592 |
| 221524_s_at | RRAGD | Ras-related GTP binding D | AF272036.1 | Hs.31712 | NM_021244 | NP_067067 |
| 222934_s_at | CLEC4E | C-type lectin domain family 4, member E | BC000715.1 | Hs.236516 | NM_014358 | NP_055173 |
| 223451_s_at | CKLF | chemokine-like factor | AF096895.2 | Hs.15159 | NM_001040138 /// NM_016326 /// NM_016951 /// NM_181640 /// NM_181641 | NP_001035228 /// NP_057410 /// NP_058647 /// NP_857591 /// NP_857592 |
| 227948_at | FGD4 | FYVE, RhoGEF and PH domain containing 4 | AI949549 | Hs.117835 | NM_139241 | NP_640334 |
| 235479_at | CPEB2 | cytoplasmic polyadenylation element binding protein 2 | AI948598 | Hs.656937 | NM_182485 /// NM_182646 | NP_872291 /// NP_872587 |
| 236297_at | — | — | AI420817 | Hs.585479 | — | — |
| 236898_at | LOC100290882 | similar to hCG1994130 | AW242604 | — | XM_002347794 | XP_002347835 |
| 238903_at | UBXN2B | UBX domain protein 2B | AI636090 | Hs.155572 | NM_001077619 | NP_001071087 |
| 207691_x_at | ENTPD1 | ectonucleoside triphosphate diphosphohydrolase 1 | NM_001776.1 | Hs.719076 | NM_001098175 /// NM_001164178 /// NM_001164179 /// NM_001164181 /// NM_001164182 /// NM_001164183 /// NM_001776 | NP_001091645 /// NP_001157650 /// NP_001157651 /// NP_001157653 /// NP_001157654 /// NP_001157655 /// NP_001767 |
| 205715_at | BST1 | bone marrow stromal cell antigen 1 | NM_004334.1 | — | NM_004334 | NP_004325 |
| 236172_at | LTB4R | leukotriene B4 receptor | AW206817 | Hs.567248 | NM_001143919 /// NM_181657 | NP_001137391 /// NP_858043 |
| 231029_at | F5 | coagulation factor V (proaccelerin, labile factor) | AI740541 | Hs.30054 | NM_000130 | NP_000121 |
| 202146_at | IFRD1 | interferon-related developmental regulator 1 | AA747426 | Hs.7879 | NM_001007245 /// NM_001550 | NP_001007246 /// NP_001541 |
| 206017_at | KIAA0319 | KIAA0319 | NM_014809.1 | Hs.26441 | NM_014809 | NP_055624 |
| 218177_at | CHMP1B | chromatin modifying protein 1B | AA293502 | Hs.656244 | NM_020412 | NP_065145 |
| 220122_at | MCTP1 | multiple C2 domains, transmembrane 1 | NM_024717.1 | Hs.655087 | NM_001002796 /// NM_024717 | NP_001002796 /// NP_078993 |

TABLE 7A-continued

Combined 3 h and 24 h IS predictors - Identification of Genes
Table 7A. Biomarkers Useful to Predict the Occurrence of Stroke

| Probe Set ID | Gene Symbol | Gene Title | GenBank ID | UniGene ID | RefSeq Transcript ID | RefSeq Protein ID |
|---|---|---|---|---|---|---|
| 220528_at | VNN3 | vanin 3 | NM_018399.1 | Hs.183656 | NM_001024460 /// NM_018399 /// NM_078625 /// NR_028290 /// NR_028291 | NP_001019631 /// NP_060869 /// NP_523239 |
| 226258_at | AMN1 | antagonist of mitotic exit network 1 homolog (S. cerevisiae) | BG031897 | Hs.591146 | NM_001113402 /// NR_004854 | NP_001106873 |
| 226671_at | LAMP2 | lysosomal-associated membrane protein 2 | AI150000 | Hs.496684 | NM_001122606 /// NM_002294 /// NM_013995 | NP_001116078 /// NP_002285 /// NP_054701 |
| 228220_at | FCHO2 | FCH domain only 2 | AI627666 | Hs.719247 | NM_001146032 /// NM_138782 | NP_001139504 /// NP_620137 |
| 229817_at | ZNF608 | zinc finger protein 608 | AI452715 | Hs.266616 | NM_020747 | NP_065798 |
| 235699_at | REM2 | RAS (RAD and GEM)-like GTP binding 2 | H19232 | Hs.444911 | NM_173527 | NP_775798 |
| 236154_at | QKI | Quaking homolog, KH domain RNA binding (mouse) | R41907 | Hs.593520 | NM_006775 /// NM_206853 /// NM_206854 /// NM_206855 | NP_006766 /// NP_996735 /// NP_996736 /// NP_996737 |
| 236613_at | RBM25 | RNA binding motif protein 25 | BE466195 | Hs.531106 | NM_021239 | NP_067062 |
| 239108_at | FAR2 | Fatty acyl CoA reductase 2 | H16791 | Hs.719237 | NM_018099 | NP_060569 |
| 213355_at | ST3GAL6 | ST3 beta-galactoside alpha-2,3-sialyltransferase 6 | AI989567 | Hs.148716 | NM_006100 | NP_006091 |
| 243201_at | HNRNPH2 | Heterogeneous nuclear ribonucleoprotein H2 (H') | BF061744 | Hs.632828 | NM_001032393 /// NM_019597 | NP_001027565 /// NP_062543 |
| 214987_at | GAB1 | GRB2-associated binding protein 1 | AL049449.1 | Hs.80720 | NM_002039 /// NM_207123 | NP_002030 /// NP_997006 |
| 208883_at | UBR5 | ubiquitin protein ligase E3 component n-recognin 5 | BF515424 | Hs.591856 | NM_015902 | NP_056986 |
| 228480_at | VAPA | VAMP (vesicle-associated membrane protein)-associated protein A, 33 kDa | AW296039 | Hs.699980 | NM_003574 /// NM_194434 | NP_003565 /// NP_919415 |
| 1556834_at | — | — | BC042986.1 | Hs.562766 | — | — |
| 1561754_at | — | — | AF086134.1 | Hs.671185 | — | — |
| 1561856_at | — | — | BC030088.1 | Hs.398148 | — | — |
| 1562084_at | — | — | BC042866.1 | Hs.571857 | — | — |
| 1562527_at | LOC283027 | hypothetical protein LOC283027 | AF519622.1 | Hs.710809 | — | — |
| 1569539_at | — | — | BC037935.1 | Hs.650514 | — | — |
| 1569664_at | — | — | BC035915.1 | Hs.622886 | — | — |
| 230959_at | — | — | AW072078 | Hs.656184 | — | — |
| 231597_x_at | — | — | AI371550 | — | — | — |
| 231598_x_at | — | — | AI379823 | — | — | — |
| 235606_at | LOC344595 | hypothetical LOC344595 | AA417117 | Hs.655735 | NR_028301 /// NR_028302 /// XM_001128525 /// XM_002345686 /// XM_943541 | XP_001128525 /// XP_002345727 /// XP_948634 |
| 238370_x_at | RPL22 | Ribosomal protein L22 | AI252081 | Hs.554762 | NM_000983 | NP_000974 |
| 243489_at | — | — | BF514098 | Hs.678608 | — | — |
| 244723_at | LOC100129488 | hypothetical protein LOC100129488 | BF510430 | Hs.656497 | XM_001724110 /// XM_001724617 | XP_001724162 /// XP_001724669 |
| 240331_at | — | — | AI820961 | Hs.658892 | — | — |
| 238375_at | RPL22 | Ribosomal protein L22 | AI820887 | Hs.554762 | NM_000983 | NP_000974 |
| 1554730_at | MCTP1 | multiple C2 domains, transmembrane 1 | BC030005.1 | Hs.655087 | NM_001002796 /// NM_024717 | NP_001002796 /// NP_078993 |
| 211565_at | SH3GL3 | SH3-domain GRB2-like 3 | AF036272.1 | Hs.666365 | NM_003027 /// NR_026799 | NP_003018 |

TABLE 7B

Combined 3 h and 24 h IS predictors - Identification of Additional Genes

| Probe Set ID | Gene Symbol | Gene Title | GenBank ID | UniGene ID | RefSeq Transcript ID | RefSeq Protein ID |
|---|---|---|---|---|---|---|
| 203505_at | ABCA1 | ATP-binding cassette, sub-family A (ABC1), member 1 | AF285167.1 | Hs.719214 | NM_005502 | NP_005493 |
| 1569476_at | DKFZP434L187 | hypothetical LOC26082 | BC033224.1 | Hs.652128 | NR_026771 | — |
| 226982_at | ELL2 | elongation factor, RNA polymerase II, 2 | AI745624 | Hs.192221 | NM_012081 | NP_036213 |
| 208158_s_at | OSBPL1A | oxysterol binding protein-like 1A | NM_018030.1 | Hs.370725 | NM_018030 /// NM_080597 | NP_060500 /// NP_542164 |
| 237252_at | THBD | thrombomodulin | AW119113 | Hs.2030 | NM_000361 | NP_000352 |

TABLE 7C

Combined 3 h and 24 h IS predictors - Fold Change in Expression

| Gene Symbol | GenBank ID | Fold Change (Stroke_3 h vs Healthy) | Fold Change (Stroke_24 h vs Healthy) | Fold Change (Stroke_3 h vs MI) | Fold Change (Stroke_24 h vs MI) | Fold Change (Stroke_3 h vs Vascular RF) | Fold Change (Stroke_24 h vs Vascular RF) |
|---|---|---|---|---|---|---|---|
| ABCA1 | AF285167.1 | 2.07119 | 2.2176 | 1.09826 | 1.31812 | 2.53649 | 2.82053 |
| PGM5 | BC033073.1 | −1.02257 | 1.0524 | −2.95407 | −1.70705 | −2.71273 | −2.09609 |
| CCDC144C /// LOC100134159 | BC036241.1 | −1.10901 | 1.33794 | −3.34373 | −1.89213 | −3.74796 | −2.67466 |
| LECT2 | NM_002302.1 | −1.02083 | 1.37036 | −2.59881 | −1.71369 | −4.29623 | −2.98873 |
| SHOX | NM_000451.2 | −1.14389 | 1.11225 | −2.767 | −1.72507 | −3.06805 | −2.39484 |
| TBX5 | AW269421 | −1.03714 | 1.19129 | −3.0574 | −2.27761 | −3.06348 | −2.47297 |
| SPTLC3 | NM_018327.1 | −1.14707 | −1.03685 | −2.19854 | −1.83648 | −3.30052 | −2.75386 |
| SNIP | BF062187 | −1.17632 | 1.08103 | −3.82871 | −3.06017 | −5.6754 | −4.47024 |
| RBMS3 | AA428240 | −1.12009 | 1.02386 | −2.45005 | −1.70022 | −3.16789 | −2.60285 |
| P704P | AI041215 | −1.05604 | 1.00723 | −2.43469 | −2.22274 | −2.01936 | −1.86268 |
| THSD4 | BG163478 | −1.08685 | 1.12498 | −4.69322 | −2.63617 | −3.79344 | −3.11379 |
| FAT3 | AI283093 | 1.01071 | 1.24955 | −3.79842 | −2.32779 | −4.30382 | −3.5885 |
| SNRPN | AI371649 | −1.08724 | 1.34813 | −4.11683 | −2.74804 | −3.4562 | −2.56379 |
| GLYATL1 | BC013929.1 | −1.02659 | 1.15432 | −2.02763 | −1.33612 | −3.17767 | −2.50921 |
| GADL1 | AL832766.1 | 1.08821 | 1.07407 | −2.11355 | −1.52718 | −3.08374 | −2.61596 |
| DKFZP434L187 | BC033224.1 | −1.51544 | −1.14093 | −2.31467 | −1.58952 | −3.11353 | −2.53751 |
| CXADR | NM_001338.1 | 1.0038 | 1.24866 | −2.17672 | −1.37969 | −2.59518 | −1.96103 |
| OVOL2 | NM_021220.1 | −1.00245 | 1.2244 | −2.6229 | −1.90303 | −3.73623 | −3.11322 |
| RNF141 | NM_016422.1 | 1.41652 | 1.76732 | −1.2503 | 1.0572 | 2.50809 | 2.88426 |
| CLEC4E | NM_014358.1 | 2.20581 | 1.74528 | 1.48355 | 1.23558 | 3.20009 | 2.54377 |
| ELL2 | AI745624 | 1.55833 | 1.55667 | −1.1485 | 1.01227 | 2.61216 | 2.75015 |
| SPIB | AK025419.1 | −1.49579 | −1.1927 | −1.30814 | −1.21513 | −3.13558 | −2.57627 |
| BXDC5 | AL359584.1 | −1.12459 | 1.0218 | −3.37543 | −2.16061 | −4.34359 | −3.47716 |
| UNC5B | AK022859.1 | −1.06322 | 1.08493 | −1.82774 | −1.59757 | −2.97215 | −2.38636 |
| TIMP2 | NM_003255.2 | 1.28723 | 1.29348 | 1.17202 | 1.27056 | 2.65311 | 2.63656 |
| ASTN2 | BC010680.1 | −1.03518 | 1.32302 | −3.91463 | −2.04726 | −2.20417 | −1.67438 |
| FLJ35934 | BC033201.1 | −1.06005 | 1.08555 | −1.7712 | −1.53152 | −2.90353 | −2.69988 |
| ANKRD28 | BC035170.1 | 1.02142 | 1.52112 | −3.23102 | −1.72253 | −3.75956 | −2.19095 |
| CCDC144A | BC034617.1 | −1.04089 | 1.40116 | −2.58087 | −1.9595 | −2.94944 | −2.15249 |
| TIMM8A | BC005236.1 | 1.05795 | 1.1857 | −3.61689 | −2.51479 | −3.9091 | −3.38927 |
| ALDOAP2 | M21191.1 | −1.00693 | 1.18023 | −2.05999 | −1.4251 | −2.14058 | −1.77344 |
| LDB3 | AI803302 | −1.02467 | 1.31867 | −2.4936 | −1.58633 | −2.80843 | −2.24309 |
| PTPRD | BF062299 | 1.13646 | 1.22444 | −2.58721 | −2.91802 | −2.00587 | −1.70565 |
| LOC729222 /// PPFIBP1 | AI962377 | −1.01017 | 1.07748 | −2.45679 | −2.23759 | −3.62343 | −2.8743 |
| CCRL1 | NM_016557.1 | 1.06414 | 1.45982 | −2.599 | −1.47982 | −2.2814 | −1.54199 |
| HNRNPUL2 | BG167570 | −1.1163 | −1.0024 | 2.22518 | 2.22789 | −1.33616 | −1.19626 |
| FCRL4 | AF343661.1 | 1.07525 | 1.21448 | −2.78886 | −1.89115 | −2.49879 | −2.24799 |
| ELAVL2 | AL161628 | −1.01813 | 1.21927 | −2.20416 | −1.49881 | −1.86331 | −1.56998 |
| PRTG | AA912476 | −1.04494 | 1.0727 | −2.3894 | −1.62453 | −2.99348 | −2.50635 |
| DLX6 | T65128 | 1.00215 | 1.1532 | −2.11674 | −1.46511 | −1.95595 | −1.70623 |
| FOXA2 | AB028021 | −1.0925 | −1.03101 | −2.1882 | −1.81159 | −1.99843 | −1.7749 |
| SCD5 | NM_024906.1 | −1.03966 | 1.02948 | −2.87609 | −1.91564 | −2.53071 | −2.01041 |
| GABRB2 | AA772920 | 1.04696 | 1.32428 | −2.28193 | −1.33566 | −1.78517 | −1.39109 |
| GYPA | AL833104.1 | 1.04745 | 1.30732 | −2.41685 | −1.59859 | −1.67937 | −1.39989 |
| OSBPL1A | NM_018030.1 | 1.69237 | 2.0161 | 1.00357 | 1.22861 | 1.80349 | 2.07533 |
| PHTF1 | AA927671 | 1.72132 | 1.82978 | −1.11534 | 1.20764 | 1.90827 | 2.12932 |
| CKLF | NM_016951.2 | 1.49288 | 1.67299 | −1.083 | 1.05107 | 1.77407 | 1.85927 |
| CKLF | NM_016326.2 | 1.74019 | 1.92981 | −1.09886 | 1.052 | 1.87206 | 1.89616 |
| RRAGD | AF272036.1 | 1.64361 | 1.82266 | −1.00147 | 1.30328 | 1.59064 | 1.74087 |
| CLEC4E | BC000715.1 | 1.72855 | 1.61958 | 1.25076 | 1.17072 | 1.52696 | 1.35715 |
| CKLF | AF096895.2 | 1.59532 | 1.72012 | −1.10928 | 1.00131 | 1.64747 | 1.65053 |
| FGD4 | AI949549 | 2.18122 | 1.77306 | 1.22089 | 1.20979 | 2.35983 | 1.917 |

TABLE 7C-continued

Combined 3 h and 24 h IS predictors - Fold Change in Expression

| Gene Symbol | GenBank ID | Fold Change (Stroke_3 h vs Healthy) | Fold Change (Stroke_24 h vs Healthy) | Fold Change (Stroke_3 h vs MI) | Fold Change (Stroke_24 h vs MI) | Fold Change (Stroke_3 h vs Vascular RF) | Fold Change (Stroke_24 h vs Vascular RF) |
|---|---|---|---|---|---|---|---|
| CPEB2 | AI948598 | 1.60268 | 1.66275 | 1.15005 | 1.40965 | 1.7109 | 1.90031 |
| — | AI420817 | 1.55624 | 1.60124 | −1.28503 | 1.01626 | 1.77952 | 2.0373 |
| LOC100290882 | AW242604 | 1.92911 | 2.33974 | −1.89614 | −1.13965 | 2.98199 | 3.56684 |
| UBXN2B | AI636090 | 1.74169 | 1.9441 | −1.11509 | 1.21234 | 1.70517 | 1.89673 |
| ENTPD1 | NM_001776.1 | 1.71167 | 1.76733 | −1.21194 | −1.07299 | 1.73969 | 1.87582 |
| BST1 | NM_004334.1 | 1.53532 | 1.62794 | −1.06879 | 1.06228 | 1.26326 | 1.34039 |
| LTB4R | AW206817 | 1.80645 | 1.74035 | 1.15737 | 1.21072 | 1.71929 | 1.59047 |
| F5 | AI740541 | 2.14346 | 2.2038 | −1.11679 | 1.43859 | 2.20136 | 2.347 |
| IFRD1 | AA747426 | 1.47432 | 1.73008 | −1.34744 | 1.06181 | 1.31407 | 1.4635 |
| KIAA0319 | NM_014809.1 | 1.63362 | 1.97771 | −1.05306 | 1.43649 | 1.46648 | 1.73293 |
| CHMP1B | AA293502 | 1.40135 | 1.80505 | −1.3705 | −1.09633 | 1.18349 | 1.53651 |
| MCTP1 | NM_024717.1 | 1.58307 | 1.95238 | −1.1366 | 1.10386 | 1.53504 | 1.96499 |
| VNN3 | NM_018399.1 | 1.99343 | 1.93901 | 1.07486 | 1.19707 | 1.96766 | 1.8831 |
| AMN1 | BG031897 | 1.7461 | 2.0847 | −1.39916 | 1.07802 | 1.95345 | 2.38444 |
| LAMP2 | AI150000 | 1.55435 | 1.79845 | −1.13336 | 1.11498 | 1.66826 | 1.84881 |
| FCHO2 | AI627666 | 1.63852 | 2.28796 | −2.06562 | −1.09689 | 1.6281 | 2.30861 |
| ZNF608 | AI452715 | 1.83637 | 4.23691 | −1.64571 | 1.60438 | 1.757 | 4.09293 |
| REM2 | H19232 | 1.51731 | 1.67729 | −1.41824 | −1.10004 | 1.24838 | 1.35338 |
| QKI | R41907 | 1.71321 | 2.0559 | −1.66896 | −1.18819 | 1.49767 | 1.98251 |
| RBM25 | BE466195 | 1.61161 | 1.82166 | −1.39912 | −1.08457 | 1.43618 | 1.81597 |
| FAR2 | H16791 | 1.31592 | 1.85091 | −1.43408 | 1.12536 | 1.15805 | 1.86642 |
| ST3GAL6 | AI989567 | 1.38604 | 2.22775 | −1.83273 | −1.10403 | 1.27982 | 2.05433 |
| HNRNPH2 | BF061744 | 1.5212 | 1.69734 | −1.34191 | −1.10041 | 1.42575 | 1.58788 |
| GAB1 | AL049449.1 | 1.20963 | 1.46575 | −1.09271 | 1.28122 | 1.60125 | 1.95743 |
| UBR5 | BF515424 | 1.48189 | 1.85612 | −1.61547 | −1.08548 | 1.34557 | 1.71885 |
| VAPA | AW296039 | 1.63693 | 1.7318 | −1.19576 | 1.07236 | 1.6695 | 1.83796 |
| THBD | AW119113 | 1.59427 | 2.17248 | −1.25924 | 1.19969 | 2.00552 | 2.50204 |
| — | BC042986.1 | 1.01757 | 1.24549 | −3.49838 | −2.38168 | −3.50237 | −2.86054 |
| — | AF086134.1 | −1.11298 | 1.08518 | −4.34061 | −3.27948 | −7.60167 | −5.23956 |
| — | BC030088.1 | −1.05299 | 1.36405 | −5.35944 | −2.82975 | −5.70757 | −4.37802 |
| — | BC042866.1 | 1.02169 | 1.23725 | −6.2228 | −3.34786 | −5.66994 | −4.21957 |
| LOC283027 | AF519622.1 | −1.02208 | 1.17339 | −4.87073 | −3.15597 | −3.09193 | −2.23434 |
| — | BC037935.1 | −1.18515 | −1.10026 | −4.36438 | −3.29567 | −6.29072 | −4.67834 |
| — | BC035915.1 | −1.16002 | −1.00454 | −3.4789 | −2.32404 | −5.06879 | −3.9396 |
| — | AW072078 | −1.13183 | −1.03534 | −2.5817 | −2.45432 | −2.97149 | −2.42805 |
| — | AI371550 | −1.2797 | −1.00935 | −5.39252 | −3.15227 | −6.53552 | −4.91151 |
| — | AI379823 | −1.43222 | −1.11788 | −7.45042 | −4.9032 | −8.79656 | −6.41832 |
| LOC344595 | AA417117 | −1.12772 | −1.04434 | −3.36106 | −2.70588 | −4.60892 | −3.38362 |
| RPL22 | AI252081 | −1.29183 | 1.00176 | −10.6787 | −5.52024 | −13.1426 | −9.07862 |
| — | BF514098 | −1.3354 | −1.14637 | −7.15023 | −4.63994 | −7.02866 | −5.73683 |
| LOC100129488 | BF510430 | −1.29144 | 1.03103 | −5.98942 | −3.38109 | −10.5201 | −8.12763 |
| — | AI820961 | −1.03836 | 1.07016 | −4.96218 | −3.43895 | −4.54929 | −3.90039 |
| RPL22 | AI820887 | −1.41083 | −1.1041 | −10.3524 | −5.84457 | −7.0436 | −5.09597 |
| MCTP1 | BC030005.1 | 1.65623 | 2.02722 | −1.04349 | 1.29446 | 2.71543 | 3.28561 |
| SH3GL3 | AF036272.1 | 1.01474 | −1.0085 | −5.88871 | −3.48898 | −6.30725 | −4.45099 |

Discussion

Diagnosis of ischemic stroke is based on clinical impression combined with brain imaging. However, in the acute setting, brain imaging is not always readily accessible, and clinical evaluation by persons experienced in stroke is not always readily available. In such patients, a blood test could be of use to diagnose ischemic stroke (IS). Several protein biomarkers have been associated with IS, but in the acute setting these have not yet shown sufficient sensitivity nor specificity to be clinically useful [Whiteley W et al., Stroke, 39:2902-2909 (2008); Foerch C et al., Neurology, 73:393-399 (2009); Jensen M B et al., Expert Rev Cardiovasc Ther., 7:389-393 (2009)]. In this study we show that gene expression profiles can be used as biomarkers of IS, replicated our previous findings, and refined the gene expression signature of IS by including more relevant control groups.

A 29-probe set profile was previously reported that distinguished IS from healthy controls [Tang Y et al., J Cereb Blood Flow Metab., 26:1089-1102 (2006)]. When this profile was used to predict a larger cohort of patients in this study, it distinguished IS from healthy subjects with a sensitivity of 92.9% and specificity of 94.7%. This is important in that it represents a validation of the concept that gene expression profiles can identify patients with stroke. Replication of gene expression profiles has been a challenge in the field, in large part due to false discovery associated with performing multiple comparisons. Robust biological responses and careful analyses made it possible to validate this 29-probe set profile in this study.

To obtain more biologically useful predictors of IS, gene profiles that distinguish IS from patients with vascular risk factors (RF) and myocardial infarction (MI) were identified. Using the individual group comparisons, the diagnosis of IS compared to the vascular risk factor group with over 95% sensitivity and specificity was predicted. Using the individual group comparisons, patients with IS from MI with over 90% sensitivity and over 80% specificity were differentiated. Biologically, this suggests at least some differences in the immune responses to infarction in brain and heart.

The 3 hour time point was a focus of most comparisons because this represents the critical time when decisions are made regarding acute therapy such as thrombolysis. Thus, for the development of a point-of-care test, this time period is when gene expression profiles could be of greatest use. With the 60-probe set signature, at the 3 hour time point, correct classification rates of 85-94%, 92-96%, 88% and 68-84% for IS, vascular risk factor, MI and healthy controls, respectively, was achieved. These are approaching clinical useful ranges.

Though RNA profiles were the focus in this study, the identified genes could be used as a guide in the evaluation of protein biomarkers for ischemic stroke. Genes for Factor 5 and throbomodulin were both identified as differentially expressed in IS compared to controls. Both of these molecules have also been identified as proteins associated with IS [Tang Y et al., *J Cereb Blood Flow Metab.*, 26:1089-1102 (2006); Moore D F et al., *Circulation*, 111:212-221 2005; Kozuka K et al., *Atherosclerosis*, 161:161-168 (2002)].

The goal of this study was not to identify all differentially expressed genes between IS and controls, but rather identify sets of genes whose patterns of expression may be useful for stroke prediction. As a result, these analyses have excluded large numbers of differentially expressed genes that are biologically relevant in IS. These will be the subject of future studies. Limitations of this study include (1) lack of stroke "mimics" in the control groups (2) lack of validation by qRT-PCR which would likely be used for clinical applications (3) the confounding treatment effects in the 5 h and 24 h blood samples from IS patients (4) race was not factored in due to different distributions with zero subjects in some of the race categories and (5) age is a confounder that was addressed by factoring it in ANCOVA models and by selecting control groups with close age distribution to the IS patients.

Example 2

Biomarkers for the Diagnosis of the Cause of Ischemic Stroke

1. Study Patients

Patients with acute ischemic stroke were enrolled from the CLEAR trial, a multicenter, randomized double-blind safety study of recombinant tissue-plasminogen activator (rt-PA) and eptifibatide as previously described [Pancioli A M et al., *Stroke*, 39:3268-3276 (2008)] (NCT00250991 at Clinical-Trials.gov). The institutional review board of each site approved the study protocol and written informed consent was obtained from each patient prior to study entry. Eligible patients had a diagnosis of acute ischemic stroke, therapy initiated within 3 hours of stroke onset, a National Institutes of Health Stroke Scale (NIHSS)>5, and were 18-80 years of age. All patients had standardized clinical evaluations, including NIHSS, and brain imaging. Blood samples were drawn into PAXgene tubes (PreAnalytiX, Hilden, Germany) at ≤3 hours, 5 hours, and 24 hours after stroke onset for use in gene expression analysis. A total of 194 samples were obtained from 76 patients.

Etiology of ischemic stroke was classified according to TOAST [Adams H P, Jr., et al., *Stroke*, 24:35-41 (1993)]. Patients with cardioembolic stroke, large vessel stroke and cryptogenic stroke (undetermined etiology) were included for study. Cardioembolic stroke required at least one source of cardiac embolus to be identified and the exclusion of large vessel or small vessel causes of stroke. Large vessel stroke required stenosis greater than 50% of ipsilateral extracranial or intracranial artery and the exclusion of cardioembolic and small vessel causes of stroke. Cause of stroke was determined using medical history, blood tests, brain imaging, Doppler and vascular angiography, and cardiac investigations. Patients with atrial fibrillation were identified using electrocardiogram, echocardiogram and 24-48 hour cardiac monitoring. Control blood samples were drawn from 23 control subjects similar in age, gender and race to stroke subjects. These subjects had no history of ischemic stroke or cardiovascular disease, no recent infection and no hematological disease.

2. Sample Processing

Whole blood was collected from the antecubital vein into PAXgene tubes (PreAnalytiX, Germany). PAXgene tubes were frozen at −80° C. after 2 hours at room temperature. All samples were processed in the same laboratory. Total RNA was isolated according to the manufacturer's protocol (PAXgene blood RNA kit; Pre-AnalytiX). RNA was analyzed using Agilent 2100 Bioanalyzer for quality and Nano-Drop (Thermo Fisher) for concentration. Samples required A260/A280 absorbance ratios of purified RNA ≥2.0 and 28S/18S rRNA ratios ≥1.8. Reverse transcription, amplification, and sample labeling were carried out using Nugen's Ovation Whole Blood Solution (Nugen Technologies, San Carlos, Calif.). Each RNA sample was hybridized according to manufacturer's protocol onto Affymetrix Human U133 Plus 2.0 GeneChips (Affymetrix Santa Clara, Calif.), which contain 54,697 probe sets. The arrays were washed and processed on a Fluidics Station 450 and then scanned on a Genechip Scanner 3000. Samples were randomly assigned to microarray batch stratified by cause of stroke.

3. Gene Expression Profile Analyses

Raw expression values (probe level data) were imported into Partek software (Partek Inc., St. Louis, Mo.). They were log transformed and normalized using RMA (Robust Multichip Average) and our previously reported internal gene normalization method [Stamova B S et al., *BMC Med Genomics*, 2:49 (2009)]. Statistical analysis, principal components analysis, and hierarchical unsupervised clustering analysis were performed with Partek Genomics Suite 6.04. The fidelity of genetic biomarker subsets as class prediction tools was established using k-nearest neighbor and 10-fold leave-one-out cross-validation in PAM (Prediction Analysis of Microarrays) [Tibshirani R J and Efron B., *Stat Appl Genet Mol Biol.*, 1:Article 1 (2002)]. Leave-one-out cross-validation provides a relatively unbiased estimate of the generalization ability of the genetic classifier. A model is generated on 90% of the samples and used to predict the remaining 10% of samples. The procedure is repeated 10 times to compute the overall error in the model. Ingenuity Pathway Analysis (IPA, Ingenuity Systems®, www.ingenuity.com) was used to determine whether the numbers of genes regulated within given pathways or cell functions were greater than expected by chance (Fisher's exact test).

4. Statistical Analyses

Differences in demographic data between groups were analyzed using Fisher's exact test and a two-tailed t-test where appropriate. All data are presented as mean±standard error. To identify the gene expression profiles that distinguish cardioembolic stroke from large vessel stroke, repeated measures analysis of variance (ANOVA) was used including stroke etiology, time, stroke etiology & time interaction, and the within subject variance in the model. Unsupervised hierarchical clustering and principal components analysis (PCA) were used to evaluate relationships between cardioembolic stroke and large vessel stroke. Gene probes with a p value ≤0.005 and a fold change ≥|1.2| were considered significant.

A similar analysis was used to identify the gene expression profiles that distinguish cardioembolic stroke due to atrial fibrillation from non-atrial fibrillation causes. A repeated measures ANOVA was used including cardioembolic stroke etiology, time, and within subject variance in the model. Unsupervised hierarchical clustering and PCA were used to evaluate relationships between cardioembolic stroke caused by atrial fibrillation and non-atrial fibrillation. Gene probes with a p value ≤0.005 and a fold change ≥|1.2| were considered significant.

Functional analysis was performed by comparing subjects with cardioembolic stroke and large vessel stroke to control subjects. A one-way ANCOVA was used adjusting for age and gender. Gene probes with a p value ≤0.005 and a fold change ≥|1.2| were considered significant and analyzed in IPA.

Results

Cardioembolic versus Large Vessel Ischemic Stroke

Demographic and clinical characteristics of subjects used for the comparison of cardioembolic stroke to large vessel stroke are shown in Table 8. Atrial fibrillation was the only variable significantly different between groups (p<0.05). There were 69 samples with cardioembolic stroke and 30 samples with large vessel stroke.

Initially the ability of the previously published 77 gene list to distinguish cardioembolic stroke from large vessel stroke was evaluated [Xu H et al., *J Cereb Blood Flow Metab.*, 28:1320-1328 (2008)]. This gene list was based on the first 11 patients enrolled in the CLEAR trial, 7 with cardioembolic stroke and 4 with large vessel stroke. Using a k-nearest neighbor prediction model, the preliminary 77 gene list was used to predict the completed CLEAR trial patient population. Cardioembolic stroke was correctly predicted in 82.6% of samples, and large vessel stroke was correctly predicted in 80.0% of samples. However, on 10-fold leave one out cross-validation, 56.5% were correctly predicted as cardioembolic stroke and 60% were correctly predicted as large vessel stroke, with the probability of predicted diagnosis being below 90% in most samples. These results suggests that gene expression profiles in blood can distinguish cause of stroke, though further refinement is required to better generalize genomic predictors to a larger patient population.

Figure 12:
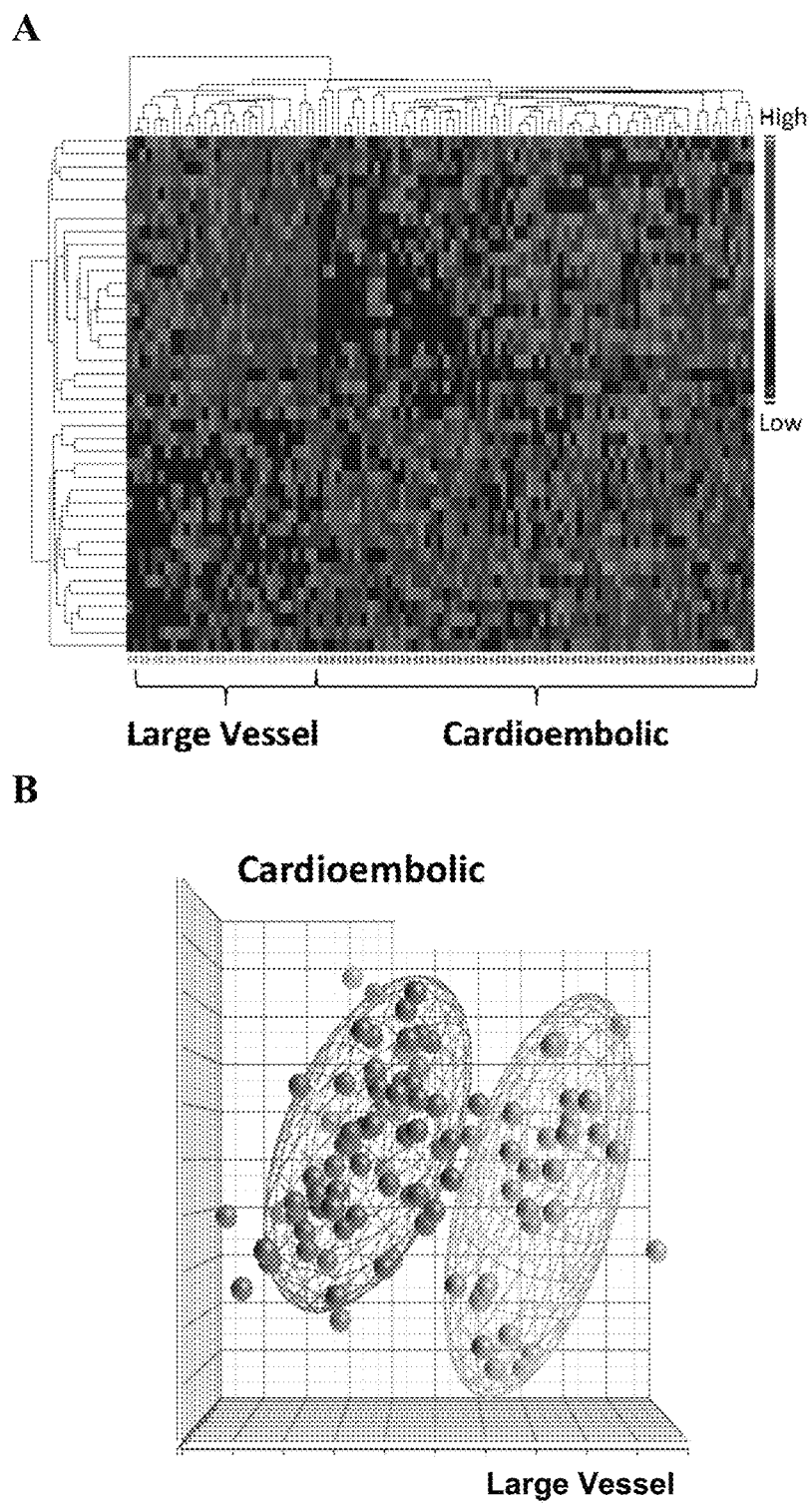
FIGS. 12A-B A. Hierarchical cluster plot of the 40 genes found to differentiate cardioembolic stroke from large vessel stroke. Genes are shown on the y-axis and subjects are shown on the x-axis. Red indicates a high level of gene expression and blue indicates a low level of gene expression. Subjects can be observed to cluster by diagnosis. A group of genes have a high level of expression in cardioembolic stroke and a low level of expression in large vessel stroke. A separate group of genes have a low level of expression in cardioembolic stroke and a high level of expression in large vessel stroke. The cardioembolic group appears to cluster into two subgroups. B. Principal Component Analysis (PCA) of the 40 genes found to differentiate cardioembolic stroke from large vessel stroke. Each sphere represents a single subject. The ellipsoid surrounding the spheres represents two standard deviations from the group mean.
Figure 17:
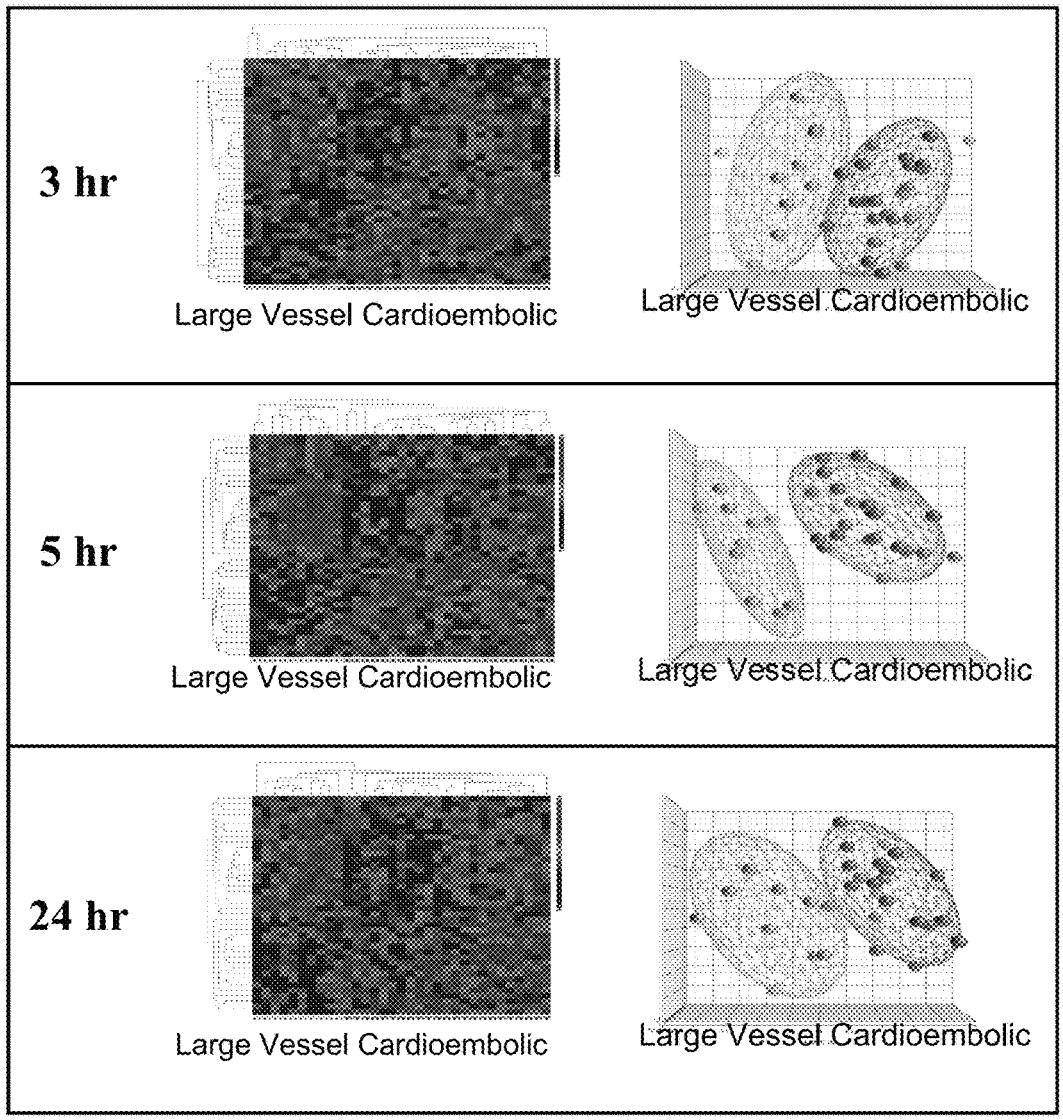
FIG. 17. Hierarchical cluster plots and PCAs of the 40 genes found to differentiate cardioembolic stroke from large vessel stroke at 3 hours, 5 hours and 24 hours following stroke onset. The hierarchical clusters show that separation by the 40 genes of cardioembolic stroke from large vessel stroke is achieved at 3 hours, 5 hours and 24 hours following onset of ischemic stroke. This is confirmed by the PCAs which show that subjects with cardioembolic stroke are separated by greater than two standard deviations from large vessel stroke.

Analysis of the complete CLEAR trial patients was thus performed. A repeated measures ANOVA identified 40 genes significantly different between cardioembolic stroke and large vessel stroke at all three time points (Table 13). A hierarchical cluster plot of the 40 genes is shown in FIG. 12*a*, and a Principal Component Analysis (PCA) in FIG. 12*b*. The 40 genes separate cardioembolic stroke from large vessel stroke by at least 2 standard deviations (FIG. 12*b*). The hierarchical cluster plot demonstrates a group of genes that are up-regulated in cardioembolic stroke and down-regulated in large vessel stroke. There is also a group of genes that are down-regulated in cardioembolic stroke and up-regulated in large vessel stroke. The 40 genes separate cardioembolic from large vessel stroke at ≤3 hours, 5 hours and 24 hours following ischemic stroke as shown in FIG. 17.

Prediction of Cardioembolic and Large Vessel Stroke

Figure 13:
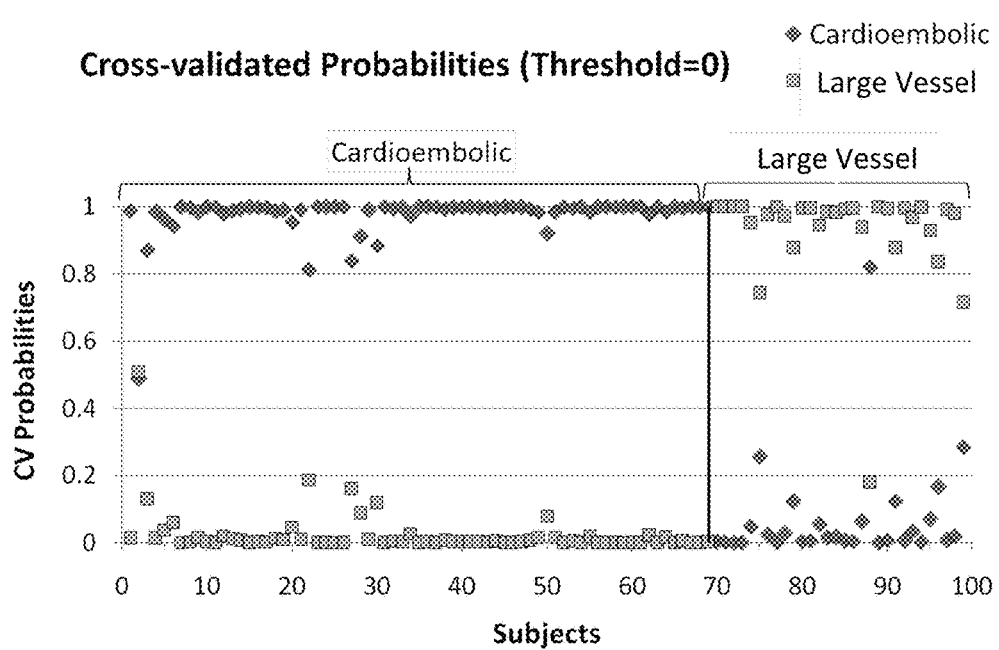
FIG. 13. Leave one out cross-validation prediction analysis of the 40 total genes found to differentiate cardioembolic stroke from large vessel stroke. The probability of the predicted diagnosis in shown on the y-axis. The actual diagnosis of is shown on the x-axis. Subjects with cardioembolic stroke were predicted to have cardioembolic stroke for 69 out of 69 samples (100% correct prediction). Subjects with large vessel stroke were predicted to have large vessel stroke for 29 out of 30 samples (96.7% correct prediction). A sample is considered misclassified if the predicted class does not match the known class with a probability greater than 0.5.

The ability of the 40 genes to predict cardioembolic stroke from large vessel stroke was evaluated using 10-fold leave one out cross-validation model in PAM. Of the 99 samples, 100% of the 69 samples with cardioembolic stroke were correctly predicted, and 96.7% of the 30 samples with large vessel stroke were correctly predicted (FIG. 13). The probability of predicted diagnosis was >90% for the majority of samples (FIG. 13). To further evaluate the 40 gene list, it was applied to a separate group of patients with known cardioembolic stroke. Of the 10 samples, 90% (9/10) were correctly predicted as cardioembolic stroke.

The 40 gene list was subsequently used to predict the cause of stroke in patients with cryptogenic stroke. There were 36 patients (85 samples) with cryptogenic stroke. To be considered classified by the prediction model, all samples from each patient were required to have a >90% probability of the same predicted diagnosis. A total of 15 patients (41%) were predicted to have a profile similar to cardioembolic stroke with a probability >90%, and a total of 6 patients (17%) were predicted to have a profile similar to large vessel stroke with a probability >90%. This represents a potential reclassification of 58% of cryptogenic stroke to either cardioembolic or large vessel stroke.

Functional Analysis

To determine the functional pathways associated with cardioembolic and large vessel stroke, the subjects with cardioembolic and large vessel stroke were compared to controls. There were 731 genes significantly different between cardioembolic stroke subjects and controls, and 782 genes that were significantly different between large vessel stroke and controls (p<0.005, fold change ≥|1.2|). These two gene lists are shown in a Venn diagram in FIG. 14. There were 503 genes unique to cardioembolic stroke, 554 genes unique to large vessel stroke and 228 genes common to cardioembolic stroke and large vessel stroke. The top Canonical and molecular functions of these respective gene lists are shown in Tables 9-11.

Of the 503 cardioembolic stroke genes, specific genes that have been previously associated with three of the main cardiac diseases include: atrial fibrillation genes—CREM, SLC8A1, KNCH7, KCNE1; myocardial infarction genes—PDE4B, TLR2; and heart failure genes—MAPK1, HTT, GNAQ, CD52, PDE4B, RAF1, CFLAR, and MDM2 (Table 9). Cardioembolic stroke was associated with development of lymphocytes, inflammatory disorder, cardiomyocyte cell death, and phosphatidylinositiol 4-phosphate modification. Top canonical pathways included renin-angiotensin signaling, thrombopoietin signaling, NF-κB activation, cardiac hypertrophy, and B cell receptor signaling (Table 9).

Of the 554 large vessel stroke genes, specific genes that have been previously associated with atherosclerotic lesion and atherosclerotic plaque include MMP9, FASLG, CX3R1, RAG1, TNF, IRAG1, CX3CR, and THBS1 (Table 10). Large vessel stroke was associated with T cell and leukocyte development, inflammation, and invasion. Top canonical pathways include T cell activation and regulation, CCR5 signaling in macrophages, relaxin signaling, and corticotropin releasing hormone signaling (Table 10).

Figure 14:
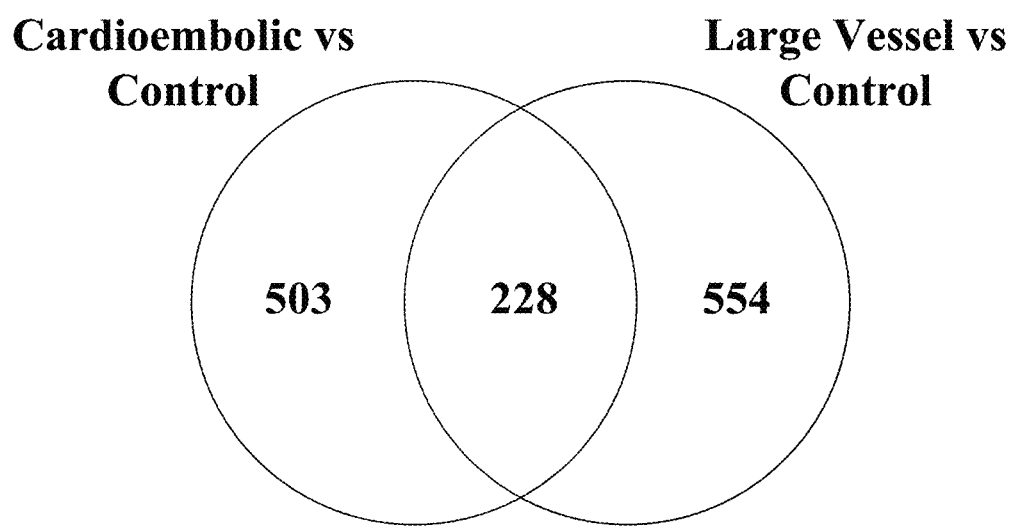
FIG. 14. Venn diagram of genes identified from the comparison of cardioembolic to controls, and large vessel stroke to control (p<0.005, FC>|1.2|). A total of 503 genes were found to be unique to cardioembolic stroke, 554 genes unique to large vessel stroke and 228 genes were common to stroke subtypes. These gene lists were used for functional analyses shown in Tables 9-11.

A total of 228 genes were common to cardioembolic stroke and large vessel stroke, representing ischemic stroke (FIG. 14). They were associated with leukocyte and phagocyte development and movement, cardiovascular processes, NF-κB response element expression, and oxidative stress (Table 11). Top canonical pathways include p38 MAPK signaling, toll-like receptor signaling, IL-6 and IL-10 signaling, NK-κB signaling, B-cell receptor signaling, and NRF-mediated oxidative stress (Table 11).

Atrial Fibrillation Versus Non-Atrial Fibrillation Cardioembolic Stroke

Figure 18:
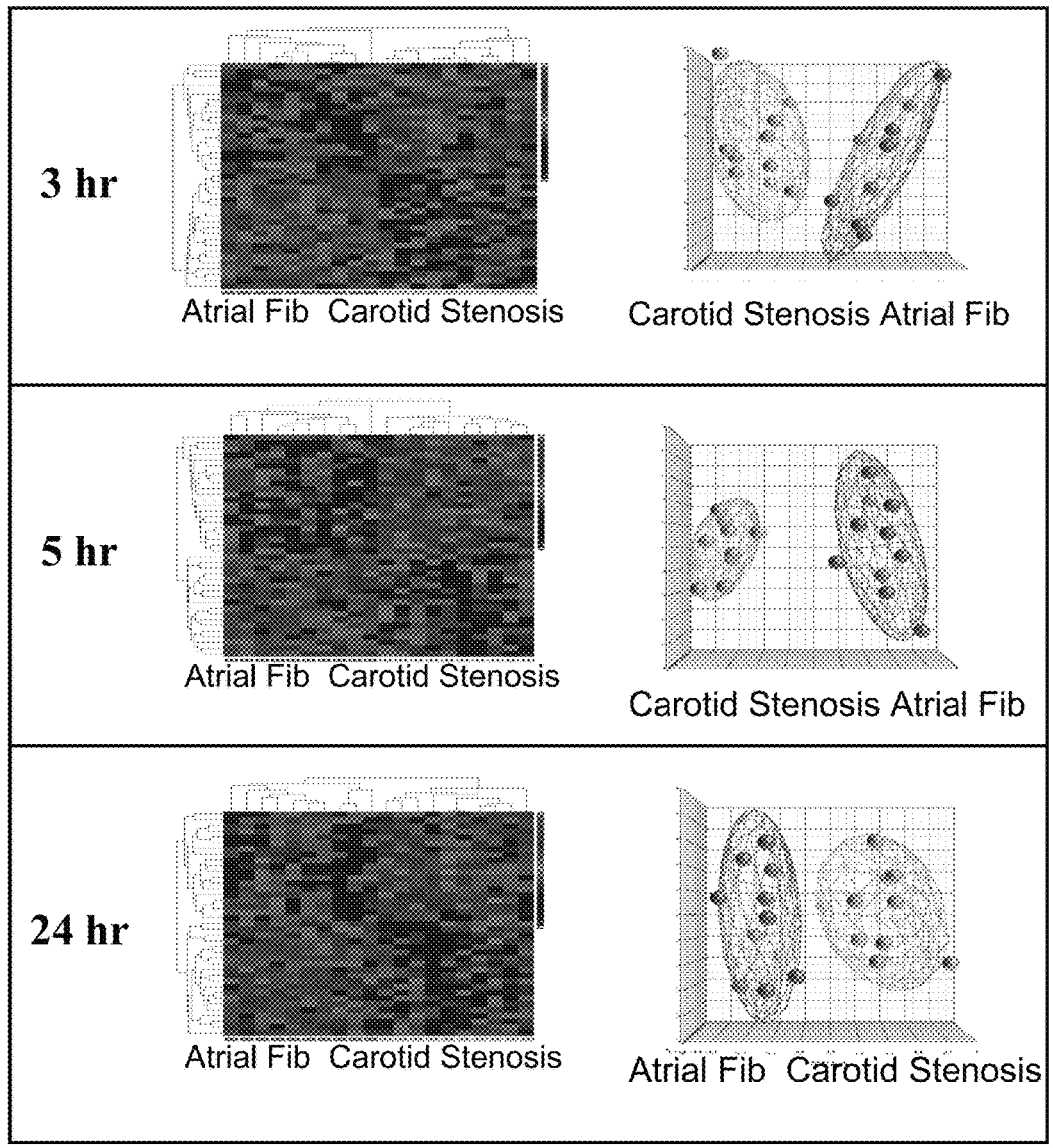
FIG. 18. Hierarchical cluster plots and PCAs of the 37 genes found differentiate cardioembolic stroke due to atrial fibrillation from non-atrial fibrillation causes at 3 hours, 5 hours and 24 hours following the stroke onset. The hierarchical clusters show the 37 genes can separate cardioembolic stroke due atrial fibrillation non-atrial fibrillation causes at 3 hours, 5 hours and 24 hours following onset of ischemic stroke. This is confirmed by the PCA analyses which show that subjects with cardioembolic stroke due to atrial fibrillation are separated by greater than two standard deviations from non-atrial fibrillation causes.

There were 23 subjects with cardioembolic stroke, 10 with atrial fibrillation and 13 with no atrial fibrillation identified on routine investigation. Subjects in the non-atrial fibrillation group who are more likely to have paroxysmal atrial fibrillation were excluded. To do this, the 10 patients with stroke due to atrial fibrillation were initially compared to the 10 patients with large vessel stroke. Repeated measures ANOVA identified a 39 gene profile of atrial fibrillation. This profile was then used to predict which of the 13 cardioembolic stroke subjects without atrial fibrillation identified on routine investigation had the highest probability of being similar to atrial fibrillation. There were 5 subjects who fell within 4 standard deviations of the mean predicted probability of patients with known atrial fibrillation. These patients were considered more likely to have paroxysmal atrial fibrillation and thus were excluded from further analysis, as a conservative method to reduce the possibility of paroxysmal atrial fibrillation being present in the non-atrial fibrillation group. The remaining 8 non-atrial fibrillation patients were compared to the 10 patients with atrial fibrillation. The demographic and clinical characteristics of are shown in Table 12. Atrial fibrillation was the only variable significantly different between the two groups (p<0.05). A repeated measures ANOVA identified 37 genes that were significantly different between atrial fibrillation and non-atrial fibrillation causes of cardioembolic stroke (Table 14). A hierarchical cluster plot of the 37 genes is shown in FIG. 15a, and a PCA in FIG. 15b. The 37 genes clearly separate atrial fibrillation from non-atrial fibrillation (FIG. 15). The 37 genes can separate atrial fibrillation from non-atrial fibrillation cardioembolic stroke at ≤3 hours, 5 hours and 24 hours following ischemic stroke (FIG. 18). The 37 genes were applied to the 5 subjects excluded from analysis, with 2 being predicted to be atrial fibrillation, 2 being indeterminate, and 1 being predicted to be non-atrial fibrillation cardioembolic stroke.

Figure 16:
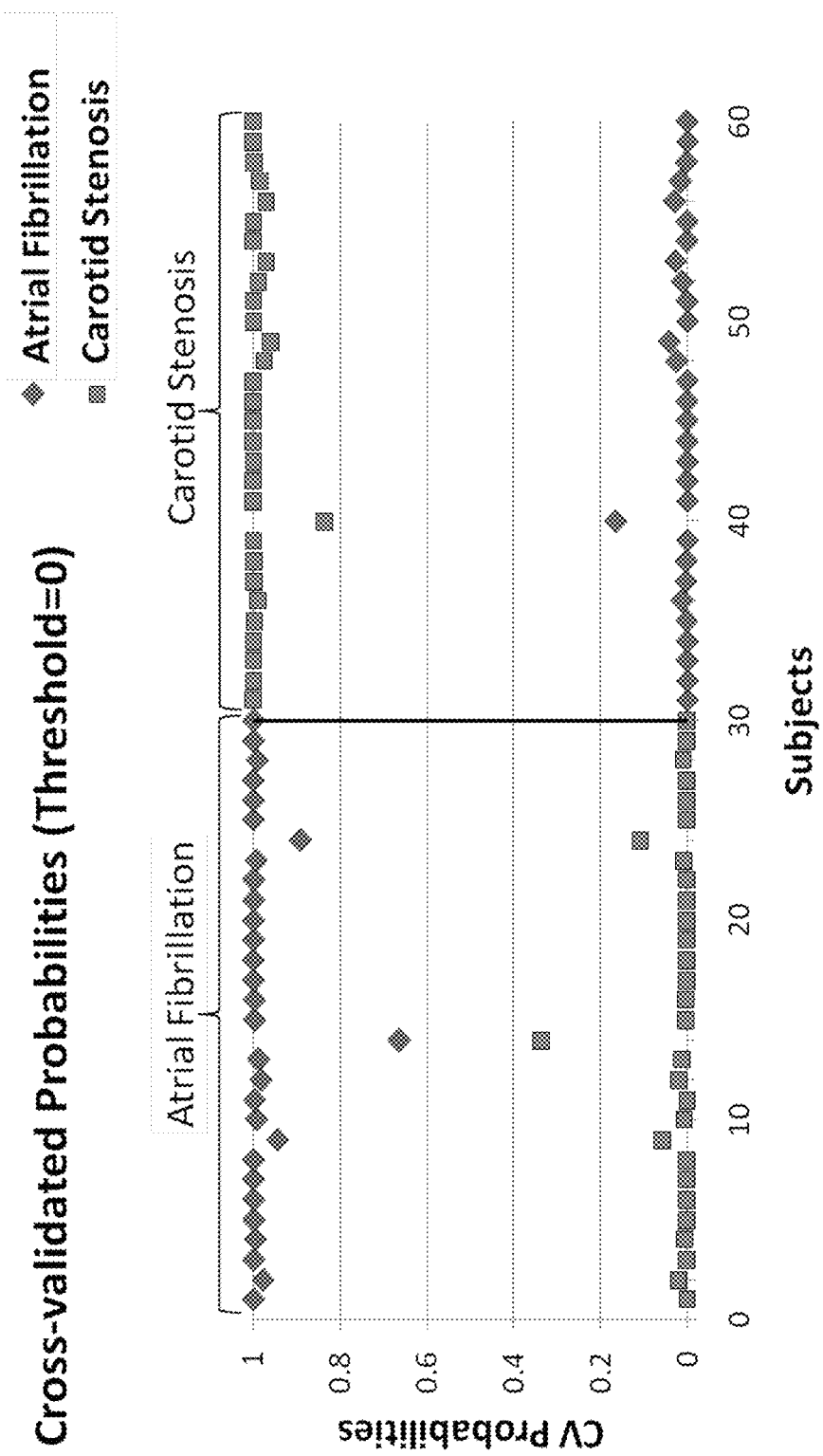
FIG. 16. Leave one out cross-validation prediction analysis of the 37 genes found to differentiate cardioembolic stroke due to atrial fibrillation from non-atrial fibrillation causes. The probability of the predicted diagnosis is shown on the y-axis. The actual diagnosis of is shown on the x-axis. Subjects with cardioembolic stroke due to atrial fibrillation were predicted to have atrial fibrillation as a cause of stroke in 30 out of 30 samples (100% correct prediction). Subjects with cardioembolic stroke due to non-atrial fibrillation causes were correctly predicted in 22 out of 24 samples (91.7% correct prediction). A sample is considered misclassified if the predicted class does not match the known class with a probability greater than 0.5.

Prediction of Atrial Fibrillation and Non Atrial Fibrillation Cardioembolic Stroke The ability of the 37 genes to predict atrial fibrillation from non-atrial fibrillation causes of cardioembolic stroke was evaluated using a 10-fold leave one out cross-validation model in PAM. In the 60 samples, 100% of the 30 samples with atrial fibrillation cardioembolic stroke were correctly predicted, and 91.7% of the 30 samples with non-atrial fibrillation cardioembolic stroke were correctly predicted (FIG. 16). Additionally, the probability of predicted diagnosis was >90% for most samples.

The 37 gene list was used to predict a test set of 10 samples with cardioembolic stroke who did not have atrial fibrillation identified on routine testing. Of these 10 samples, 3 (30%) were predicted to have paroxysmal atrial fibrillation with >90% probability when compared to the gene expression profile of subjects with known symptomatic atrial fibrillation. The 37 gene list was also used to predict the cause of stroke in patients with cryptogenic stroke. There were 11 patients with cryptogenic stroke who were predicted to have cardioembolic stroke based on the 40 gene profile. Of these 11 patients, 3 patients (27%) were predicted to have paroxysmal atrial fibrillation with a probability >90% based on a gene expression profile that was similar to subjects with known atrial fibrillation stroke.

Discussion

Determining the cause of ischemic stroke is of paramount importance as it guides management decisions such as whether to initiate antiplatelet or anticoagulation treatment. However, identifying the cause of stroke remains a challenge in many patients as exemplified by cryptogenic stroke. Given that cryptogenic stroke accounts for approximately 30% of ischemic strokes, better classification tools are required. The use of gene expression profiles in blood to distinguish cardioembolic stroke from large vessel stroke on a molecular level are described herein. A 40 gene expression profile can distinguish cardioembolic stroke from large vessel stroke, and a 37 gene expression profile can distinguish cardioembolic stroke due to atrial fibrillation from non-atrial fibrillation causes. When applied to cryptogenic stroke, 58% of subjects can be reclassified with a probability >90% as being either cardioembolic or large vessel stroke.

Limitations of large-scale gene expression profiling have been well described [Schulze A and Downward J., Nat Cell Biol., 3:E190-195 (2001)]. However, comparable approaches have applied in patients with human malignancies and that have translated to PCR based arrays for diagnostic purposes [Hedenfalk I et al., N Engl J Med., 344:539-548 (2001); Valk P J et al., N Engl J Med., 350: 1617-1628 (2004)]. Unlike human malignancy with distinct histological criteria, ischemic stroke subtypes are heterogeneous and rely on a combination of clinical and investigational criteria. With strict patient selection, molecular classification of ischemic stroke subtypes into clinically relevant subgroups with biomarkers appears to be feasible. Indeed, several prothrombotic and inflammatory biomarkers in the blood are different in each subtype of ischemic stroke [Laskowitz D T et al., Stroke, 40:77-85 (2009); Shibazaki K et al., Intern Med., 48:259-264 (2009); Montaner J et al., Stroke, 39:2280-2287 (2008); Hassan A et al., Brain, 126: 424-432 (2003); Xu H et al., J Cereb Blood Flow Metab., 28:1320-1328 (2008)].

Cardioembolic and Large Vessel Atherosclerotic Stroke

A gene expression profile able to differentiate cardioembolic stroke from large vessel stroke was identified. This distinction is clinically important as treatment and diagnostic testing are different between the two subtypes. In general, cardioembolic stroke benefit from anticoagulation, whereas large vessel stroke benefit from antiplatelet therapy and vascular surgery. Determining the etiology of stroke and thus the preventative treatments to be initiated relies on diagnostic tests. In fact, the TOAST criteria require that other causes of stroke be ruled out to make a probable diagnosis of cause [Adams H P, Jr., et al., Stroke, 24:35-41 (1993)]. As a result, patients with ischemic stroke frequently undergo extensive testing to image the vasculature and evaluate cardiac function. Diagnostic testing to determine the cause of stroke can be better focused by using gene expression profiles, particularly in cryptogenic stroke. In this manner, costly resources can be targeted to subjects where they will be of highest yield.

Cardioembolic Stroke

Currently, the selection of which patients with ischemic stroke require cardiac investigations such as Holter monitor and echocardiogram is based on clinical judgment combined with brain imaging. However, determining which ischemic stroke patients should be screened by transthoracic and transesophageal echocardiography is challenging. Though age <50 years is associated with higher diagnostic yield, many stroke patients are older than 50 years. Gene expression profiles in combination with clinical impression serve as a guide to direct echocardiography.

Cardiac monitoring for arrhythmias is also commonly performed following ischemic stroke. Identifying atrial fibrillation is important, as anticoagulation reduces recurrent embolic events. However, cardiac monitoring for 24 to 48 hours often misses paroxysmal atrial fibrillation [Tayal A H et al., *Neurology*, 71:1696-1701 (2008); Ziegler P D et al., *Stroke*, 41:256-260]. A gene expression profile suggesting a patient has a high probability of atrial fibrillation may be an additional tool to aid in preventing such missed treatment opportunities. In a group of 10 cardioembolic strokes who did not have atrial fibrillation identified on routine investigation, it is shown that a gene expression profile can predict 3 subjects (30%) to have paroxysmal atrial fibrillation with greater than 90% probability. This is consistent with previous studies of cardioembolic stroke without atrial fibrillation on routine investigation, where an additional 23-28% cases of paroxysmal atrial fibrillation can be identified using long term cardiac monitoring [Tayal A H et al., *Neurology*, 71:1696-1701 (2008), Ziegler P D et al., *Stroke*, 41:256-260]. Subjects who appear to have atrial fibrillation by gene expression profiles could be a target group for such prolonged cardiac recording.

Large Vessel Stroke

Gene expression profiles may also aid in the diagnosis of large vessel stroke. Evaluation of large vessel atherosclerotic disease includes imaging of extracranial and intracranial vessels using magnetic resonance angiography (MRA), computed tomography angiography (CTA), ultrasound and conventional angiography. Inconsistencies in the results of vascular imaging do occur. For example, the degree of carotid stenosis by ultrasound may not agree with the degree of stenosis by MRA or CTA. Supplementing imaging with a gene expression profile suggestive of symptomatic atherosclerotic disease could add confidence to the diagnosis of large vessel atherosclerotic disease. The presence of large vessel disease is large based on a single factor, the degree of vascular stenosis. In the TOAST criteria, a stenosis less than 50% is considered negative [Adams H P, Jr., et al., *Stroke*, 24:35-41 (1993)]. Gene expression profiles provide an additional measure of factors associated with symptomatic atherosclerotic disease, particularly inflammation. This is similar in concept to MRI methods to determine atheroma inflammation [Tang T Y et al., *Arterioscler Thromb Vasc Biol.*, 29:1001-1008 (2009)]. These proposed applications of gene expression profiles require further investigation. However, they show promise as methods to better target investigations and treatments to patients with ischemic stroke.

Cryptogenic Stroke

Cryptogenic stroke is a heterogeneous group of patients where better diagnostic tools are required. The gene expression profiles described herein were applied to the cryptogenic stroke group and predicted 41% to have cardioembolic stroke. Of these patients, 27% were suggested to have atrial fibrillation. Cryptogenic stroke patients with a molecular signature similar to cardioembolic stroke may represent a group where long term cardiac monitoring can be focused, and potentially a subgroup where a trial of anticoagulation could be performed [Tayal A H et al., *Neurology*, 71:1696-1701 (2008); Harloff A et al., *Stroke*, 37:859-864 (2006); Sacco R L et al., *Cerebrovasc Dis.*, 22:4-12 (2006); Mohr J P et al., *N Engl J Med.*, 345:1444-1451 (2001)]. 17% of the cryptogenic group were also predicted to have large vessel stroke. This finding may represent a symptomatic stenosis <50%, though further study with thorough vascular imaging is required.

Functional Analysis

The rationale for changes in gene expression in blood of patients with ischemic stroke rests largely in differences in patterns of inflammation. The major source of RNA in the blood is immune cells including leukocytes, neutrophils, and monocytes [Du X et al., *Genomics*, 87:693-703 (2006)]. Immune cells provide an indirect reflection of a patient's disease state and subsequent response, such as the immune response to ischemic brain tissue and immune response to disease mediated by vascular risk factors. The majority of these responses remain unclear, though it appears there are differences in the ways these responses are orchestrated between subjects with cardioembolic stroke and large vessel stroke. This is evidenced by the 40 gene profile for cardioembolic stroke and large vessel stroke, and the 37 gene profile for cardioembolic stroke due to atrial fibrillation and non-atrial fibrillation. The fact that different genes are associated with stroke of large vessel, cardioembolic, and atrial fibrillation origin suggests specific immune responses in each condition. The precise cause for these differences, including immune cell-endothelial interactions, remain unknown and should become clearer as each condition and cause is studied.

In conclusion, the present invention provides gene expression signatures can distinguish between cardioembolic and large vessel subtypes of ischemic stroke. Gene expression profiles find use for the development of blood tests to aid in the classification of ischemic stroke, target stroke investigation and treatment, and determine the causes of cryptogenic stroke.

Tables

TABLE 8

Demographic variables for subjects with cardioembolic stroke and large vessel stroke. p-values represent comparisons of subjects with cardioembolic to large vessel stroke using Fisher's exact test or two-tailed t-test where appropriate. (BP, blood pressure; CABG, coronary artery bypass graft)

| Variables | Cardioembolic (n = 23) | Large Vessel (n = 10) | p value |
|---|---|---|---|
| Mean Age (years) | 71.7 ± 1.6 | 66.9 ± 2.9 | 0.14 |
| Sex, male (%) | 12 (52.2%) | 8 (80%) | 0.25 |
| Race, Caucasian (%) | 15 (65.2%) | 8 (80%) | 0.68 |
| Hypertension (%) | 16 (69.6%) | 8 (80%) | 0.55 |
| Mean Systolic BP | 158.3 ± 6.1 | 163.5 ± 8.0 | 0.63 |
| Mean Diastolic BP | 80.6 ± 3.6 | 88 ± 6.7 | 0.30 |
| Diabetes (%) | 4 (17.4%) | 4 (40%) | 0.21 |
| Hyperlipidemia (%) | 6 (26.1%) | 3 (30%) | 1.00 |
| Mean Weight (kg) | 81.9 ± 4.5 | 89.6 ± 6.2 | 0.34 |
| Atrial Fibrillation (%) | 10 (43.4%) | 0 (0%) | 0.03 |
| Myocardial Infarction (%) | 4 (17.3%) | 2 (20%) | 1.00 |
| Congestive Heart Failure | 8 (34.8%) | 2 (20%) | 0.68 |
| Coronary Artery Bypass | 5 (21.7%) | 1 (10%) | 0.64 |
| Carotid Endarterectomy | 0 (0%) | 2 (20%) | 0.08 |
| Femoral Popliteal Bypass | 0 (0%) | 1 (10%) | 0.30 |
| Prior Stroke | 7 (30.4%) | 1 (10%) | 0.38 |
| Mean NIHSS 3 hours | 11.9 ± 1.7 | 12.7 ± 1.0 | 0.69 |
| Mean NIHSS 24 hours | 11.2 ± 1.8 | 13.9 ± 3.0 | 0.44 |
| Mean NIHSS 5 days | 10.3 ± 2.1 | 12.1 ± 4.7 | 0.69 |

TABLE 9

Functional analysis of 503 genes found to be unique to Cardioembolic strokes when compared to controls (p < 0.005, FC > |1.2|)

| | CE | Genes | p-value |
|---|---|---|---|
| Canonical Pathways | Renin-angiotensin signaling | ADCY4, GNAQ, PAPK1, MAPK14, PIK3C3, PIK3C2B, PRKARIA, PRKCZ, RAF1 | $2.6 \times 10^{-4}$ |
| | Thrombopoietin signaling | MAPK1, PIK3C3, PIK3C2B, PRKCZ, RAF1, STAT5B* CXCR5, ITGAL, MAPK1, PIK3C3, PIK3C2B, PRKCZ, RAF1 | $5.8 \times 10^{-4}$ |
| | NF-kB activation | MAPK1, MDM2, PIK3C3, PIK3C2B, PRKCZ, PTEN*, RAF1, TFDP1 | $6.0 \times 10^{-4}$ |
| | Cardiac Hypertrophy role of NFAT | ADCY4, GNAQ, MAPK1, MAPK14, MEF2A, PIK3C3, PIK3C2B, PRKARIA, PRKCZ, RAF1, SLC8A1 | $9.9 \times 10^{-4}$ |
| | B cell receptor Signaling | BCL6, FCGR2C, MAP3K2, MAPK1, MAPK14, PIK3C3, PIK3C2B, PTEN*, RAF1 | $2.4 \times 10^{-3}$ |
| Molecular Functions | Lymphocyte development | APC, BCL6, CARD11, CD55, CFLAR, CXCR5, DTX1, GATA3, HIST1H1C, HLA-DOA, IFNGR1, IL13RA1, IL27RA, ITGAL, KLF13, MAP3K2, MAPK1, MAPK14, MBP, MDM2, PRKCZ, PTEN, RAF1, RBPJ, SEMA4A, SMARCA4, SRGN, STAT5B, STK17B, TXN, XRCC5 | $1.4 \times 10^{-5}$ |
| | Cardiomyocytes cell death | CREM, GHRL, GNAQ, MAPK1, MAPK14, MDM2, NAMPT, PTEN, RAF1, SLC8A1, SOD2 | $1.8 \times 10^{-4}$ |
| | T lymphocyte development | APC, BCL6, CARD11, CD55, CFLAR, DTX1, GATA3, HIST1H1C, HLA-DOA, IFNGR1, IL27RA, KLF13, MAP3K2, MAPK1, MAPK14, MBP, MDM2, PRKCZ, PTEN, SEMA4A, SMARCA4, SRGN, STAT5B, STK17B, XRCC5 | $2.8 \times 10^{-4}$ |
| | Inflammatory disorder | ABCB4, AHNAK, AKAP13, ANXA3, AQP9, ARF1, ASPH, B4GALT1, BCL6, CARD11, CASC4, CD55, CDH26, CFLAR, CLEC4D, CMIP, CR1, CREM, CXCR5, DHX37, DIS3L2, DYNC1LI1, ENG, ENTPD1, ETV5, EXOC6, FBXL13, FGGY, GATA3, GEMIN5, GLG1, H3F3B, HCG27, HDGFRP3, HLA-DOA, HTT, IFNGR1, IL18RAP, IL27RA, ITGAL, KALRN, KIF13A, KLF13, LHX2, LYST, MAP4, MAPK14, MBP, MDM2, MED24, MEF2A, MTHFS, NAMPT, NAT10, NBAS, NCOA2, NUMB, NUP62, OSBPL1A, PDE4B, PHF15, PHRF1, PRKCZ, PTEN, RAF1, S100A9, S100A12, SBF2, SLC22A4, SLC7A11, SLC8A1, SOD2, SOX6, STAT5B, STK17B, TPST1, TRRAP, TSPAN2, TTYH2, TXN, USP11, USP15, VIM, VSIG4, YEATS2, ZFHX3, ZNF230, ZNF831 | $4.1 \times 10^{-4}$ |
| | Phosphatidylinositol 4-phosphate modification | PI4KA, PIK3C3, PIK3C2B, PTEN | $4.4 \times 10^{-4}$ |

TABLE 10

Functional analysis of the 554 genes unique to large vessel atherosclerotic stroke when compared to controls (p < 0.005, FC > |1.2|).

| | LV | Genes | p-value |
|---|---|---|---|
| Canonical Pathways | Cytotoxic T lymphocyte target cell apoptosis | APAF1, CD247, FADD, FASLG, TRA@, TRD@ | $1.3 \times 10^{-5}$ |
| | CCR5 signaling in macrophages | CD247, FASLG, GNAI1, GNG*, MAPK13*, PRKCZ, TRA@, TRD@ | $1.3 \times 10^{-4}$ |
| | Relaxin signaling | GNAI1, GNG2, GUCY2D, MAPK1, MMP9, NF-κB IE, NPR2, PDE2A, PIK3R3, PRKACA, PRKCZ | $1.5 \times 10^{-4}$ |
| | Corticotropin releasing hormone signaling | FASLG, GNAI1, GUCY2D, MAPK1, MAPK13, NPR2, NR4A1 | $1.0 \times 10^{-3}$ |
| | T lymphocyte regulation | CD247, NR4A1, PRKCZ, TRA@, TRD@, ZAP70* | $1.3 \times 10^{-3}$ |

TABLE 10-continued

Functional analysis of the 554 genes unique to large vessel atherosclerotic stroke when compared to controls (p < 0.005, FC > |1.2|).

|  | LV | Genes | p-value |
|---|---|---|---|
| Molecular Functions | T lymphocyte differentiation | ADA, TRA@, ZAP70 | $1.4 \times 10^{-3}$ |
|  | Leukocyte development, morphology | ADA, APAF1, CCR8, CD83, CD247, CSF1, CSF2RA, CXCL12, EZH2, F5, FADD, FASLG, HIVEP2, IL12RB1, IL21R, ITGB7, MAPK1, NR4A1, PDIA3, PRKCZ, RAG1, RNASEL, SMAD7, THBS1, TRA@, XIAP, ZAP70 | $1.5 \times 10^{-3}$ |
|  | Invasion of cells | MMP9, PLAUR | $1.7 \times 10^{-3}$ |
|  | Inflammatory disorder | ADA, ADORA3, ADRB2, ALOX5AP, APAF1, ARHGDIB, ARHGEF17, ASPH, ATP4B, C20ORF43, CA4, CA13, CAPN10, CD83, CD247, CDK6, CLCN6, COL9A3, COLQ, CORIN, CORO2A, CSF1, CSF2RA, CX3CR1, CXCL12, EGFL8, F5, FAM101B, FASLG, FBF1, GNG2, GRB10, HIC1, HIVEP1, HP, KIAA1908, LIMD1, LTB4R, MAPK13, MDC1, MMP9, MPHOSPH9, MSRA, MYH3, NFIA, NR4A1, NUMA1, OLAH, PACSIN2, PADI4, PCNX, PDE2A, PDIA3, PER1, PFTK1, PGLYRP1, PGM1, PHF19, PIK3R3, PITPNA, PLAUR, PMF1, PPARGC1B, PRKCZ, PRR5L, PTGDR, PXK, RAB7A, RAG1, RAPH1, RARG, ROPN1L, SAMSN1, SERPINE2, SEZ6L, SLC25A15, SLC26A8, SLC8A1, SLCO4C1, SPRED1, SPTLC2, SRPK2, STK36, TAF7L, TBC1D1, TGFBR3, THBS1, TKT, TNFSF8, TNIK, TRA@, TTC7A, TUBA4, TUBA4A, VARS2, ZEB1 | $2.8 \times 10^{-3}$ |
|  | T cell development | ADA, APAF1, CCR8, CD83, CD247, CXCL12, F5, FADD, FASLG, HIVEP2, IL12RB1, IL21R, ITGB7, MAPK1, NR4A1, PDIA3, PRKCZ, RAG1, RNASEL, SMAD7, THBS1, TRA@, XIAP, ZAP70 | $5.2 \times 10^{-3}$ |

TABLE 11

Functional analysis of 228 genes common to cardioembolic and large vessel atherosclerotic stroke when compared to controls (p < 0.005, FC > |1.2|).

|  | LV-CE Common | Genes | p-value |
|---|---|---|---|
| Canonical Pathways | p38 MAPK Signaling | DUSP1*, IL1R2, IRAK3*, MAP2K6, MAPK14, MAX, MKNK1, TNF | $3.6 \times 10^{-6}$ |
|  | Toll-like receptor signaling | IRAK3*, MAP2K6, MAPK14, TLR2, TOLLIP | $1.2 \times 10^{-4}$ |
|  | IL-6 signaling | ABCB1, IL1R2*, MAP2K6, MAPK14, SOS2, TNF | $2.4 \times 10^{-4}$ |
|  | NF-κB Signaling | GSK3B, IL1R2, IRAK3, MAP2K6, MAP3K3, TLR2, TNF | $4.5 \times 10^{-4}$ |
|  | B Cell Receptor Signaling | GSK3B, MAP2K6, MAP3K3, MAPK14, NFATC2, PTEN, SOS2 | $5.6 \times 10^{-3}$ |
|  | Role of Macrophages, fibroblasts and endothelial cells in RA | CEBPD*, GSK3B, IL1R2*, IRAK3*, MAP2K6, MAPK14, NFATC2, TLR2, TNF | $2.8 \times 10^{-3}$ |
|  | IL-10 Signaling | IL1R2, MAP2K6, MAPK14, TNF | $3.1 \times 10^{-3}$ |
|  | NRF2-mediated Oxidative Stress | DNAJC3, FKBP5, GSK3B, MAP2K6, MAPK14, TXN | $6.6 \times 10^{-3}$ |
| Molecular Functions | Neutrophil/Phagocyte/Leukocyte movement | CAMP, CD55, CSF2RA, DUSP1, FCAR*, LILRA6, MAPK14, PTEN, SLPI, TLR2, TNF | $1.7 \times 10^{-5}$ |
|  | Leukocyte development, activation | BST1, CAMP, CD55, CD59, CEBPD, CFLAR, CSF2RA, F5, GATA3, GSK3B, IL2RB, LILRA6, MAPK14, MLL, NFATC2, PRKDC, PTEN, RGL4, TLR2, TNF, TXN | $5.4 \times 10^{-5}$ |
|  | Cardiovascular process | BMX, GSK3B, IL18BP, MAP3K3, MAPK14, TLR2 | $1.2 \times 10^{-4}$ |

TABLE 11-continued

Functional analysis of 228 genes common to cardioembolic and large vessel atherosclerotic stroke when compared to controls (p < 0.005, FC > |1.2|).

| LV-CE Common | Genes | p-value |
|---|---|---|
| NF-kappa B response element expression | GSK3B, MAPK14, TLR2, TNF | $2.5 \times 10^{-4}$ |
| Leukocyte proliferation | CAMP, CD59, CFLAR, CSF2RA, GATA3, IL2RB, IRS2, MAPK14, MLL, NFATC2, PCYT1A, PTEN, SLPI, TLR2, TNF, TXN | $2.9 \times 10^{-4}$ |
| Oxidative stress | TNF, TXN | $3.0 \times 10^{-4}$ |

TABLE 12

Demographic variables for subjects with cardioembolic stroke due to atrial fibrillation and non-atrial fibrillation causes. p-values represent comparisons of subjects with atrial fibrillation to those with non-atrial fibrillation using Fisher's exact test or two-tailed t-test where appropriate. (BP, blood pressure; CABG, coronary artery bypass graft)

| Variables | Atrial Fibrillation (n = 10) | Non-Atrial Fibrillation (n = 8) | p value |
|---|---|---|---|
| Mean Age (years) | 72.9 ± 2.3 | 68.5 ± 3.1 | 0.26 |
| Sex, male (%) | 4 (40%) | 6 (75%) | 0.19 |
| Race, Caucasian (%) | 6 (60%) | 5 (62%) | 0.65 |
| Hypertension (%) | 8 (80%) | 6 (75%) | 1.00 |
| Mean Systolic BP | 158.3 ± 9.3 | 160.4 ± 10.7 | 0.88 |
| Mean Diastolic BP | 80.8 ± 4.7 | 86.1 ± 8.0 | 0.56 |
| Diabetes (%) | 1 (10%) | 2 (25%) | 0.56 |
| Hyperlipidemia (%) | 3 (30%) | 3 (30%) | 1.00 |
| Mean Weight (kg) | 86.9 ± 8.2 | 84.9 ± 5.7 | 0.85 |
| Myocardial Infarction (%) | 1 (10%) | 3 (37%) | 0.28 |
| Congestive Heart Failure | 5 (50%) | 3 (37%) | 0.28 |
| Coronary Artery Bypass | 1 (10%) | 1 (10%) | 1.00 |
| Carotid Endarterectomy | 0 (0%) | 0 (0%) | — |
| Femoral Popliteal Bypass | 0 (0%) | 0 (0%) | — |
| Prior Stroke | 3 (30%) | 3 (37%) | 1.00 |
| Mean NIHSS 3 hours | 17.3 ± 3.1 | 13.6 ± 2.4 | 0.39 |
| Mean NIHSS 24 hours | 11.6 ± 3.5 | 10.6 ± 3.0 | 0.83 |
| Mean NIHSS 5 days | 9.9 ± 3.5 | 10.0 ± 4.0 | 0.98 |

TABLE 13A

A list of 40 genes that differentiate cardioembolic stroke from large vessel stroke (p < 0.005, fold change > |1.2|).
Table 13A. Biomarkers that differentiate cardioembolic stroke from large vessel stroke

| Probe Set ID | Fold-Change (Large Vessel vs. Cardioembolic) | Gene Symbol | Gene Title | Gen Bank ID | Entrez Gene ID | UniGene ID | RefSeq Transcript ID | RefSeq Protein ID |
|---|---|---|---|---|---|---|---|---|
| 1552477_a_at | 1.26832 | IRF6 | interferon regulatory factor 6 | BC014852.1 | 3664 | Hs.719361 | NM_006147 | NP_006138 |
| 1556896_at | -2.02233 | LOC284751 | hypothetical LOC284751 | AK090605.1 | 284751 | Hs.282325 | NM_001025463 | NP_001020634 |
| 1557542_at | -1.33949 | — | — | AW069144 | — | Hs.353829 | — | — |
| 1559449_a_at | 1.34719 | ZNF254 | Zinc finger protein 254 | BF679633 | 9534 | Hs.434406 | NM_203282 | NP_975011 |
| 1565389_s_at | 1.45568 | GRM5 | glutamate receptor, metabotropic 5 | S64316.1 | 2915 | Hs.147361 | NM_000842 /// NM_001143831 | NP_000833 /// NP_001137303 |
| 202012_s_at | 1.19814 | EXT2 | exostoses (multiple) 2 | AA196245 | 2132 | Hs.368404 | NM_000401 /// NM_207122 | NP_000392 /// NP_997005 |
| 202399_s_at | 1.20871 | AP3S2 | adaptor-related protein complex 3, sigma 2 subunit | NM_005829.1 | 10239 | Hs.632161 | NM_005829 /// NR_023361 | NP_005820 |
| 204484_at | 1.32829 | PIK3C2B | phosphoinositide-3-kinase, class 2, beta polypeptide | NM_002646.1 | 5287 | Hs.497487 | NM_002646 | NP_002637 |
| 204765_at | 1.22689 | ARHGEF5 | Rho guanine nucleotide exchange factor (GEF) 5 | NM_005435.1 | 7984 | Hs.334 | NM_005435 | NP_005426 |
| 207549_x_at | -1.23817 | CD46 | CD46 molecule, complement regulatory protein | NM_002389.1 | 4179 | Hs.510402 | NM_002389 /// NM_153826 /// NM_172350 /// NM_172351 /// NM_172352 /// NM_172353 /// | NP_002380 /// NP_722548 /// NP_758860 /// NP_758861 /// NP_758862 /// NP_758863 /// |

TABLE 13A-continued

A list of 40 genes that differentiate cardioembolic stroke from large vessel stroke (p < 0.005, fold change > |1.2|).
Table 13A. Biomarkers that differentiate cardioembolic stroke from large vessel stroke

| Probe Set ID | Fold-Change (Large Vessel vs. Cardio-embolic) | Gene Symbol | Gene Title | Gen Bank ID | Entrez Gene ID | UniGene ID | RefSeq Transcript ID | RefSeq Protein ID |
|---|---|---|---|---|---|---|---|---|
| | | | | | | | NM_172354 /// NM_172355 /// NM_172356 /// NM_172357 /// NM_172358 /// NM_172359 /// NM_172360 /// NM_172361 | NP_758864 /// NP_758865 /// NP_758866 /// NP_758867 /// NP_758868 /// NP_758869 /// NP_758870 /// NP_758871 |
| 210839_s_at | −1.35639 | ENPP2 | ectonucleotide pyrophosphatase/ phosphodiesterase 2 | D45421.1 | 5168 | Hs.190977 | NM_001040092 /// NM_001130863 /// NM_006209 | NP_001035181 /// NP_001124335 /// NP_006200 |
| 211343_s_at | 1.84752 | COL13A1 | collagen, type XIII, alpha 1 | M33653.1 | 1305 | Hs.695934 | NM_001130103 /// NM_005203 /// NM_080798 /// NM_080799 /// NM_080800 /// NM_080801 /// NM_080802 /// NM_080803 /// NM_080804 /// NM_080805 /// NM_080806 /// NM_080807 /// NM_080808 /// NM_080809 /// NM_080810 /// NM_080811 /// NM_080812 /// NM_080813 /// NM_080814 /// NM_080815 | NP_001123575 /// NP_005194 /// NP_542988 /// NP_542989 /// NP_542990 /// NP_542991 /// NP_542992 /// NP_542993 /// NP_542994 /// NP_542995 /// NP_542996 /// NP_542997 /// NP_542998 /// NP_542999 /// NP_543000 /// NP_543001 /// NP_543002 /// NP_543003 /// NP_543004 /// NP_543005 |
| 215172_at | 1.46054 | PTPN20A /// PTPN20B | protein tyrosine phosphatase, non-receptor type 20A /// protein tyrosine phosphatase, non-receptor type 20B | AL050040.1 | 26095 /// 653129 | Hs.440733 | NM_001042357 /// NM_001042358 /// NM_001042359 /// NM_001042360 /// NM_001042361 /// NM_001042362 /// NM_001042363 /// NM_001042364 /// NM_001042365 /// NM_001042387 /// NM_001042389 /// NM_001042390 /// NM_001042391 /// NM_001042392 /// NM_001042393 /// NM_001042394 /// NM_001042395 /// NM_001042396 /// NM_001042397 /// NM_015605 | NP_001035816 /// NP_001035817 /// NP_001035818 /// NP_001035819 /// NP_001035820 /// NP_001035821 /// NP_001035822 /// NP_001035823 /// NP_001035824 /// NP_001035846 /// NP_001035848 /// NP_001035849 /// NP_001035850 /// NP_001035851 /// NP_001035852 /// NP_001035853 /// NP_001035854 /// NP_001035855 /// NP_001035856 /// NP_056420 |
| 218656_s_at | 1.51991 | LHFP | lipoma HMGIC fusion partner | NM_005780.1 | 10186 | Hs.507798 | NM_005780 | NP_005771 |
| 220178_at | −1.22676 | C19orf28 | chromosome 19 open reading frame 28 | NM_021731.1 | 126321 | Hs.656901 | NM_001042680 /// NM_021731 /// NM_074983 | NP_001036145 /// NP_068377 /// NP_778148 |
| 220545_s_at | −1.41349 | TSKS | testis-specific serine kinase substrate | NM_021733.1 | 60385 | Hs.515858 | NM_021733 | NP_068379 |
| 222915_s_at | 1.52098 | BANK1 | B-cell scaffold protein with ankyrin repeats 1 | AA811540 | 55024 | Hs.480400 | NM_001083907 /// NM_001127507 /// NM_017935 | NP_001077376 /// NP_001120979 /// NP_060405 |
| 223210_at | −1.30772 | CHURC1 | churchill domain containing 1 | AF060510.1 | 91612 | Hs.325531 | NM_145165 | NP_660148 |
| 226071_at | −1.30444 | ADAMTSL4 | ADAMTS-like 4 | AF217974.1 | 54507 | Hs.516243 | NM_019032 /// NM_025008 | NP_061905 /// NP_079284 |
| 226878_at | 1.47827 | HLA-DOA | major histocompatibility complex, class II, DO alpha | AL581873 | 3111 | Hs.631991 | NM_002119 | NP_002110 |

TABLE 13A-continued

A list of 40 genes that differentiate cardioembolic stroke from large vessel stroke (p < 0.005, fold change > |1.2|).
Table 13A. Biomarkers that differentiate cardioembolic stroke from large vessel stroke

| Probe Set ID | Fold-Change (Large Vessel vs. Cardio-embolic) | Gene Symbol | Gene Title | Gen Bank ID | Entrez Gene ID | UniGene ID | RefSeq Transcript ID | RefSeq Protein ID |
|---|---|---|---|---|---|---|---|---|
| 229487_at | 1.81657 | EBF1 | early B-cell factor 1 | W73890 | 1879 | Hs.573143 | NM_024007 | NP_076870 |
| 229559_at | −1.29088 | FLJ40125 | protein phosphatase 1B-like | BE732320 | 147699 | Hs.532872 | NM_001080401 | NP_001073870 |
| 230022_at | −1.5369 | CLEC18A | C-type lectin domain family 18, member A | BF057185 | 348174 | Hs.592064 | NM_001136214 /// NM_182619 | NP_001129686 /// NP_872425 |
| 230676_s_at | 1.23715 | TMEM19 | transmembrane protein 19 | AW663887 | 55266 | Hs.688627 | NM_018279 | NP_060749 |
| 231411_at | 1.51995 | LHFP | Lipoma HMGIC fusion partner | BE674089 | 10186 | Hs.507798 | NM_005780 | NP_005771 |
| 233016_at | −1.2455 | — | — | AK022893.1 | — | Hs.288478 | — | — |
| 233621_s_at | −1.72591 | ARHGEF12 | Rho guanine nucleotide exchange factor (GEF) 12 | AL137456.1 | 23365 | Hs.24598 | NM_015313 | NP_056128 |
| 233742_at | −1.30295 | C16orf68 | Chromosome 16 open reading frame 68 | AK000114.1 | 79091 | Hs.306380 | NM_024109 | NP_077014 |
| 235982_at | 1.53186 | FCRL1 | Fc receptor-like 1 | AA677057 | 115350 | Hs.656112 | NM_001159397 /// NM_001159398 /// NM_052938 | NP_001152869 /// NP_001152870 /// NP_443170 |
| 236592_at | −1.27563 | — | — | AI791859 | — | Hs.658362 | — | — |
| 238218_at | 1.3701 | OOEP | oocyte expressed protein homolog (dog) | AW206656 | 441161 | Hs.671212 | NM_001080507 | NP_001073976 |
| 239591_at | 3.94309 | LRRC37A3 | leucine rich repeat containing 37, member A3 | BF433269 | 374819 | Hs.551962 | NM_199340 | NP_955372 |
| 239724_at | −1.32678 | — | — | AI653368 | — | Hs.658979 | — | — |
| 242939_at | −1.37839 | TFDP1 | transcription factor Dp-1 | AI950069 | 7027 | Hs.79353 | NM_007111 /// NR_026580 | NP_009042 |
| 243185_at | 1.89601 | — | — | AA804267 | — | Hs.438315 | — | — |
| 243325_at | −1.21991 | GSTK1 | Glutathione S-transferase kappa 1 | AV722006 | 373156 | Hs.390667 | NM_001143679 /// NM_001143680 /// NM_001143681 /// NM_015917 | NP_001137151 /// NP_001137152 /// NP_001137153 /// NP_057001 |
| 243467_at | 1.37052 | — | — | AW406163 | — | Hs.435736 | — | — |
| 244181_at | −1.81372 | — | — | AA018968 | — | — | — | — |

TABLE 13B

Additional genes that differentiate cardioembolic stroke from large vessel stroke (p < 0.005, fold change > |1.2|).
Table 13B. Biomarkers that differentiate cardioembolic stroke from large vessel stroke

| Probe Set ID | Fold-Change (Large Vessel vs. Cardio-embolic) | Gene Symbol | Gene Title | GenBank ID | Entrez Gene ID | UniGene ID | RefSeq Transcript ID | RefSeq Protein ID |
|---|---|---|---|---|---|---|---|---|
| 203585_at | 1.31961 | ZNF185 | zinc finger protein 185 (LIM domain) | NM_007150.1 | 7739 | Hs.16622 | NM_007150 | NP_009081 |
| 210448_s_at | 1.51809 | P2RX5 | purinergic receptor P2X, ligand-gated ion channel, 5 | U49396.1 | 5026 | Hs.408615 | NM_002561 /// NM_175080 /// NM_175081 | NP_002552 /// NP_778255 /// NP_778256 |
| 221211_s_at | | C21orf7 | chromosome 21 open reading frame 7 | | 56911 | | | |
| 226085_at | | CBX5 | chromobox homolog 5 (HP1 alpha homolog, *Drosophila*) | | 23468 | | | |
| 207979_s_at | | CD8B | CD8b molecule | | 926 | | | |
| 201280_s_at | | DAB2 | disabled homolog 2, mitogen-responsive phosphoprotein (*Drosophila*) | | 1601 | | | |
| 219863_at | | HERC5 | hect domain and RLD 5 | | 51191 | | | |
| 205821_at | | KLRK1 | killer cell lectin-like receptor subfamily K, member 1 | | 22914 | | | |
| 1558882_at | | LOC401233 | similar to HIV TAT specific factor 1; cofactor required for Tat activation of HI | | 401233 | | | |
| 236930_at | | NUMB | (clone S171) | | 8650 | | | |
| 215175_at | | PCNX | pecanex homolog (*Drosophila*) | | 22990 | | | |
| 214146_s_at | | PPBP | pro-platelet basic protein (chemokine (C-X-C motif) ligand 7) | | 5473 | | | |
| 204507_s_at | | PPP3R1 /// WDR92 | protein phosphatase 3 (formerly 2B), regulatory subunit B, alpha isoform /// WD | | 5534 | | | |
| 232078_at | | PVRL2 | poliovirus receptor-related 2 (herpesvirus entry mediator B) | | 5819 | | | |
| 232079_s_at | | PVRL2 | poliovirus receptor-related 2 (herpesvirus entry mediator B) | | 5819 | | | |
| 225418_at | | PVRL2 | poliovirus receptor-related 2 (herpesvirus entry mediator B) | | 5819 | | | |
| 228996_at | | RC3H1 | ring finger and CCCH-type zinc finger domains 1 | | 149041 | | | |
| 202131_s_at | | RIOK3 | RIO kinase 3 (yeast) | | 8780 | | | |
| 212589_at | | RRAS2 | related RAS viral (r-ras) oncogene homolog 2 | | 22800 | | | |
| 206108_s_at | | SFRS6 | splicing factor, arginine/serine-rich 6 | | 6431 | | | |
| 239084_at | | SNAP29 | synaptosomal-associated protein, 29 kDa | | 9342 | | | |
| 217104_at | | ST20 | suppressor of tumorigenicity 20 | | 400410 | | | |
| 206366_x_at | | XCL1 | chemokine (C motif) ligand 1 | | 6375 | | | |
| 214567_s_at | | XCL1 /// XCL2 | chemokine (C motif) ligand 1 /// chemokine (C motif) ligand 2 | | 6375 /// 6846 | | | |

TABLE 14

Genes that differentiate carotid stenosis from atrial fibrillation (p < 0.005, fold change > |1.2|).
Table 14. Biomarkers that differentiate carotid stenosis from atrial fibrillation

| Probe Set ID | Fold-Change (Carotid vs. Afib) | Gene Symbol | Gene Title | GenBank ID | Entrez Gene ID | UniGene ID | RefSeq Transcript ID | RefSeq Protein ID |
|---|---|---|---|---|---|---|---|---|
| 1553994_at | 1.42712 | NT5E | 5'-nucleotidase, ecto (CD73) | BC015940.1 | 4907 | Hs.153952 | NM_002526 | NP_002517 |
| 1555469_a_at | 1.20537 | CLASP2 | cytoplasmic linker associated protein 2 | BC029035.1 | 23122 | Hs.108614 | NM_015097 | NP_055912 |
| 1556578_a_at | −1.20603 | FLJ31945 | hypothetical protein LOC440137 | AJ911996 | 440137 | Hs.183953 | XM_001714983 /// XM_001718431 | XP_001715035 /// XP_001716863 /// XP_001718483 |
| 1556896_at | −2.01983 | LOC284751 | hypothetical LOC284751 | AK090605.1 | 284751 | Hs.282325 | NM_001025463 | NP_001020634 |
| 1556999_at | −1.29018 | LOC100271832 | hypothetical LOC100271832 | BC035107.1 | 100271832 | — | NR_027097 | — |
| 1557542_at | −1.36504 | — | — | AW069144 | — | Hs.353829 | — | — |
| 1563614_at | −1.34743 | MTBP | Mdm2, transformed 3T3 cell double minute 2, p53 binding protein (mouse) binding protein, 104 kDa | AL832671.1 | 27085 | Hs.657656 | NM_022045 | NP_071328 |
| 1565389_s_at | 1.64476 | GRM5 | glutamate receptor, metabotropic 5 | S64316.1 | 2915 | Hs.147361 | NM_000842 /// NM_001143831 | NP_000833 /// NP_001137303 |
| 1565862_a_at | −1.28258 | — | — | H65800 | — | Hs.658642 | — | — |
| 203650_at | 1.4381 | PROCR | protein C receptor, endothelial (EPCR) | NM_006404.1 | 10544 | Hs.647450 | NM_006404 | NP_006395 |
| 203939_at | 1.73974 | NT5E | 5'-nucleotidase, ecto (CD73) | NM_002526.1 | 4907 | Hs.153952 | NM_002526 | NP_002517 |
| 204765_at | 1.27552 | ARHGEF5 | Rho guanine nucleotide exchange factor (GEF) 5 | NM_005435.1 | 7984 | Hs.334 | NM_005435 | NP_005426 |
| 207194_s_at | −1.77347 | ICAM4 | intercellular adhesion molecule 4 (Landsteiner-Wiener blood group) | NM_001544.2 | 3386 | Hs.706750 | NM_001039132 /// NM_001544 /// NM_022377 | NP_001034221 /// NP_001535 /// NP_071772 |
| 208443_x_at | −1.20918 | SHOX2 | short stature homeobox 2 | NM_006884.1 | 6474 | Hs.55967 | NM_001163678 /// NM_003030 /// NM_006884 | NP_001157150 /// NP_003021 /// NP_006875 |
| 209160_at | 1.59131 | AKR1C3 | aldo-keto reductase family 1, member C3 (3-alpha hydroxysteroid dehydrogenase, type II) | AB018580.1 | 8644 | Hs.78183 | NM_003739 | NP_003730 |
| 211343_s_at | 2.22751 | COL13A1 | collagen, type XIII, | M33653.1 | 1305 | Hs.695934 | NM_001130103 /// NM_005203 /// NM_080798 /// NM_080799 /// NM_080800 /// NM_080801 /// NM_080802 /// NM_080803 /// NM_080804 /// NM_080805 /// NM_080806 /// NM_080807 /// NM_080808 /// NM_080809 /// | NP_001123575 /// NP_005194 /// NP_542988 /// NP_542989 /// NP_542990 /// NP_542991 /// NP_542992 /// NP_542993 /// NP_542994 /// NP_542995 /// NP_542996 /// NP_542997 /// NP_542998 /// NP_542999 /// |

TABLE 14-continued

Genes that differentiate carotid stenosis from atrial fibrillation (p < 0.005, fold change > 1.2).
Table 14. Biomarkers that differentiate carotid stenosis from atrial fibrillation

| Probe Set ID | Fold-Change (Carotid vs. Afib) | Gene Symbol | Gene Title | GenBank ID | Entrez Gene ID | UniGene ID | RefSeq Transcript ID | RefSeq Protein ID |
|---|---|---|---|---|---|---|---|---|
| 215219_at | −1.46668 | DOPEY2 | dopey family member 2 | AK025095.1 | 9980 | Hs.204575 | NM_080810 /// NM_080811 /// NM_080812 /// NM_080813 /// NM_080814 /// NM_080815 | NP_543000 /// NP_543001 /// NP_543002 /// NP_543003 /// NP_543004 /// NP_543005 |
| 218656_s_at | 1.57558 | LHFP | lipoma HMGIC fusion partner | NM_005780.1 | 10186 | Hs.507798 | NM_005128 NM_005780 | NP_005119 NP_005771 |
| 224394_at | 1.20322 | RNF7 | ring finger protein 7 | AF312226.1 | 9616 | Hs.134623 | NM_014245 /// NM_183237 | NP_055060 /// NP_899060 |
| 225147_at | 1.29667 | CYTH3 | cytohesin 3 | AL521959 | 9265 | Hs.487479 | NM_004227 | NP_004218 |
| 227522_at | −3.08723 | CMBL | carboxymethylenebutenolidase homolog (Pseudomonas) | AA209487 | 134147 | Hs.192586 | NM_138809 | NP_620164 |
| 228779_at | −1.24601 | LOC146880 | hypothetical LOC146880 | AA524743 | 146880 | Hs.117853 | NR_026899 /// NR_027487 | — |
| 228818_at | 1.4946 | — | — | BF110792 | — | Hs.661673 | — | — |
| 229487_at | 1.88689 | EBF1 | early B-cell factor 1 | W73890 | 1879 | Hs.573143 | NM_024007 | NP_076870 |
| 230494_at | −1.20819 | SLC20A1 | Solute carrier family 20 (phosphate transporter), member 1 | AI671885 | 6574 | Hs.187946 | NM_005415 | NP_005406 |
| 230710_at | −1.20654 | — | — | W05495 | — | Hs.446388 | — | — |
| 231021_at | −1.20317 | SLC6A19 | solute carrier family 6 (neutral amino acid transporter), member 19 | AI627358 | 340024 | Hs.481478 | NM_001003841 | NP_001003841 |
| 231411_at | 1.55003 | LHFP | Lipoma HMGIC fusion partner | BE674089 | 10186 | Hs.507798 | NM_005780 | NP_005771 |
| 232329_at | 1.40571 | RANBP10 | RAN binding protein 10 | AV717059 | 57610 | Hs.368569 | NM_020850 | NP_065901 |
| 233621_s_at | −2.0246 | ARHGEF12 | Rho guanine nucleotide exchange factor (GEF) 12 | AL137456.1 | 23365 | Hs.24598 | NM_015313 | NP_056128 |
| 233742_at | −1.29936 | C16orf68 | Chromosome 16 open reading frame 68 | AK000114.1 | 79091 | Hs.306380 | NM_024109 | NP_077014 |
| 235874_at | 1.2001 | PRSS35 | protease, serine, 35 | AL574912 | 167681 | Hs.98381 | NM_153362 | NP_699193 |
| 236548_at | −1.25287 | GIPC2 | GIPC PDZ domain containing family, member 2 | AL044570 | 54810 | Hs.659356 | NM_017655 | NP_060125 |
| 236963_at | 1.70511 | — | — | AV700946 | — | Hs.432337 | — | — |
| 238360_s_at | −1.28837 | — | — | AI885665 | — | Hs.634043 | — | — |
| 238557_at | −1.25224 | LOC100144603 | hypothetical transcript | R58282 | 100144603 | Hs.657275 | NR_021492 | — |
| 238827_at | −1.36024 | — | — | BE843544 | — | Hs.666833 | — | — |
| 239977_at | 1.26675 | C12orf42 | chromosome 12 open reading frame 42 | AI638494 | 374470 | Hs.534649 | NM_001099336 /// NM_198521 | NP_001092806 /// NP_940923 |
| 242462_at | 1.23474 | LOC100127980 | hypothetical protein LOC100127980 | BE218570 | 100127980 | Hs.595153 | XM_001720119 /// XM_001722650 | XP_001720171 /// XP_001722702 |

TABLE 15

A list of 40 genes that differentiate atrial fibrillation from non-atrial fibrillation (p < 0.005, fold change > |1.2|).
Table 15. Biomarkers that differentiate atrial fibrillation from non-atrial fibrillation

| Probe Set ID | Fold-Change (Afib vs. NonAfib) | Gene Symbol | Gene Title | GenBank ID | Entrez Gene ID | UniGene ID | RefSeq Transcript ID | RefSeq Protein ID |
|---|---|---|---|---|---|---|---|---|
| 1553730_x_at | −1.20376 | LRRC43 | leucine rich repeat containing 43 | NM_152759.1 | 254050 | Hs.374856 | NM_001098519 /// NM_152759 | NP_001091989 /// NP_689972 |
| 1555677_s_at | 1.21973 | SMC1A | structural maintenance of chromosomes 1A | BC046147.1 | 8243 | Hs.211602 | NM_006306 | NP_006297 |
| 1558540_s_at | −1.25589 | MIF /// SLC2A11 | macrophage migration inhibitory factor (glycosylation-inhibiting factor) /// solute carrier family 2 (facilitated glucose transporter), member 11 | AK055523.1 | 4282 /// 66035 | Hs.407995 | NM_001024938 /// NM_001024939 /// NM_002415 /// NM_030807 | NP_001020109 /// NP_001020110 /// NP_002406 /// NP_110434 |
| 1560550_at | −1.2744 | — | — | BC037972.1 | — | Hs.589927 | — | — |
| 1561741_at | −1.29835 | — | — | BC042016.1 | — | Hs.639369 | — | — |
| 1562254_at | 1.45766 | — | — | AK024394.1 | — | — | — | — |
| 1566402_at | 1.79094 | SNORA68 | small nucleolar RNA, H/ACA box 68 | Y11162.1 | 26780 | Hs.684118 | NR_000012 | — |
| 1569609_at | −1.55035 | — | — | BC028185.1 | — | Hs.621293 | — | — |
| 1569701_at | −1.32035 | PER3 | Period homolog 3 (Drosophila) | BC036937.1 | 8863 | Hs.162200 | NM_016831 | NP_058515 |
| 202046_s_at | 1.28563 | GRLF1 | glucocorticoid receptor DNA binding factor 1 | NM_004491.1 | 2909 | Hs.509447 | NM_004491 | NP_004482 |
| 202071_at | 1.43001 | SDC4 | syndecan 4 | NM_002999.1 | 6385 | Hs.632267 | NM_002999 | NP_002990 |
| 202494_at | −1.21636 | PPIE | peptidylprolyl isomerase E (cyclophilin E) | NM_006112.1 | 10450 | Hs.524690 | NM_006112 /// NM_203456 /// NM_203457 | NP_006103 /// NP_982281 /// NP_982282 |
| 211343_s_at | −1.90743 | COL13A1 | collagen, type XIII, alpha 1 | M33653.1 | 1305 | Hs.695934 | NM_001130103 /// NM_005203 /// NM_080798 /// NM_080799 /// NM_080800 /// NM_080801 /// NM_080802 /// NM_080803 /// NM_080804 /// NM_080805 /// NM_080806 /// NM_080807 /// NM_080808 /// NM_080809 /// NM_080810 /// NM_080811 /// NM_080812 /// NM_080813 /// NM_080814 /// NM_080815 | NP_001123575 /// NP_005194 /// NP_542988 /// NP_542989 /// NP_542990 /// NP_542991 /// NP_542992 /// NP_542993 /// NP_542994 /// NP_542995 /// NP_542996 /// NP_542997 /// NP_542998 /// NP_542999 /// NP_543000 /// NP_543001 /// NP_543002 /// NP_543003 /// NP_543004 /// NP_543005 |
| 213747_at | 1.25775 | — | — | AA047234 | — | — | — | — |
| 214964_at | 1.26326 | — | — | AA554430 | — | Hs.661763 | — | — |

TABLE 15-continued

A list of 40 genes that differentiate atrial fibrillation from non-atrial fibrillation (p < 0.005, fold change > |1.2|).
Table 15. Biomarkers that differentiate atrial fibrillation from non-atrial fibrillation

| Probe Set ID | Fold-Change (Afib vs. NonAfib) | Gene Symbol | Gene Title | GenBank ID | Entrez Gene ID | UniGene ID | RefSeq Transcript ID | RefSeq Protein ID |
|---|---|---|---|---|---|---|---|---|
| 224336_s_at | −1.24201 | DUSP16 | dual specificity phosphatase 16 | AB052156.1 | 80824 | Hs.536535 | NM_030640 | NP_085143 |
| 225097_at | 1.25832 | HIPK2 | homeodomain interacting protein kinase 2 | BF594155 | 28996 | Hs.397465 | NM_001113239 /// NM_022740 /// XM_001716827 /// XM_925800 | NP_001106710 /// NP_073577 /// XP_001716879 /// XP_930893 |
| 225214_at | 1.20457 | LOC100129034 | hypothetical protein LOC100129034 | AI762915 | 100129034 | Hs.654980 | NR_027406 /// XR_079577 | — |
| 227775_at | −1.45039 | BRUNOL6 | bruno-like 6, RNA binding protein (Drosophila) | BE467313 | 60677 | Hs.348342 | NM_052840 | NP_443072 |
| 227846_at | −1.23421 | GPR176 | G protein-coupled receptor 176 | AA526584 | 11245 | Hs.37196 | NM_007223 | NP_009154 |
| 229074_at | 1.25524 | — | — | AI692267 | — | Hs.598990 | — | — |
| 229189_s_at | −1.59286 | — | — | BF672306 | — | Hs.438950 | — | — |
| 229190_at | −1.67118 | — | — | BF672306 | — | Hs.438950 | — | — |
| 230506_at | −1.494 | C6orf164 | chromosome 6 open reading frame 164 | NM_022084.1 | 63914 | Hs.645177 | NR_026784 | — |
| 231219_at | 1.42855 | CMTM1 | CKLF-like MARVEL transmembrane domain containing 1 | AI825627 | 113540 | Hs.15159 | NM_052999 /// NM_181268 /// NM_181269 /// NM_181270 /// NM_181271 /// NM_181272 /// NM_181283 /// NM_181296 | NP_443725 /// NP_851785 /// NP_851786 /// NP_851787 /// NP_851788 /// NP_851789 /// NP_851800 /// NP_851813 |
| 234142_at | −1.20672 | — | — | AK025053.1 | — | Hs.612895 | — | — |
| 235480_at | −1.36329 | MAP3K7IP1 | Mitogen-activated protein kinase kinase kinase 7 interacting protein 1 | AA063633 | 10454 | Hs.507681 | NM_006116 /// NM_153497 | NP_006107 /// NP_705717 |
| 235843_at | 1.46959 | — | — | BF448158 | — | Hs.710512 | — | — |
| 236963_at | −2.00452 | — | — | AV700946 | — | Hs.432337 | — | — |
| 237075_at | 1.95707 | — | — | AI191591 | — | — | — | — |
| 237816_at | 1.38498 | — | — | AA702582 | — | Hs.687470 | — | — |
| 239069_s_at | −1.39094 | — | — | BF691045 | — | Hs.649155 | — | — |
| 239718_at | −1.31179 | — | — | R42552 | — | Hs.718467 | — | — |
| 240369_at | 1.35893 | TTC7A | Tetratricopeptide repeat domain 7A | AW195569 | 57217 | Hs.370603 | NM_020458 | NP_065191 |
| 241797_at | 1.21912 | — | — | AI904095 | — | Hs.687709 | — | — |
| 243603_at | 1.21948 | — | — | AI973041 | — | Hs.672035 | — | — |
| 244646_at | −1.2136 | — | — | AW972881 | — | Hs.663316 | — | — |

TABLE 16

The 38 endogenous reference biomarkers stably expressed in
blood for use in normalization and as control levels.
Table 16. Stably expressed endogenous reference biomarkers

| Probe Set ID | Gene Symbol | Gene Title | Gen Bank ID | UniGene ID | RefSeq Transcript ID | RefSeq Protein ID |
|---|---|---|---|---|---|---|
| 201499_s_at | USP7 | ubiquitin specific peptidase 7 (herpes virus-associated) | NM_003470.1 | Hs.706830 | NM_003470 | NP_003461 |
| 202501_at | MAPRE2 | microtubule-associated protein, RP/EB family, member 2 | NM_014268.1 | Hs.532824 | NM_001143826 /// NM_001143827 /// NM_014268 /// NR_026570 | NP_001137298 /// NP_001137299 /// NP_055083 |
| 202573_at | CSNK1G2 | casein kinase 1, gamma 2 | AL530441 | Hs.651905 | NM_001319 | NP_001310 |
| 203280_at | SAFB2 | scaffold attachment factor B2 | NM_014649.1 | Hs.655392 | NM_014649 | NP_055464 |
| 204842_x_at | PRKAR2A | protein kinase, cAMP-dependent, regulatory, type II, alpha | BC002763.1 | Hs.631923 | NM_004157 | NP_004148 |
| 206138_s_at | PI4KB | phosphatidylinositol 4-kinase, catalytic, beta | NM_002651.1 | Hs.632465 | NM_002651 | NP_002642 |
| 207159_x_at | CRTC1 | CREB regulated transcription coactivator 1 | NM_025021.1 | Hs.371096 | NM_001098482 /// NM_015321 | NP_001091952 /// NP_056136 |
| 208630_at | HADHA | hydroxyacyl-Coenzyme A dehydrogenase/3-ketoacyl-Coenzyme A thiolase/enoyl-Coenzyme A hydratase (trifunctional protein), alpha subunit | AI972144 | Hs.516032 | NM_000182 | NP_000173 |
| 208786_s_at | MAP1LC3B | microtubule-associated protein 1 light chain 3 beta | AF183417.1 | Hs.356061 | NM_022818 | NP_073729 |
| 209192_x_at | KAT5 | K(lysine) acetyltransferase 5 | BC000166.2 | Hs.397010 | NM_006388 /// NM_182709 /// NM_182710 | NP_006379 /// NP_874368 /// NP_874369 |
| 210474_s_at | CDC2L1 /// CDC2L2 | cell division cycle 2-like 1 (PITSLRE proteins) /// cell division cycle 2-like 2 (PITSLRE proteins) | U04819.1 | Hs.651228 | NM_024011 /// NM_033486 /// NM_033487 /// NM_033488 /// NM_033489 /// NM_033492 /// NM_033493 /// NM_033529 | NP_076916 /// NP_277021 /// NP_277022 /// NP_277023 /// NP_277024 /// NP_277027 /// NP_277028 /// NP_277071 |
| 211040_x_at | GTSE1 | G-2 and S-phase expressed 1 | BC006325.1 | Hs.386189 | NM_016426 | NP_057510 |
| 211289_x_at | CDC2L1 /// CDC2L2 | cell division cycle 2-like 1 (PITSLRE proteins) /// cell division cycle 2-like 2 (PITSLRE proteins) | AF067524.1 | Hs.651228 | NM_024011 /// NM_033486 /// NM_033487 /// NM_033488 /// NM_033489 /// NM_033492 /// NM_033493 /// NM_033529 | NP_076916 /// NP_277021 /// NP_277022 /// NP_277023 /// NP_277024 /// NP_277027 /// NP_277028 /// NP_277071 |
| 213311_s_at | TCF25 | transcription factor 25 (basic helix-loop-helix) | BF000251 | Hs.415342 | NM_014972 | NP_055787 |
| 214665_s_at | CHP | calcium binding protein P22 | AK000095.1 | Hs.406234 | NM_007236 | NP_009167 |
| 215063_x_at | LRRC40 | leucine rich repeat containing 40 | AL390149.1 | Hs.147836 | NM_017768 | NP_060238 |
| 215200_x_at | — | — | AK022362.1 | Hs.663419 | — | — |
| 215568_x_at | hCG 2003956 /// LYPLA2 /// LYPLA2P1 | hCG2003956 /// lysophospholipase II /// lysophospholipase II pseudogene 1 | AL031295 | Hs.533479 | NM_007260 /// NR_001444 | NP_009191 |
| 216038_x_at | DAXX | death-domain associated protein | BE965715 | Hs.336916 | NM_001141969 /// NM_001141970 /// NM_001350 /// NR_024517 | NP_001135441 /// NP_001135442 /// NP_001341 |
| 217393_x_at | UBE2NL | ubiquitin-conjugating enzyme E2N-like | AL109622 | Hs.585177 | NM_001012989 | NP_001013007 |
| 217549_at | — | — | AW574933 | Hs.527860 | — | — |
| 217672_x_at | EIF1 | eukaryotic translation initiation factor 1 | BF114906 | Hs.150580 | NM_005801 | NP_005792 |
| 217938_s_at | KCMF1 | potassium channel modulatory factor 1 | NM_020122.1 | Hs.654968 | NM_020122 | NP_064507 |
| 218378_s_at | PRKRIP1 | PRKR interacting protein 1 (IL11 inducible) | NM_024653.1 | Hs.406395 | NM_024653 | NP_078929 |
| 218571_s_at | CHMP4A | chromatin modifying protein 4A | NM_014169.1 | Hs.279761 | NM_014169 | NP_054888 |

TABLE 16-continued

The 38 endogenous reference biomarkers stably expressed in
blood for use in normalization and as control levels.
Table 16. Stably expressed endogenous reference biomarkers

| Probe Set ID | Gene Symbol | Gene Title | Gen Bank ID | UniGene ID | RefSeq Transcript ID | RefSeq Protein ID |
|---|---|---|---|---|---|---|
| 219074_at | TMEM184C | transmembrane protein 184C | NM_018241.1 | Hs.203896 | NM_018241 | NP_060711 |
| 220052_s_at | TINF2 | TERF1 (TRF1)-interacting nuclear factor 2 | NM_012461.1 | Hs.496191 | NM_001099274 /// NM_012461 | NP_001092744 /// NP_036593 |
| 220411_x_at | PODNL1 | podocan-like 1 | NM_024825.1 | Hs.448497 | NM_001146254 /// NM_001146255 /// NM_024825 | NP_001139726 /// NP_001139727 /// NP_079101 |
| 221813_at | FBXO42 | F-box protein 42 | AI129395 | Hs.522384 | NM_018994 | NP_061867 |
| 222207_x_at | LOC441258 | Williams Beuren syndrome chromosome region 19 pseudogene | AK024602.1 | Hs.711232 | — | — |
| 222733_x_at | RRP1 | ribosomal RNA processing 1 homolog (*S. cerevisiae*) | BC000380.1 | Hs.110757 | NM_003683 | NP_003674 |
| 224667_x_at | C10orf104 | chromosome 10 open reading frame 104 | AK023981.1 | Hs.426296 | NM_173473 | NP_775744 |
| 224858_at | ZDHHC5 | zinc finger, DHHC-type containing 5 | AK023130.1 | Hs.27239 | NM_015457 | NP_056272 |
| 225403_at | C9orf23 | chromosome 9 open reading frame 23 | AL528391 | Hs.15961 | NM_148178 /// NM_148179 | NP_680544 /// NP_680545 |
| 226253_at | LRRC45 | leucine rich repeat containing 45 | BE965418 | Hs.143774 | NM_144999 | NP_659436 |
| 227651_at | NACC1 | nucleus accumbens associated 1, BEN and BTB (POZ) domain containing | AI498126 | Hs.531614 | NM_052876 | NP_443108 |
| 232190_x_at | LOC100133445 /// LOC115110 | hypothetical LOC100133445 /// hypothetical protein LOC115110 | AI393958 | Hs.132272 | NR_026927 /// XR_036887 /// XR_038144 | — |
| 49878_at | PEX16 | peroxisomal biogenesis factor 16 | AA523441 | Hs.100915 | NM_004813 /// NM_057174 | NP_004804 /// NP_476515 |

Example 3

Exemplary Flow Outline of Using Gene Expression Analysis for the Diagnosis of the Occurrence of Ischemic Stroke and the Cause of Ischemic Stroke The following example provides an exemplary outline of using the biomarkers described herein for the diagnosis of the occurrence and cause of stroke in a patient suspected of having a stroke.

(1) Detection of biomarkers can be performed using a microarray, e.g., a microfluidics approach. cDNA from the patient's RNA in a blood sample is prepared and labeled (e.g., with a fluorophore). The labeled cDNA is hybridized to probes on the array within the microfluidics device. The fluorescence of the bound cDNA is measured to provide a quantitative measure of the amount of RNA for each gene expressed in the blood of the patient.

(2) The amount of RNA for at least about 15 target genes is first measured in the blood sample. The amount of RNA for at least about 30 endogenous reference biomarkers is measured in the blood sample. The amounts of RNA for each target gene is normalized to the reference genes (geometric average) and a normalized expression value obtained for each target gene. The expression of all of the target genes (15 or more) is then used as input into a predictive equation (support vector machine—for example) that then determines whether the gene expression profile for the subject is most similar to that for stroke or control, and whether the gene expression profile for the subjects is most similar to cardioembolic stroke, atheroembolic stroke, or neither.

(3) Based upon the results of the testing for the above biomarkers, a regime for the prevention and/or treatment of stroke is prescribed and/or administered to the patient.
(a) Patients with a positive diagnosis of stroke, based on the biomarkers of Table 7A can be subject to further confirmatory diagnostic testing, e.g., MRI imaging of brain and vessels, blood tests, EKG, echocardiogram, others.
(b) Patients with a negative diagnosis of stroke, based on the biomarkers of Table 7A can be sent home, or subject to diagnostic analysis and/or testing for a different condition.
(c) Cryptogenic stroke—if determined to be cardioembolic, e.g., based on the biomarkers of Tables 13A and 15, an anticoagulant may be prescribed or administered.
(d) Cryptogenic stroke—if determined to be atherosclerotic, e.g., based on the biomarkers of Table 14, the patient can be subject to vascular imaging to image carotid and other brain vessels; an anti-platelet agent may be prescribed or administered.
(e) If a diagnosis of cardioembolic stroke, e.g., based on the biomarkers of Tables 13A and 15, an anticoagulant may be prescribed or administered.
(f) If a diagnosis of large vessel atheroembolic stroke, e.g., based on the biomarkers of Table 14, the patient can be subject to vascular imaging to image carotid and other brain vessels. An anti-platelet agent may be prescribed or administered, e.g., if stenosis <50% or if intracranial or aortic atherosclerosis. Recommend or perform carotid surgery if stenosis >50%.

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

What is claimed is:

1. A solid support attached to nucleic acids that hybridize to ischemia biomarkers comprising ring finger protein 141 (RNF141), C-type lectin domain family 4, member E (CLEC4E), TIMP metallopeptidase inhibitor 2 (TIMP2), putative homeodomain transcription factor 1 (PHTF1), chemokine-like factor (CKLF), Ras-related GTP binding D (RRAGD), RhoGEF and PH domain containing 4 (FGD4), cytoplasmic polyadenylation element binding protein 2 (CPEB2), similar to hCG1994130 (LOC100290882), UBX domain protein 2B (UBXN2B), ectonucleoside triphosphate diphosphohydrolase 1 (ENTPD1), bone marrow stromal cell antigen 1 (BST1), leukotriene B4 receptor (LTB4R), coagulation factor V (F5), interferon-related developmental regulator 1 (IFRD1), KIAA0319, chromatin modifying protein 1B (CHMP1B), multiple C2 domains, transmembrane 1 (MCTP1), vanin 3 (VNN3), antagonist of mitotic exit network 1 homolog (AMN1), lysosomal-associated membrane protein 2 (LAMP2), FCH domain only 2 (FCHO2), zinc finger protein 608 (ZNF608), RAS (RAD and GEM)-like GTP binding 2 (REM2), Quaking homolog, KH domain RNA binding (QKI), RNA binding motif protein 25 (RBM25), Fatty acyl CoA reductase 2 (FAR2), ST3 beta-galactoside alpha-2,3-sialyltransferase 6 (ST3GAL6), Heterogeneous nuclear ribonucleoprotein H2 (HNRNPH2), GRB2-associated binding protein 1 (GAB1), ubiquitin protein ligase E3 component n-recognin 5 (UBR5), VAMP (vesicle-associated membrane protein)-associated protein A (VAPA), phosphoglucomutase 5 (PGM5), coiled-coil domain containing 144C (CCDC144C), similar to coiled-coil domain containing 144B (LOC100134159), leukocyte cell-derived chemotaxin 2 (LECT2), short stature homeobox (SHOX), T-box 5 (TBX5), serine palmitoyltransferase, long chain base subunit 3 (SPTLC3), SNAP25-interacting protein (SNIP), RNA binding motif, single stranded interacting protein (RBMS3), prostate-specific P704P (P704P), thrombospondin, type I, domain containing 4 (THSD4), FAT tumor suppressor homolog 3 (FAT3), small nuclear ribonucleoprotein polypeptide N (SNRPN), glycine-N-acyltransferase-like 1 (GLYATL1), glutamate decarboxylase-like 1 (GADL1), coxsackie virus and adenovirus receptor (CXADR), ovo-like 2 (OVOL2), Spi-B transcription factor (Spi-1/PU.1 related) (SPIB), brix domain containing 5 (BXDC5), unc-5 homolog B (UNC5B), astrotactin 2 (ASTN2), FLJ35934, ankyrin repeat domain 28 (ANKRD28), coiled-coil domain containing 144A (CCDC144A), translocase of inner mitochondrial membrane 8 homolog A (TIMM8A), aldolase A, fructose-bisphosphate pseudogene 2 (ALDOAP2), LIM domain binding 3 (LDB3), protein tyrosine phosphatase, receptor type D (PTPRD), similar to PTPRF interacting protein binding protein 1 (LOC729222), PTPRF interacting protein, binding protein 1 (liprin beta 1) (PPFIBP1), chemokine (C-C motif) receptor-like 1 (CCRL1), heterogeneous nuclear ribonucleoprotein U-like 2(HNRNPUL2), Fc receptor-like 4 (FCRL4), embryonic lethal, abnormal vision-like 2 (ELAVL2), protogenin homolog (PRTG), distal-less homeobox 6 (DLX6), forkhead box A2 (FOXA2), stearoyl-CoA desaturase 5 (SCDS), gamma-aminobutyric acid (GABA) A receptor, beta 2 (GABRB2), Glycophorin A (MNS blood group) (GYPA), LOC283027, LOC344595, Ribosomal protein L22 (RPL22), LOC100129488 and SH3-domain GRB2-like 3 (SH3GL3), wherein the solid support is attached to 100 or fewer nucleic acids.

2. The solid support of claim 1, further comprising a plurality of nucleic acids that hybridize to a plurality of the genes set forth in Tables 13A and 13B selected from the group consisting of EBF1, GRM5, TSKS, ENPP2, AP3S2, LRRC37A3, C16orf68, LOC284751, IRF6, LHFP, BANK1, ARHGEF5, ZNF254, TFDP1, COL13A1, GSTK1, ADAMTSL4, P2RX5, LHFP, PIK3C2B, CHURC1, EXT2, HLA-DOA, OOEP, ZNF185, TMEM19, FCRL1, FLJ40125, ARHGEF12, CLEC18A, CD46, PTPN20A///PTPN20B, and C19orf28.

3. The solid support of claim 1, further comprising a plurality of nucleic acids that hybridize to a plurality of the genes set forth in Table 14 selected from the group consisting of EBF1, FLJ31945, C16orf68, SLC20A1, DOPEY2, COL13A1, LHFP, LOC284751, GRMS, LOC100144603, MTBP, SHOX2, ARHGEFS, RNF7, CLASP2, GIPC2, RANBP10, CMBL, LOC100127980, CYTH3, PROCR, LOC146880, SLC6A19, ICAM4, C12orf42, ARHGEF12, PRSS35, NTSE, LOC100271832, LHFP, NTSE and AKR1C3.

4. The solid support of claim 1, further comprising a plurality of nucleic acids that hybridize to a plurality of the genes set forth in Table 15 selected from the group consisting of CMTM1, COL13A1, SDC4, C6orf164, GPR176, BRUNOL6, SNORA68, MIF///SLC2A11, DUSP16, HIPK2, TTC7A, PPIE, GRLF1, MAP3K7IP1, LOC100129034, PER3, SMC1A, and LRRC43.

5. The solid support of claim 1, further comprising a plurality of nucleic acids that hybridize to a plurality of the genes set forth in Table 16 selected from the group consisting of USP7, MAPRE2, CSNK1G2, SAFB2, PRKAR2A, PI4KB, CRTC1, HADHA, MAP1LC3B, KATS, CDC2L 1///CDC2L2, GTSE1, TCF25, CHP, LRRC40, hCG_2003956///LYPLA2///LYPLA2P1, DAXX, UBE2NL, EIF1, KCMF1, PRKRIP1, CHMP4A, TMEM184C, TINF2, PODNL1, FBXO42, LOC441258, RRP1, C10orf104, ZDHHC5, C9orf23, LRRC45, NACC1, LOC100133445///LOC115110, PEX16.

6. The solid support of claim 1, wherein the solid support is a microarray.

7. A kit comprising a solid support of claim 1.

8. A solid support comprising a plurality of nucleic acids that hybridize to a plurality of genes consisting of RNF141, CLEC4E, TIMP2, PHTF1, CKLF, RRAGD, CLEC4E, FGD4, CPEB2, LOC100290882, UBXN2B, ENTPD1, BST1, LTB4R, F5, IFRD1, KIAA0319, CHMP1B, MCTP1, VNN3, AMN1, LAMP2, FCHO2, ZNF608, REM2, QKI, RBM25, FAR2, ST3GAL6, HNRNPH2, GAB1, UBR5, VAPA, PGM5, CCDC144C, LOC100134159, LECT2, SHOX, TBX5, SPTLC3, SNIP, RBMS3, P704P, THSD4, FAT3, SNRPN, GLYATL1, GADL1, CXADR, OVOL2, SPIB, BXDC5, UNC5B, ASTN2, FLJ35934, ANKRD28, CCDC144A, TIMM8A, ALDOAP2, LDB3, PTPRD, LOC729222, PPFIBP1, CCRL1, HNRNPUL2, FCRL4, ELAVL2, PRTG, DLX6, FOXA2, SCD5, GABRB2, GYPA, LOC283027, LOC344595, LOC100129488, RPL22, SH3GL3, EBF1, GRM5, TSKS, ENPP2, AP3S2, LRRC37A3, C16orf68, LOC284751, IRF6, LHFP, BANK1, ARHGEF5, ZNF254, TFDP1, COL13A1, GSTK1, ADAMTSL4, P2RX5, LHFP, PIK3C2B, CHURC1, EXT2, HLA-DOA, OOEP, ZNF185, TMEM19, FCRL1, FLJ40125, ARHGEF12, CLEC18A, CD46, PTPN20A///PTPN20B, C19orf28, FLJ31945, C16orf68, SLC20A1, DOPEY2, COL13A1, LHFP, LOC284751, GRM5, LOC100144603, MTBP, SHOX2, ARHGEF5, RNF7, CLASP2, GIPC2, RANBP10, CMBL, LOC100127980, CYTH3, PROCR, LOC146880, SLC6A19, ICAM4, C12orf42, ARHGEF12, PRSS35, NT5E, LOC100271832, LHFP, NT5E, AKR1C3, CMTM1, COL13A1, SDC4, C6orf164, GPR176, BRUNOL6, SNORA68, MIF///SLC2A11, DUSP16, HIPK2, TTC7A, PPIE, GRLF1, MAP3K7IP1, LOC100129034, PER3, SMC1A, and LRRC43, USP7, MAPRE2, CSNK1G2, SAFB2, PRKAR2A, PI4KB, CRTC1, HADHA, MAP1LC3B, KATS, CDC2L1///CDC2L2, GTSE1, TCF25, CHP, LRRC40, hCG_2003956///LYPLA2///LYPLA2P1, DAXX, UBE2NL, EIF1, KCMF1, PRKRIP1, CHMP4A, TMEM184C, TINF2, PODNL1, FBXO42, LOC441258, RRP1, C10orf104, ZDHHCS, C9orf23, LRRC45, NACC1, LOC100133445///LOC115110 and PEX16.

* * * * *